US007807409B2

(12) United States Patent
Kopetzki

(10) Patent No.: US 7,807,409 B2
(45) Date of Patent: Oct. 5, 2010

(54) METHOD FOR THE RECOMBINANT EXPRESSION OF A POLYPEPTIDE

(75) Inventor: Erhard Kopetzki, Penzberg (DE)

(73) Assignee: Roche Palo Alto LLC, Palo Alto, CA (US)

( * ) Notice: Subject to any disclaimer, the term of this patent is extended or adjusted under 35 U.S.C. 154(b) by 645 days.

(21) Appl. No.: 11/583,573

(22) Filed: Oct. 19, 2006

(65) Prior Publication Data

US 2007/0117185 A1 May 24, 2007

(30) Foreign Application Priority Data

Oct. 21, 2005 (EP) ................................ 05023003
May 24, 2006 (EP) ................................ 06010665

(51) Int. Cl.
*C12N 15/00* (2006.01)
*C12N 15/63* (2006.01)

(52) U.S. Cl. .................................. 435/69.1; 435/320.1

(58) Field of Classification Search ...................... None
See application file for complete search history.

(56) References Cited

U.S. PATENT DOCUMENTS

| | | | |
|---|---|---|---|
| 5,010,182 | A | 4/1991 | Brake et al. |
| 5,888,809 | A | 3/1999 | Allison |
| 2003/0049227 | A1 | 3/2003 | Gillies et al. |
| 2003/0103984 | A1 | 6/2003 | Kohler |
| 2004/0033511 | A1 | 2/2004 | Pfizenmaier et al. |
| 2004/0180035 | A1 | 9/2004 | Gillies |
| 2005/0008642 | A1 | 1/2005 | Graus et al. |

FOREIGN PATENT DOCUMENTS

| | | | |
|---|---|---|---|
| EP | 0 362 179 | A2 | 8/1989 |
| EP | 0 556 111 | A1 | 9/1993 |
| WO | WO 91/16437 | A1 | 10/1991 |
| WO | WO 92/08796 | A1 | 5/1992 |
| WO | WO 94/26910 | A1 | 11/1994 |
| WO | WO 94/28143 | A1 | 12/1994 |
| WO | WO 98/28427 | A1 | 7/1998 |
| WO | WO 00/11033 | A2 | 3/2000 |
| WO | WO 03/016501 | A2 | 2/2003 |
| WO | WO 03/035892 | A2 | 5/2003 |
| WO | WO 2004/046306 | A2 | 6/2004 |

OTHER PUBLICATIONS

Adam, M.A., et al., "Internal Initiation of Translation in Retroviral Vectors Carrying Picornavirus 5' Nontranslated Regions," *J. vol.* 65 (1991) 4985-4990.

Alves, N. L., et al., "Common γ Chain Cytokines: Dissidence in the details," Immun. Letters 108 (2007) 113-120.

Ausubel, F.M., et al. "Current Protocols in Molecular Biology," *John Wiley & Sons, Inc.* vol. 1, 2 & 3. (1997).

Banerji, J., et al, "A Lymphocyte-Specific Cellular Enhancer is Located Downstream of the Joining Region in Immunoglobulin Heavy Chain Genes," *Cell* 33 (1983) 729-40.

Barkocy-Gallagher, G.A., et al., "Synthesis of Precursor Maltose-binding Protein with Proline in the +1 Position of the Cleavage Site Interferes with the Activity of *Escherichia coli* Signal Peptidase I in Vivo," *J Biol.Chem.* vol. 267. No. 2 (1992) pp. 1231-1238.

Bendig, M.M., et al., "The Production of Foreign Proteins in Mammalian Cells," *Genetic Engineering* 7 (1988) 91-127.

Bird, R.E., et al., "Single-Chain Antigen-Binding Proteins," *Science* 242 (1988) 423-426.

Burnette, W. N. "Western Blotting": Electrophoretic Transfer of Proteins from Sodium Dodecyl Sulfate—Polyacrylamide Gels to Unmodified Nitrocellulose and Radiographic Detection with Antibody and Radioiodinated Protein A, *Anal. Biochem.* 112 (1981) 195-203.

Davies, M.V., et al. "The Sequence Context of the Initiation Codon in the Encephalomyocarditis Virus Leader Modulates Efficiency of Internal Translation Initiation," *J. Virol.* 66 (1992).

Edelman, G.M., et al., "The Covalent Structure of an Entire γG Immunoglobulin Molecule," *Proc. Natl. Acad. Science* 63 (1969) 78-85.

Goeddel, D.V., et al., "Systems for Heterologous Gene Expression," *Methods Enzymol.* 185 (1990) 3-7.

Gossen, M., et al., "Tight Control of Gene Expression in Mammalian Cells by Tetracycline-Responsive Promotors," *Proc. Natl. Acad. Science* 89 (1992) 5547-5551.

Gossen, M., et al., "Inducible Gene Expression Systems for Higher Eukaryotic Cells," *Current Opinion Biotech.* 5 (1994) 516-520.

Hood, L.E., "Immunology," Benjamin, N. Y., 2nd Edition (1984).

Hunkapillar, T., et al., "The Growing Immunoglobulin Gene Superfamily," *Nature* 323 (1986) pp. 15-16.

Huston, J.S., et al., "Protein Engineering of Antibody Binding Sites: Recovery of Specific Activity in an Anti-digoxin Single-Chain Fv Analogue Produced in *Escherichia Coli*," *Proc. Natl. Acad. Science* 85 (1988) pp. 5879-5883.

Jang, S.K., et al., "Initiation of Protein Synthesis by Internal Entry of Ribosomes into the 5' Nontranslated Region of Encephalomyocarditis Virus RNA in Vivo," *J. Virol.* 63 (1989) pp. 1651-1660.

Kabat, E.A., et al., "Sequences of Proteins of Immunological Interest," *NIH 5th* Edition (1991).

Lemaigre, F.P., "Transcriptional control of genes that regulate glycolysis and gluconeogenesis in adult liver," *Biochem J.* 303 (1994) 1-14.

(Continued)

*Primary Examiner*—Ruixiang Li
(74) *Attorney, Agent, or Firm*—David J. Chang

(57) ABSTRACT

A method for the recombinant production of a heterologous polypeptide in a eukaryotic host cell is described. The host cell comprises an expression plasmid, whereby the expression plasmid comprises in a 5' to 3' direction a) a promoter, b) a nucleic acid encoding a first polypeptide, whose amino acid sequence is selected from Table 1 depending on the first two amino acids of the second polypeptide, c) a nucleic acid encoding a second polypeptide comprising a nucleic acid encoding a heterologous polypeptide, a nucleic acid encoding a linker, and a nucleic acid encoding an immunoglobulin fragment, and d) a 3' untranslated region comprising a polyadenylation signal. Further a plasmid and a kit are described.

10 Claims, 15 Drawing Sheets

OTHER PUBLICATIONS

Loeken, M.R., "Effects of Mutation of the CREB Binding Site of the Somatostatin Promoter on Cyclic AMP Responsiveness in CR-1 Cells," *Gene Expr*. 3 (1993) 253-264.

Lusky, M., et al., "Bovine Papilloma Virus Contains an Activator of Gene Expression at the Distal End of the Early Transcription Unit," *Mol. Cell Bio*. 3 vol. 6 (1983) pp. 1108-1122.

Marino, M.H., et al., "Expression Systems for Heterologous Protein Production," *Biopharm*. 2 (1989) 18-33.

McGehee, R.E. Jr., et al., "Differentiation-Specific Element: a cis-Acting Development Switch Required for the Sustained Transcriptional Expression of the Angiotensinogen Gene during Hormonal-Induced Differentiation of 3T3-L1 Fibroblasts to Adipocytes," *Mol. Endocrinol*. 7 (1993) 551-60.

Meissner, P., et al., "Transient Gene Expression: Recombinant Protein Production with Suspension-Adapted HEK293-EBNA Cells," *Biotechnol. Bioeng*. 75 (2001) 197-203.

Morgan, R.A., et al., "Retroviral vectors containing putative internal ribosome entry sites: Development of a Polycistronic Gene Transfer System and Applications to Human Gene Therapy," *Nucleic Acids Research*, vol. 20, No. 6 (1992) 1293-1299.

Mosser, D.D., et al., "Use of a Dicistronic Expression Cassette Encoding the Green Fluorescent Protein for the Screening and Selection of Cells Expressing Inducible Gene Products," *BioTechiques* 22 (1997) 150-161.

Nothwehr, S.F., et al., "Residues Flanking the COOH-terminal C-region of a Model Eukaryotic Signal Peptide Influence the Site of Its Cleavage by Signal Peptidase and the Extent of Coupling of Its Co-translational Translocation and Proteolytic Processing in Vitro," *J. Biol. Chem*. vol. 265, No. 35 (1990) 21797-21803.

O'Reilly, M.A., et al., "Identification of an Activating Transcription Factor (ATF) Binding Site in the Human Transforming Growth Factor—β2 Promoter," *J. Biol. Chem*. 267 (1992) 19938-43.

Osborne, T.F., et al., "Transcription Control Region Within the Protein-Coding Portion of Adenovirus E1A Genes," *Mol. Cell. Bio*. 4 (1984) 1293-1305.

Pilzkill, T., et al., "Selection of Functional Signal Peptide Cleavage Sites from a Library of Random Sequences," *J. Bacteriology* vol. 176, No. 3 (1994) p. 563-568.

Pelletier, J., et al., "Internal initiation of translation of eukaryotic mRNA directed by a sequence derived from poliovirus RNA," *Nature* 334 (1988) 320-325.

Perlman, D. et al., "A Putative Signal Peptidase Recognition Site and Sequence in Eukaryotic and Prokaryotic Signal Peptides," *J. Mol. Biol*. 167 (1983) 391-409.

Pratap, J., et al., "Effect of signal peptide changes on the extracellular processing of streptokinase from *Escherichia coli*: requirement for secondary structure at the cleavage junction," *Mol. Gen. Genet*. 258 (1998) 326-333.

Ramesh, N., et al., "High-titer Bicistronic Retroviral Vectors Employing Foot-and-Mouth Disease Virus Internal Ribosome Entry Site," *Nucleic Acids Res*. 24 (1996) 2697-2700.

Ratner, L., et. al., "Complete Nucleotide Sequence of the AIDS Virus, HTLV-III," *Nature* 313 (1985) 277-384.

Sambrook, J., et al., "Molecular Cloning: A Laboratory Manual, 2$^{nd}$ Ed.," *Cold Spring Harbor Laboratory Press*, N. Y. (1989).

Sugimoto, Y. et al., "Efficient Expression of Drug-selectable Genes in Retroviral Vectors Under Control of an Internal Ribosome Entry Site," *Biotechnology* 12 (1994) 694-698.

Treisman, R., "The SRE: a growth factor responsive transcriptional regulator," *Seminars in Cancer Biol*. 1 (1990) 47-58.

Watson, J.D., et al., "Molecular Biology of the Gene, 4$^{th}$ Ed." *The Benjamin-Cummings Publishing Company, Inc*. (1987).

Wurm, F., et al., Large-scale transient expression in mammalian cells for recombinant protein production, *Curr. Opin. Biotechnol*. 269 (1999) 156-159.

Yee, J., et al. "Characterization of a Silencer Regulatory Element in the Human Interferon-γ Promoter," *J. Biol. Chem*. 269 (1994) 25728-34.

METHOD FOR THE RECOMBINANT EXPRESSION OF A POLYPEPTIDE

RELATED CASES

This application claims priority from EP05023003.6, filed Oct. 21, 2005, and EP0601066.5, filed May 24, 2006, both incorporated herein by reference

FIELD OF THE INVENTION

The present invention relates to a method for the recombinant expression of a polypeptide in eukaryotic cells.

BACKGROUND OF THE INVENTION

Expression systems for the production of recombinant polypeptides are well-known in the state of the art and are described by, e.g., Marino, M. H., *Biopharm.* 2 (1989) 18-33; Goeddel, D. V., et al., *Methods Enzymol.* 185 (1990) 3-7; Wurm, F., and Bernard, A., *Curr. Opin. Biotechnol.* 10 (1999) 156-59. Polypeptides for use in pharmaceutical applications are preferably produced in mammalian cells such as CHO cells, NS0 cells, Sp2/0 cells, COS cells, HEK cells, BHK cells and the like. The essential elements of an expression plasmid are a prokaryotic plasmid propagation unit, for example for *E. coli*, comprising an origin of replication and a selection marker, an eukaryotic selection marker, and one or more expression cassettes for the expression of the structural gene (s) of interest each comprising a promoter, a structural gene, and a transcription terminator including a polyadenylation signal. For transient expression in mammalian cells, a mammalian origin of replication such as the SV40 Ori or OriP can be included. As promoter, a constitutive or inducible promoter can be selected. For optimized transcription, a Kozak sequence may be included in the 5' untranslated region. For mRNA processing, in particular mRNA splicing and transcription termination, mRNA splicing signals, depending on the organization of the structural gene (exon/intron organization), may be included as well as a polyadenylation signal.

Expression of a gene is performed either as transient or as permanent expression. The polypeptide(s) of interest are in general secreted polypeptides, and therefore contain an N-terminal extension (also known as the signal sequence) which is necessary for the transport/secretion of the polypeptide through the cell into the extracellular medium.

In general, the signal sequence can be derived from any gene encoding a secreted polypeptide. If a heterologous signal sequence is used, it preferably is one that is recognized and processed (i.e. cleaved by a signal peptidase) by the host cell. For secretion in yeast, for example, the native signal sequence of a heterologous gene to be expressed may be substituted by a homologous yeast signal sequence derived from a secreted gene, such as the yeast invertase signal sequence, alpha-factor leader (including *Saccharomyces, Kluyveromyces, Pichia*, and *Hansenula* α-factor leaders, the second described in U.S. Pat. No. 5,010,182), acid phosphatase signal sequence, or the *C. albicans* glucoamylase signal sequence (EP 0 362 179). In mammalian cell expression, the native signal sequence of the protein of interest is satisfactory, although other mammalian signal sequences may be suitable, such as signal sequences from secreted polypeptides of the same or related species, e.g. for immunoglobulins from human or murine origin, as well as viral secretory signal sequences, for example, the herpes simplex glycoprotein D signal sequence. The DNA fragment encoding for such a presegment is ligated in frame to the DNA fragment encoding a polypeptide of interest.

In WO 98/28427 a genetically or chemically prepared fusion protein comprising the Fc immunoglobulin region, a derivative or analog fused to the N-terminal portion of the OB protein is reported. A chimeric molecule, i.e. antibody fusion or fusion protein, comprising a carboxy terminal protein import sequence and an amino terminal cargo region is presented in WO 03/035892.

In US 2003/0049227 a method for the induction of a cytocidal immune response against a tumor in a mammal by administering an immunocytokine, which is a fusion protein comprising an amino-terminal immunoglobulin part and a carboxy-terminal cytokine part, is reported.

WO 91/16437 reports a soluble recombinant fused protein which is stable in the mammalian circulatory system comprising a polypeptide which contains a recognition site for a target molecule, such as a complement receptor site, and is joined to the N-terminal end of an immunoglobulin chain. A fusion protein made up of an antibody and a peptide having a biological activity is reported in US 2003/0103984.

In US 2004/0033511 an antibody-cytokine fusion protein and in US 2004/0180035 an antibody-cytokine immunoconjugate are reported. An immunotoxin comprising Gelonin and an antibody is reported in WO 94/26910.

SUMMARY OF THE INVENTION

The current invention comprises a method for the recombinant production of a heterologous polypeptide in a eukaryotic host cell comprising an expression plasmid, whereby the expression plasmid comprises in a 5' to 3' direction a) a promoter, b) a nucleic acid encoding a first polypeptide, whose amino acid sequence is selected from Table 1 depending on the first two amino acids of the second polypeptide, c) a nucleic acid encoding a second polypeptide comprising a nucleic acid encoding the heterologous polypeptide, a nucleic acid encoding a linker, and a nucleic acid encoding an immunoglobulin fragment, and d) a 3' untranslated region comprising a polyadenylation signal. The method further comprises cultivating the eukaryotic host cell comprising said expression plasmid under conditions suitable for the expression of the second polypeptide, and recovering the second polypeptide from the culture medium.

In one embodiment of the invention the nucleic acid encoding the second polypeptide contains in 5' position to the nucleic acid encoding the heterologous polypeptide an additional nucleic acid encoding either a single amino acid or a dipeptide or the peptide of the amino acid sequence QIWNN (SEQ ID NO: 472) or a fragment thereof.

In another embodiment the immunoglobulin fragment is obtained either from an IgG or from an IgE.

In a further embodiment the eukaryotic cell is a mammalian cell, especially a CHO cell, NS0 cell, Sp2/0 cell, COS cell, K562 cell, BHK cell, PER.C6 cell or HEK cell.

In still another embodiment the linker is a peptide or polypeptide selected from the group consisting of SEQ ID NOs: 06, 07, 08, 09, 10, 139, 140, 554, 555, 556, and 557.

In another embodiment the immunoglobulin fragment comprises the carboxy-terminal constant domain of a heavy or light chain of a naturally occurring or synthetic immunoglobulin, i.e. either the $C_H1$-, the hinge region, the $C_H2$-, the $C_H3$-domain of a heavy chain or the $C_L$-domain of a light chain. Additionally the immunoglobulin fragment comprises a variable domain fragment.

In another embodiment the variable domain fragment is a variable domain of an immunoglobulin heavy or light chain in which of from one to six amino acids of the variable domain are deleted.

In a further embodiment of from one to six regions (FR1, FR2, FR3, CDR1, CDR2, CDR3) of the variable domain are deleted.

In a further embodiment the variable domain is deleted.

In another embodiment the immunoglobulin fragment is derived from a naturally occurring immunoglobulin or a variant thereof.

In a further embodiment the immunoglobulin fragment is derived from an at least partially synthetic immunoglobulin.

In still another embodiment of the invention the amino acid sequence of the heterologous polypeptide is of from 5 to 500 amino acid residues, more preferred of from 10 to 350 amino acid residues, most preferred of from 15 to 150 amino acid residues.

The invention further comprises a plasmid comprising in a 5' to 3' direction a) a promoter, b) a nucleic acid encoding a first polypeptide, whose amino acid sequence is selected from Table 1 depending on the first two amino acids of the second polypeptide, c) a nucleic acid encoding a second polypeptide comprising a nucleic acid encoding a heterologous polypeptide, a nucleic acid encoding a linker, and a nucleic acid encoding an immunoglobulin fragment, and d) a 3'-untranslated region comprising a polyadenylation signal.

The invention still further comprises a kit for the preparation of a plasmid for the expression of a heterologous polypeptide in a eukaryotic cell comprising a plasmid which comprises in a 5' to 3' direction a) a promoter, b) a nucleic acid encoding a first polypeptide, whose amino acid sequence is selected from the group consisting of SEQ ID NO: 36, 37, 319, 320, 321, 322, 323, 324, 325, 326, 327, 328, and 329, c) a nucleic acid encoding a second polypeptide comprising i) a nucleic acid encoding a peptide of the amino acid sequence QIWNN (SEQ ID NO: 472) or a N-terminal fraction thereof, ii) a cloning site comprising at least one restriction cleavage site suitable for the insertion of a nucleic acid encoding a heterologous polypeptide, iii) a nucleic acid encoding a linker selected from the group consisting of SEQ ID NOs 06, 07, 08, 09, 10, 139, 140, 554, 555, 556, and 557, and iv) a nucleic acid encoding an immunoglobulin fragment, and d) a 3'-untranslated region comprising a polyadenylation signal.

DETAILED DESCRIPTION OF THE INVENTION

The current invention comprises a method for the recombinant expression of a heterologous polypeptide of interest in an eukaryotic host cell comprising an expression vector, which contains a suitable promoter, a transcription terminator, a selectable marker, a nucleic acid sequence encoding a polypeptide, and a nucleic acid sequence encoding a signal sequence, whereby the nucleic acid sequence encoding the signal sequence is selected from Table 1 depending on the first two amino acids of the following polypeptide. The nucleic acid sequence encoding the heterologous polypeptide starts within fifteen nucleotides after the end of the nucleic acid sequence encoding the signal sequence. The nucleic acid sequence encoding the heterologous polypeptide can either be inserted within a FR1-region of an immunoglobulin, within a $V_L$-region of an immunoglobulin or within the first constant domain of an immunoglobulin or it can replace all or a fraction of a FR1-region of an immunoglobulin, a $V_L$-region of an immunoglobulin or the first constant domain of an immunoglobulin.

Within the scope of the present invention some of the terms used are defined as follows:

A "nucleic acid molecule" as used herein, refers to a naturally occurring or partially or fully non-naturally occurring nucleic acid encoding a polypeptide which can be produced recombinantly. The nucleic acid molecule can be build up of DNA-fragments which are either isolated or synthesized by chemical means. The nucleic acid molecule can be integrated into another nucleic acid, e.g. in an expression plasmid or the genome/chromosome of a eukaryotic host cell. Plasmid includes shuttle and expression vectors. Typically, the plasmid will also comprise a prokaryotic propagation unit comprising an origin of replication (e.g. the ColE1 origin of replication) and a selectable marker (e.g. ampicillin or tetracycline resistance gene), for replication and selection, respectively, of the vector in bacteria.

An "expression cassette" refers to a nucleic acid sequence that contains the elements necessary for expression and secretion of at least the contained structural gene in a cell.

A nucleic acid molecule is likewise characterized by its nucleic acid sequence consisting of individual nucleotides or/and by an amino acid sequence encoded by the nucleic acid molecule.

A "gene" denotes a segment e.g. on a chromosome or on a plasmid which is necessary for the expression of a peptide, polypeptide or protein. Beside the coding region the gene comprises other functional elements including a promoter, introns, and terminators.

A "structural gene" denotes the coding region of a gene without a signal sequence.

A "resistance gene" or a "selectable marker", which is used interchangeably within this application, is a gene that allows cells carrying the gene to be specifically selected for or against, in the presence of a corresponding selection agent. A useful positive resistance gene is an antibiotic resistance gene. This selectable marker allows the host cell transformed with the gene to be positively selected for in the presence of the corresponding antibiotic; a non-transformed host cell would not be capable to grow or survive under the selective culture conditions. Selectable markers can be positive, negative or bifunctional. Positive selectable markers allow selection for cells carrying the marker, whereas negative selectable markers allow cells carrying the marker to be selectively eliminated. Typically, a selectable marker will confer resistance to a drug or compensate for a metabolic or catabolic defect in the host cell. Resistance genes useful with eukaryotic cells include, e.g., the genes for aminoglycoside phosphotransferase (APH), such as the hygromycin phosphotransferase (hyg), neomycin and G418 APH, dihydrofolate reductase (DHFR), thymidine kinase (tk), glutamine synthetase (GS), asparagine synthetase, tryptophan synthetase (indole), histidinol dehydrogenase (histidinol D), and genes encoding resistance to puromycin, bleomycin, phleomycin, chloramphenicol, Zeocin, and mycophenolic acid. Further marker genes are described in WO 92/08796 and WO 94/28143.

"Regulatory elements" as used herein, refer to nucleotide sequences present in cis, necessary for transcription and/or translation of the gene comprising the nucleic acid sequence encoding a polypeptide of interest. The transcriptional regulatory elements normally comprise a promoter upstream of the structural gene sequence to be expressed, transcriptional initiation and termination sites, and a polyadenylation signal sequence. The term "transcriptional initiation site" refers to the nucleic acid base in the gene corresponding to the first nucleic acid incorporated into the primary transcript, i.e. the mRNA precursor; the transcriptional initiation site may overlap with the promoter sequence. The term "transcriptional termination site" refers to a nucleotide sequence normally represented at the 3' end of a gene of interest to be transcribed, that causes RNA polymerase to terminate transcription. The polyadenylation signal sequence, or poly-A addition signal provides the signal for the cleavage at a specific site at the 3' end of eukaryotic mRNA and the post-transcriptional addition in the nucleus of a sequence of about 100-200 adenine nucleotides (polyA tail) to the cleaved 3' end. The polyadenylation signal sequence may include the consensus sequence AATAAA located at about 10-30 nucleotides upstream from the site of cleavage.

To produce a secreted polypeptide, the structural gene of interest includes a DNA segment that encodes a signal sequence/leader peptide. The signal sequence directs the newly synthesized polypeptide to and through the ER membrane where the polypeptide can be routed for secretion. The signal sequence is cleaved off by a signal peptidases during the protein crosses the ER membrane. As for the function of the signal sequence the recognition by the host cell's secretion machinery is essential. Therefore the used signal sequence has to be recognized by the host cell's proteins and enzymes of the secretion machinery.

Translational regulatory elements include a translational initiation (AUG) and stop codon (TAA, TAG or TGA). An internal ribosome entry site (IRES) can be included in some constructs.

A "promoter" refers to a polynucleotide sequence that controls transcription of a gene/structural gene or nucleic acid sequence to which it is operably linked. A promoter includes signals for RNA polymerase binding and transcription initiation. The promoters used will be functional in the cell type of the host cell in which expression of the selected sequence is contemplated. A large number of promoters including constitutive, inducible and repressible promoters from a variety of different sources, are well known in the art (and identified in databases such as GenBank) and are available as or within cloned polynucleotides (from, e.g., depositories such as ATCC as well as other commercial or individual sources). A "promoter" comprises a nucleotide sequence that directs the transcription of a structural gene. Typically, a promoter is located in the 5' non-coding or untranslated region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee, R. E., et al., *Mol. Endocrinol.* 7 (1993) 551), cyclic AMP response elements (CREs), serum response elements (SREs; Treisman, R., *Seminars in Cancer Biol.* 1 (1990) 47), glucocorticoid response elements (GREs), and binding sites for other transcription factors, such as CRE/ATF (O'Reilly, M. A., et al., *J. Biol. Chem.* 267 (1992) 19938), AP2 (Ye, J., et al., *J. Biol. Chem.* 269 (1994) 25728), SP1, cAMP response element binding protein (CREB; Loeken, M. R., *Gene Expr.* 3 (1993) 253) and octamer factors (see, in general, Watson et al., eds., Molecular Biology of the Gene, 4th ed. (The Benjamin/Cummings Publishing Company, Inc. 1987), and Lemaigre, F. P. and Rousseau, G. G., *Biochem. J.* 303 (1994) 1-14). If a promoter is an inducible promoter, then the rate of transcription increases in response to an inducing agent. In contrast, the rate of transcription is not regulated by an inducing agent if the promoter is a constitutive promoter. Repressible promoters are also known. For example, the c-fos promoter is specifically activated upon binding of growth hormone to its receptor on the cell surface. Tetracycline (tet) regulated expression can be achieved by artificial hybrid promoters that consist e.g. of a CMV promoter followed by two Tet-operator sites. The Tet-repressor binds to the two Tet-operator sites and blocks transcription. Upon addition of the inducer tetracycline, Tet-repressor is released from the Tet-operator sites and transcription proceeds (Gossen, M. and Bujard, H., *Proc Natl Acad Sci USA* 89 (1992) 5547-5551). For other inducible promoters including metallothionein and heat shock promoters, see, e.g., Sambrook et al. (supra) and Gossen et al., *Curr. Opin. Biotech.* 5 (1994) 516-520. Among the eukaryotic promoters that have been identified as strong promoters for high-level expression are the SV40 early promoter, adenovirus major late promoter, mouse metallothionein-I promoter, Rous sarcoma virus long terminal repeat, Chinese hamster elongation factor 1 alpha (CHEF-1, see e.g. U.S. Pat. No. 5,888,809), human EF-1 alpha, ubiquitin, and human cytomegalovirus immediate early promoter (CMV IE).

The "promoter" can be constitutive or inducible. An enhancer (i.e., a cis-acting DNA element that acts on a promoter to increase transcription) may be necessary to function in conjunction with the promoter to increase the level of expression obtained with a promoter alone, and may be included as a transcriptional regulatory element. Often, the polynucleotide segment containing the promoter will include enhancer sequences as well (e.g., CMV or SV40).

An "enhancer", as used herein, refers to a polynucleotide sequence that enhances transcription of a gene or coding sequence to which it is operably linked. Unlike promoters, enhancers are relatively orientation and position independent and have been found 5' or 3' (Lusky, M., et al., *Mol. Cell. Bio.,* 3 (1983) 1108) to the transcription unit, within an intron (Banerji, J., et al., *Cell,* 33 (1983) 729) as well as within the coding sequence itself (Osborne, T. F., et al., *Mol. Cell. Bio.,* 4 (1984) 1293). Therefore, enhancers may be placed upstream or downstream from the transcription initiation site or at considerable distances from the promoter, although in practice enhancers may overlap physically and functionally with promoters. A large number of enhancers, from a variety of different sources are well known in the art (and identified in databases such as GenBank) and available as or within cloned polynucleotide sequences (from, e.g., depositories such as the ATCC as well as other commercial or individual sources). A number of polynucleotides comprising promoter sequences (such as the commonly-used CMV promoter) also comprise enhancer sequences. For example, all of the strong promoters listed above may also contain strong enhancers (see e.g. Bendig, M. M., *Genetic Engineering* 7 (1988) 91-127).

An "internal ribosome entry site" or "IRES" describes a sequence which functionally promotes translation initiation independent from the gene 5' of the IRES and allows two cistrons (open reading frames) to be translated from a single transcript in an animal cell. The IRES provides an independent ribosome entry site for translation of the open reading frame immediately downstream (downstream is used interchangeably herein with 3') of it. Unlike bacterial mRNA which can be polycistronic, i.e. encode several different polypeptides that are translated sequentially from the mRNAs, most mRNAs of animal cells are monocistronic and code for the synthesis of only one protein. With a polycistronic transcript in a eukaryotic cell, translation would initiate from the 5' most translation initiation site, terminate at the first stop codon, and the transcript would be released from the ribosome, resulting in the translation of only the first encoded polypeptide in the mRNA. In a eukaryotic cell, a polycistronic transcript having an IRES operably linked to the second or subsequent open reading frame in the transcript allows the sequential translation of that downstream open reading frame to produce the two or more polypeptides encoded by the same transcript. The use of IRES elements in vector construction has been previously described, see, e.g., Pelletier, J., et al., *Nature* 334 (1988) 320-325; Jang, S. K., et al., *J. Virol.* 63 (1989) 1651-1660; Davies, M. V., et al., *J. Virol.* 66 (1992) 1924-1932; Adam, M. A., et al. *J. Virol.* 65 (1991) 4985-4990; Morgan. R. A., et al. *Nucl. Acids Res.* 20 (1992) 1293-1299; Sugimoto, Y, et al. *Biotechnology* 12 (1994) 694-698; Ramesh, N., et al. *Nucl. Acids Res.* 24 (1996) 2697-2700; and Mosser, D. D. et al, *Biotechniques* 22 (1997) 150-152).

"Operably linked" refers to a juxtaposition of two or more components, wherein the components so described are in a relationship permitting them to function in their intended manner. For example, a promoter and/or enhancer are operably linked to a coding sequence, if it acts in cis to control or modulate the transcription of the linked sequence. Generally, but not necessarily, the DNA sequences that are "operably linked" are contiguous and, where necessary to join two protein encoding regions such as a secretory leader and a polypeptide, contiguous and in reading frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within or downstream of coding sequences and at considerable distance from the promoter. A polyadenylation site is operably linked to a coding sequence if it is located at the downstream end of the coding sequence such that transcription proceeds through the coding sequence into the polyadenylation sequence. Linking is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

The term "expression" as used herein refers to transcription or translation occurring within a host cell. The level of transcription of a desired product in a host cell can be determined on the basis of the amount of corresponding mRNA that is present in the cell. For example, mRNA transcribed from a selected sequence can be quantitated by PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g. by ELISA, by assaying for the biological activity of the protein, or by employing assays that are independent of such activity, such as Western blotting or radioimmunoassay, using antibodies that recognize and bind to the protein (see Sambrook et al., 1989, supra).

A "host cell" refers to a cell into which the gene encoding the polypeptide of the invention is introduced. Host cell includes both prokaryotic cells used for propagation of the plasmids/vectors, and eukaryotic cells for expression of the structural gene. Typically, the eukaryotic cells are mammalian cells.

A "polypeptide" is a polymer of amino acid residues joined by peptide bonds, whether produced naturally or synthetically. Polypeptides of less than about 20 amino acid residues may be referred to as "peptides." Polypeptides comprising one or more polypeptide chains or comprising an amino acid chain of a length of 100 amino acids or more may be referred to as "proteins".

A "protein" is a macromolecule comprising one or more polypeptide chains whereby at least one chain has an amino acid length of 100 amino acids or more. A protein may also comprise non-peptidic components, such as carbohydrate groups. Carbohydrates and other non-peptidic substituents may be added to a protein by the cell in which the protein is produced, and may vary with the type of cell. Proteins are defined herein in terms of their amino acid backbone structures; additions such as carbohydrate groups are generally not specified, but may be present nonetheless.

"Heterologous DNA" or "heterologous polypeptide" refers to a DNA molecule or a polypeptide, or a population of DNA molecules or a population of polypeptides, that do not exist naturally within a given host cell. DNA molecules heterologous to a particular host cell may contain DNA derived from the host cell species (i.e. endogenous DNA) so long as that host DNA is combined with non-host DNA (i.e. exogenous DNA). For example, a DNA molecule containing a non-host DNA segment encoding a polypeptide operably linked to a host DNA segment comprising a promoter is considered to be a heterologous DNA molecule. Conversely, a heterologous DNA molecule can comprise an endogenous structural gene operably linked with an exogenous promoter.

A peptide or polypeptide encoded by a non-host DNA molecule is a "heterologous" peptide or polypeptide.

A "cloning vector" is a nucleic acid molecule, such as a plasmid, cosmid, phageimid or bacterial artificial chromosome (BAC), which has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a resistance gene that is suitable for use in the identification and selection of cells transformed with the cloning vector. Resistance genes typically include genes that provide tetracycline resistance or ampicillin resistance.

An "expression plasmid" is a nucleic acid molecule encoding a protein to be expressed in a host cell. Typically, an expression plasmid comprises a prokaryotic plasmid propagation unit, e.g. for *E. coli*, comprising an origin of replication, and a selection marker, an eukaryotic selection marker, and one or more expression cassettes for the expression of the structural gene(s) of interest comprising a promoter, a structural gene, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

A "polycistronic transcription unit" is a transcription unit in which more than one structural gene is under the control of the same promoter.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e. at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The term "immunoglobulin" refers to a protein consisting of one or more polypeptides substantially encoded by immunoglobulin genes. The recognized immunoglobulin genes include the different constant region genes as well as the myriad immunoglobulin variable region genes. Immunoglobulins may exist in a variety of formats, including, for example, Fv, Fab, and F(ab)2 as well as single chains (scFv) (e.g. Huston, J. S., et al., *Proc Natl Acad Sci USA* 85 (1988) 5879-5883; Bird, R. E., et al., *Science* 242 (1988) 423-426; and, in general, Hood et al., Immunology, Benjamin N.Y., 2nd edition (1984), and Hunkapiller, T., and Hood, L., *Nature* 323 (1986) 15-16).

An immunoglobulin in general comprises at least two light chain polypeptides and two heavy chain polypeptides. Each of the heavy and light polypeptide chains may contain a variable region (generally the amino terminal portion of the polypeptide chain) which contains a binding domain that is able to interact with an antigen. Each of the heavy and light polypeptide chains comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q).

The variable domain of an immunoglobulin's light or heavy chain in turn comprises different segments, i.e. four framework regions (FR) and three hypervariable regions (CDR).

An "immunoglobulin fragment" denotes a polypeptide comprising at least the constant domains of a chain of an immunoglobulin, i.e. $C_H1$, hinge-region, $C_H2$, and $C_H3$ and optionally $C_H4$ of a heavy chain of an immunoglobulin or $C_L$ of a light chain of an immunoglobulin. Also comprised are derivatives and variants thereof. Additionally a variable domain, in which one or more amino acids or amino acid regions are deleted, may be present. In a preferred embodiment the variable domain is deleted in the immunoglobulin fragment.

"Transcription terminator" as denoted within this application is a DNA sequence of 50-750 base pairs in length which gives the RNA polymerase the signal for termination of the mRNA synthesis. Very efficient (strong) terminators at the 3' end of an expression cassette are advisable to prevent the RNA polymerase from reading through particularly when using strong promoters. Inefficient transcription terminators can lead to the formation of an operon-like mRNA which can be the reason for an undesired, e.g. plasmid-coded, gene expression.

The term "linker" as used within this application denotes peptide linkers of natural or synthetic origin. They are building up a linear amino acid chain. The chain has a length of from 1 to 50 amino acids, preferred between 3 and 25 amino acids. The linker may contain repetitive amino acid sequences or parts of naturally occurring polypeptides, such as polypeptides with a hinge-function.

"Synthetic linkers" are designated to be rich in glycine, glutamine and serine residues. These residues are arranged in a small peptide unit of up to five amino acids, such as GGGGS, QQQQG or SSSSG. The small peptide unit is repeated for two to five times to form a multimeric unit. At each of the amino- and/or carboxy-terminal end of the multimeric unit up to six additional amino acids can be added.

The term "biologically active molecule" as used herein refers to an organic molecule, e.g. a biological macromolecule such as a peptide, protein, glycoprotein, nucleoprotein, muco-protein, lipoprotein, synthetic polypeptide or protein, that causes a biological effect when administered in or to artificial biological systems, such as bioassays using cell lines and viruses, or in vivo an animal, including but not limited to birds and mammals, including humans. This biological effect can be but is not limited to enzyme inhibition or activation, binding to a receptor or a ligand, either at the binding site or circumferential, signal triggering or signal modulation.

Biologically active molecules are without limitation for example hormones, cytokines, growth factors, receptor ligands, agonists or antagonists, cytotoxic agents, antiviral agents, imaging agents, enzyme inhibitors, enzyme activators or enzyme activity modulators such as allosteric substances.

The term "amino acid" as used within this application comprises alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

Methods and techniques known to a person skilled in the art, which are useful for carrying out the current invention, are described e.g. in Ausubel, F. M., ed., Current Protocols in Molecular Biology, Volumes I to III (1997), Wiley and Sons; Sambrook et al., Molecular Cloning: A Laboratory Manual, Second Edition, Cold Spring Harbor Laboratory Press, Cold Spring Harbor, N.Y. (1989).

The invention comprises a method for the recombinant production of a heterologous polypeptide in a eukaryotic host cell. The host cell comprises an expression plasmid, which comprises in 5' to 3' direction a) a promoter, b) a nucleic acid encoding a first polypeptide whose amino acid sequence is selected from Table 1 depending of the first two amino acids of the second polypeptide, c) a nucleic acid encoding a second polypeptide comprising a nucleic acid encoding a heterologous polypeptide having a biological activity, a nucleic acid encoding a peptide or polypeptide selected from the group consisting of SEQ ID NO: 06-10, 139, 140, and 554-557, a nucleic acid encoding an immunoglobulin fragment, and d) a 3' untranslated region. This expression plasmid is introduced into a host cell which is cultivated under conditions suitable for the expression of the second polypeptide. The secreted second polypeptide is recovered from the culture medium.

The first polypeptide is a so-called signal sequence. The signal sequence is responsible for the secretion of the attached/succeeding/operably linked polypeptide. To be effective the signal sequence has to be recognized and processed by the proteins and enzymes within the cell expressing the polypeptide. In case of a eukaryotic host cell, the signal sequence is preferably a eukaryotic one. To assure that the second polypeptide according to the current invention is secreted correctly, the signal sequence is selected from human and murine immunoglobulin signal sequences. A compilation is shown in table 1.

Which signal sequence is selected depends on the succeeding amino acids. It has to be assured that the signal peptidase, which cleaves the signal sequence after the secretion process, recognizes the signal sequence of the secreted polypeptide and removes it. To provide a "natural" transition from the signal sequence to the heterologous polypeptide the signal sequence should be chosen that way, that the first two amino acids of the heterologous polypeptide are identical to the first two amino acids of the amino acid sequences of the naturally following immunoglobulin FR1-region.

TABLE 1

Set of the first two amino acids (given in one letter code) of the second polypeptide assigned to signal peptides (first polypeptide given in one letter code).

| second polypeptide starts with amino acids | first peptide (signal sequence) amino acid sequence | SEQ ID NO: |
|---|---|---|
| AC | MEFQTQVLMSLLLCMS | 163 |
| | MESQTQVLMFLLLWVS | 164 |
| | MVSTPQFLVFLLFWIP | 165 |
| AD | MESQTLVFISILLWLY | 166 |
| AG | MSVPTQLLGLLLLWLT | 167 |
| AH | MKSQTQVFIFLLLCVS | 168 |
| | MKSQTQVFVFLLLCVS | 169 |
| AI | MDMRVPAQLLGLLLLWLRGARC | 68 |
| | MDMRVPAQLLGLLLLWLRGARC | 69 |
| | MDMRVPAQLLGLLQLWLSGARC | 70 |
| | MDMRVPAQLLGLLLLWLSGARC | 71 |
| | MDMRVPAQLLGLLLLWLPDTRC | 72 |
| | MDMRVPAQLLGLLLLWFPGARC | 73 |
| | MDMRVPAQLLGLLLLWFPGARC | 74 |
| | MDMRVLAQLLGLLLLCFPGARC | 75 |
| | MDMRVLAQLLGLLLLCFPGARC | 76 |
| | MDMRVPAQLLGLLLLWLPGARC | 77 |
| | MDMRVPAQLLGLLLLWLPGARC | 78 |
| | MDMRVPAQLLGLLLLWFPGSRC | 79 |
| | MDMRVPAQLLGLLLLWFPGSRC | 80 |
| | MDMRVPAQLLGLLLLWLPGARC | 81 |
| | MDMRVPAQRLGLLLLWFPGARC | 82 |
| | MRVPAQLLGLLLLWLPGARC | 83 |
| | MDMRVPAQLLGLLLLWLPGARC | 84 |
| | MDMRVPAQLLGLLLLWLPGARC | 85 |
| | MDMRVPAQLLGLLLLWLPGAKC | 86 |
| | MAWISLILSLLALSS | 170 |
| | MAWTSLILSLLALCS | 171 |
| | MRCLAEFLGLLVLWIP | 172 |
| AL | MGWNWIFILILSVTT | 173 |
| AQ | MRFQVQVLGLLLLWIS | 174 |
| | MRPSIQFLGLLLFWLH | 175 |
| AR | MDIRAPAQFLGILLLWFP | 176 |
| | MDMMVLAQFLAFLLLWFP | 177 |
| | MDMRAPAQFLGILLLWFP | 178 |
| | MDMRAPAQFLGILLLWFP | 179 |
| | MDMRAPAQVFGFLLLWFP | 180 |
| | MDMRASAQFHGILLLWFP | 181 |
| | MDMRASAQFHGILLLWFP | 182 |
| | MDMWTSAQFLGILLLWFL | 183 |
| | MNTRAPAEFLGFLLLWFL | 184 |
| | MRAPAPFLGLLLFCFL | 185 |
| | MRTPAPFLGLLLFCFS | 186 |
| | MSISTQLLGLLLLWLT | 187 |
| | MSLPTQLQGLLLLWLT | 188 |
| | MSVLTQVLALLLLWLT | 189 |
| | MSVPTQLLALLLLWLT | 190 |
| | MSVPTQVLGLLLLWLT | 191 |
| | TDFHMQIFSFMLISFT | 192 |
| AS | MAWTSLILSLLALCS | 193 |
| AT | MRCLAEFLRLLVLWIP | 194 |
| CQ | MPWALLLLTLLTHSAVSVV | 138 |
| DA | MKLPVRLLVLMFWIPSSS | 195 |
| DI | MDMRVPAQLLGLLLLWLRGARC | 68 |
| | MDMRVPAQLLGLLLLWLRGARC | 69 |
| | MDMRVPAQLLGLLQLWLSGARC | 70 |
| | MDMRVPAQLLGLLLLWLSGARC | 71 |
| | MDMRVPAQLLGLLLLWLPDTRC | 72 |
| | MDMRVPAQLLGLLLLWFPGARC | 73 |
| | MDMRVPAQLLGLLLLWFPGARC | 74 |
| | MDMRVLAQLLGLLLLCFPGARC | 75 |
| | MDMRVLAQLLGLLLLCFPGARC | 76 |
| | MDMRVPAQLLGLLLLWLPGARC | 77 |
| | MDMRVPAQLLGLLLLWLPGARC | 78 |
| | MDMRVPAQLLGLLLLWFPGSRC | 79 |
| | MDMRVPAQLLGLLLLWFPGSRC | 80 |
| | MDMRVPAQLLGLLLLWLPGARC | 81 |
| | MDMRVPAQRLGLLLLWFPGARC | 82 |
| | MRVPAQLLGLLLLWLPGARC | 83 |
| | MDMRVPAQLLGLLLLWLPGARC | 84 |
| | MDMRVPAQLLGLLLLWLPGARC | 85 |
| | MDMRVPAQLLGLLLLWLPGAKC | 86 |
| | MRLPAQLLGLLMLWVPGSSE | 87 |
| | MRLPAQLLGLLMLWVPGSSE | 88 |
| | MRLPAQLLGLLMLWVPGSSG | 89 |
| | MRLPAQLLGLLMLWVPGSSG | 90 |
| | MRLPAQLLGLLMLWIPGSSA | 91 |
| | MRLPAQLLGLLMLWIPGSSA | 92 |
| | MRLPAQLLGLLMLWVSGSSG | 93 |
| | MRLPAQLLGLLMLWVSGSSG | 94 |
| | MRLLAQLLGLLMLWVPGSSG | 95 |
| | MVLQTQVFISLLLWISGAYG | 103 |
| | MDIRAPAQFLGILLLWFPARC | 196 |
| | MDMMVLAQFLAFLLLWFPARC | 197 |
| | MDMRAPAQFFGILLLWFPIRC | 198 |
| | MDMRAPAQFLGILLLWFPARC | 199 |
| | MDMRAPAQIFGFLLLLFQTRC | 200 |
| | MDMRAPAQVFGFLLLWFPARC | 201 |
| | MDMRASAQFLGFLLLWFP | 202 |
| | MDMRDPPQFLAFLLLWIP | 203 |
| | MDMRTPAQFLGILLLWFPIKC | 204 |
| | MDMRVPAHVFGFLLLWFPTRC | 205 |
| | MDSQAQVLILLLLWVSTCG | 206 |
| | MDSQAQVLMLLLLSVSTCG | 207 |
| | MDSQAQVLMLLLLWVSTCG | 208 |
| | MDSQARVLMLLLLWVSTCG | 209 |
| | MEFQTQVFVFVLLWLSVDG | 210 |
| | MEFQTQVLMSLLLCMSACA | 211 |
| | MEKDTLLLWVLLLWVPSTG | 212 |
| | MESDTLLLWVLLLWVPSTG | 213 |
| | MESQIQAFVFVFLWLSVDG | 214 |
| | MESQIQVFVFVFLWLSVDG | 215 |
| | MESQNHVLMFLLLWVSTCG | 473 |
| | MESQTHVLMFLLLWVSTCG | 474 |
| | MESQTQVFVYMLLWLSVDG | 475 |
| | MESQTQVLISLLFWVSTCG | 476 |
| | MESQTQVLMFLLLWVSACA | 477 |
| | MESQTQVLMSLLFWVSTCG | 478 |
| | METDPLLLWVLLLWVPSTG | 479 |
| | METDTILLWVLLLWVPSTG | 480 |
| | METDTLLLWVLLLWVPSTG | 481 |
| | METDTLLLWVLLLWVPSTG | 482 |
| | METHSQVFVYMLLWLSVEG | 483 |
| | MGFKMESHTQAFVFAFLWLSVDG | 484 |
| | MGVPTQLLLLWLTVRC | 485 |
| | MIASAQFLGLLLLCFQTRC | 486 |
| | MKFPSQLLLFLLFRITIIC | 487 |
| | MKFPSQLLLLLLFGIPMIC | 488 |
| | MMSSAQFLGLLLLCFQTRC | 489 |
| | MMSSAQFLGLLLLCFQTRY | 490 |
| | MNMLTQLLGLLLLWFAGKC | 491 |
| | MRCLAEFLGLLVLWIPAIG | 492 |
| | MRCLAEFLRLLVLWIPATG | 493 |
| | MRCSLQFLGVLMFWISVSG | 494 |
| | MRFSAQLLGLLVLWIPSTA | 495 |
| | MRPSIQFLGLLLFWLHAQC | 496 |
| | MRVLAELLGLLLFCFLVRC | 497 |
| | MRVLPEFLGLLLLWISVRC | 498 |

TABLE 1-continued

Set of the first two amino acids (given in one letter code) of the second polypeptide assigned to signal peptides (first polypeptide given in one letter code).

| second polypeptide starts with amino acids | first peptide (signal sequence) amino acid sequence | SEQ ID NO: |
|---|---|---|
| | MSISTQLLGLLLLWLTARC | 499 |
| | MSVLTQVLALLLLWLTARC | 500 |
| | MSVPTQLLALLLLWLTARC | 501 |
| | MSVPTQLLGLLLLWLTAGC | 502 |
| | MSVPTQVLGLLLLWLTARC | 503 |
| | MVFTPQILGLMLFWISSTG | 504 |
| | MVFTPQILGLMLFWISSRG | 505 |
| | MVLGLKWVFFVVFYQSRG | 506 |
| | MVSTSQLLGLLLFWTSSRG | 507 |
| | PAQFLFLLVLWIQSRC | 508 |
| DR | MSLLTQLQGLLLLWLT | 216 |
| DV | MRLPAQLLGLLMLWVPGSSE | 87 |
| | MRLPAQLLGLLMLWVPGSSE | 88 |
| | MRLPAQLLGLLMLWVPGSSG | 89 |
| | MRLPAQLLGLLMLWVPGSSG | 90 |
| | MRLPAQLLGLLMLWIPGSSA | 91 |
| | MRLPAQLLGLLMLWIPGSSA | 92 |
| | MRLPAQLLGLLMLWVSGSSG | 93 |
| | MRLPAQLLGLLMLWVSGSSG | 94 |
| | MRLLAQLLGLLMLWVPGSSG | 95 |
| | MLPSQLIGFLLLWVPASRG | 105 |
| | MLPSQLIGFLLLWVPASRG | 106 |
| | MVSPLQFLRLLLLWVPASRG | 107 |
| | LILKVQC | 217 |
| | LVLKVLC | 218 |
| | MDMRASAQFHGILLLWFPARC | 219 |
| | MKLPVLLVVLLLFTSPSSS | 220 |
| | MKLPVRLLVLMFWIPSSS | 221 |
| | MMSPAQFLFLLVLWIQTNG | 222 |
| | MMSPAQFLFLLVLWIRTNG | 223 |
| | MMSPVHSIFILLLWIVISG | 224 |
| | MMSPVQFLFLLMLWIQTNG | 225 |
| | MNFGLRLIFLVLTLKVQC | 226 |
| | MNLPVHLLVLLLFWIPSRG | 227 |
| | MNTRAPAEFLGFLLLWFLARC | 228 |
| | MRFQVQVLGLLLLWISAQC | 229 |
| | MRVLSLLYLLTAIPGILS | 230 |
| EI | M ETPAQLLFLLLLWLPDTTG | 96 |
| | METPAQLLFLLLLWLPDTTG | 97 |
| | MEAPAQLLFLLLLWLPDTTG | 98 |
| | MEAPAQLLFLLLLWLPDTTG | 99 |
| | MEAPAQLLFLLLLWLPDTTG | 100 |
| | MEAPAQLLFLLLLWLTDTTG | 101 |
| | MEPWKPQHSFFFLLLLWLPDTTG | 102 |
| | MLPSQLIGFLLLWVPASRG | 105 |
| | MLPSQLIGFLLLWVPASRG | 106 |
| | MVSPLQFLRLLLLWVPASRG | 107 |
| | MDFHVQIFSFMLISVTILSSG | 231 |
| | MDFQMQIISLLLISVTIVSNG | 232 |
| | MDFQVQIFSFLLISVTILTNG | 233 |
| | MDMRAPAQFLGILLLWFPARC | 234 |
| | MNFHVQIFSFMLISVTIGSSG | 235 |
| | MTMLSLVLLLSFLLLCSRA | 236 |
| | MVSTPQFLVFLLFWIPACG | 237 |
| | TELICVFLFLLSVTAILSSG | 238 |
| EI | MDCGISLVFLVLILKVC | 239 |
| EM | MDMWVQIFSLLLICVTSKG | 240 |
| EN | LLISVTIMSRG | 241 |
| | MDFQVQIFSFLLISASIMSRG | 242 |
| | MDFQVQIFSFLLISISVMSRG | 243 |
| | MDFQVQIFSFLLISVSIMSRG | 244 |
| | MDLQVQIISFLLIIVTIMSRG | 245 |

TABLE 1-continued

Set of the first two amino acids (given in one letter code) of the second polypeptide assigned to signal peptides (first polypeptide given in one letter code).

| second polypeptide starts with amino acids | first peptide (signal sequence) amino acid sequence | SEQ ID NO: |
|---|---|---|
| ET | MGSQVHLLSFLLLWISDTRA | 104 |
| | MGEQRIRSCHATSGAESAR | 246 |
| | MGSQVHLLSFLLLWISDTRA | 247 |
| | MTMFSLALLLSLLLLCVSSRA | 248 |
| | MTMLSLAPLLSLLLLSRA | 249 |
| | MXTMDEHESGAVTPHQVLKSRA | 250 |
| EV | MDWTWRILFLVAAATGAHS | 28 |
| | MDWTWRILFLVAAATGAHS | 29 |
| | MDWTWRILFLVAAATSAHS | 30 |
| | MDWTWSILFLVAAPTGAHS | 31 |
| | MDCTWRILFLVAAATGTHA | 32 |
| | MDWTWRILFLVAAATDAYS | 33 |
| | MDWTWRVFCLLAVAPGAHS | 34 |
| | MDWIWRILFLVGAATGAHS | 35 |
| | MELGLSWVFLVAILEGVQC | 38 |
| | MELGLSWIFLLAILKGVQC | 39 |
| | MEFGLSWVFLVAIIKGVQC | 40 |
| | MELGLSWVFLVAILEGVQC | 41 |
| | MEFGLSWIFLAAILKGVQC | 42 |
| | MEFGLSWVFLVAILKGVQC | 43 |
| | MELGLRWVFLVAILEGVQC | 44 |
| | MEFGLSWLFLVAILKGVQC | 45 |
| | MEFGLSWVFLVALLRGVQC | 46 |
| | MEFGLSWVFLVALLRGVQC | 47 |
| | MEFGLSWVFLVAILKGVQC | 48 |
| | MELGLCWVFLVAILEGVQC | 49 |
| | MEFGLSWVFLVAILKGVQC | 50 |
| | MEFWLSWVFLVAILKGVQC | 51 |
| | MTEFGLSWVFLVAIFKGVQC | 52 |
| | MEFGLSWVFLVAILKGVQC | 53 |
| | MEFGLSWVFLVVILQGVQC | 54 |
| | MEFGLSWVFLVAILKGVQC | 55 |
| | MGSTAILALLLAVLQGVCS | 64 |
| | MGSTAILGLLLAVLQGVCA | 65 |
| | IKWSWIFLFLLSGTAVHS | 251 |
| | IKWSWISLFLLSGTAVHS | 252 |
| | LILKVQC | 253 |
| | LVLKVQC | 254 |
| | MAVVTGKGLPSPKLEVNS | 255 |
| | MDFGLIFFIVALLKVQC | 256 |
| | MDFGLSLVFLVLILKVQC | 257 |
| | MDMRASAQFHGILLLWFPARC | 258 |
| | MEWELSLIFIFALLKDVQC | 259 |
| | MEWSCIFLFLLSVTAVHS | 260 |
| | MEWSCIFLFLLSVTAIHS | 261 |
| | MEWSWIFLFLLSGTAVLS | 262 |
| | MGWNWIFILILSVTTALS | 263 |
| | MGWSCIILFLVATATVHS | 264 |
| | MGWNWIFILILSVTTVHS | 265 |
| | MGWSCIMLFLAATATVHS | 266 |
| | MGWSWIFFFLLSGTAVLS | 267 |
| | MGWSWIFLFFLSGTAVLS | 268 |
| | MGWSWIFLFLLSGSAVLS | 269 |
| | MGWSWIFLFLLSGSAVHS | 270 |
| | MGWSWIFLFLLSGTAVHS | 271 |
| | MGWSWIFLFLLSGTAVLS | 509 |
| | MGWSWIFLFLLSGTAVLS | 510 |
| | MGWSWIFLLFLSGTAVLS | 511 |
| | MGWSWIFLLFLSGTAVHS | 512 |
| | MGWSWIFLLFLSGTAVLS | 513 |
| | MGWSWVFLSFLSGTAVLS | 514 |
| | MKCSWVIFFLMAVVIINS | 515 |
| | MKLWLNWILLVALLNIQC | 516 |
| | MLLGLKWVFFVVFYQVHC | 517 |
| | MLLGLKWVFFVVFYQGVHC | 518 |
| | MMVLSLLYLLTALPGILS | 519 |
| | MNFGLSLIFLVLILKVQC | 520 |
| | MQLGHLLPDGSVNS | 521 |

TABLE 1-continued

Set of the first two amino acids (given in one letter code) of the second polypeptide assigned to signal peptides (first polypeptide given in one letter code).

| second polypeptide starts with amino acids | first peptide (signal sequence) amino acid sequence | SEQ ID NO: |
|---|---|---|
| | MVSETHVLIFLLLWVSVHC | 522 |
| | RSVPTQLLGLLLLWLTVNS | 523 |
| GH | MGWSYIILFLVATAT | 272 |
| GI | IDINVQIFRFLLISVTSSG | 273 |
| GK | MNMLTQLLGLLLLWFA | 274 |
| GR | MRTPAHFLGLLLLCFL | 275 |
| HV | MRWSCIILFLVATATVHS | 276 |
| IG | MNFHVQIFSFMLISVT | 277 |
| IH | MEWSCIFLFLLSVTA | 278 |
| II | MDFQVQIFQIPVKQCL | 279 |
| | MDFQVQIFSFLLISAS | 280 |
| | MKFPSQLLLFLLFRIT | 281 |
| IK | MDMRTPAQFLGILLLWFP | 282 |
| IL | MAVLALLFCLVTFPS | 283 |
| | MDFHVQIFSFMLISVT | 284 |
| | MDFQVQIFSFLLISAS | 285 |
| | MDFQVQIFSFLLISR | 286 |
| | MDFQVQIFSFLLISVT | 287 |
| | TELICVFLFLLSVTA | 288 |
| IM | LLISVT | 289 |
| | MDFQVQIFSFLLISAS | 290 |
| | MDFQVQIFSFLLISVS | 291 |
| | MDFQVQIFSFLLISVS | 292 |
| | MDFQVQIFSFLLMSAS | 293 |
| | MDLQVQIISFLLIIVT | 294 |
| | MHFQVQIFSFLLISAS | 295 |
| IN | MKCSWVIFFLMAVVI | 296 |
| IQ | MKLWLNWILLVALLN | 297 |
| IR | MDMRAPAQFFGILLLWFP | 298 |
| IS | MIYSLQLLRMLVLWIP | 299 |
| | MMSPVHSIFILLLWIV | 300 |
| | MSYSLQLLRMLVLWIP | 301 |
| IT | MSYSLQLLRMLVLWIP | 302 |
| IV | MDFQMQIISLLLISVT | 303 |
| KN | MDFQVQIFQIPVKQCLIISRG | 304 |
| LM | MDFQVQIFSFLLISAS | 305 |
| LP | MAWVSFYLLPFIFSTGLCA | 127 |
| | MAWTQLLLLFPLLLHWTGSLS | 128 |
| | MAWTPLLFLTLLLHCTGSLS | 129 |
| LR | MRPTLSFLGSCCSSLI | 306 |
| MI | MKFPSQLLLLLLFGIP | 307 |
| NF | MAW AP LLLTLLAHCTGSWA | 133 |
| NI | MDMRVPAQLLGLLLLWLRGARC | 68 |
| | MDMRVPAQLLGLLLLWLRGARC | 69 |
| | MDMRVPAQLLGLLQLWLSGARC | 70 |
| | MDMRVPAQLLGLLLLWLSGARC | 71 |

TABLE 1-continued

Set of the first two amino acids (given in one letter code) of the second polypeptide assigned to signal peptides (first polypeptide given in one letter code).

| second polypeptide starts with amino acids | first peptide (signal sequence) amino acid sequence | SEQ ID NO: |
|---|---|---|
| | MDMRVPAQLLGLLLLWLPDTRC | 72 |
| | MDMRVPAQLLGLLLLWFPGARC | 73 |
| | MDMRVPAQLLGLLLLWFPGARC | 74 |
| | MDMRVLAQLLGLLLLCFPGARC | 75 |
| | MDMRVLAQLLGLLLLCFPGARC | 76 |
| | MDMRVPAQLLGLLLLWLPGARC | 77 |
| | MDMRVPAQLLGLLLLWLPGARC | 78 |
| | MDMRVPAQLLGLLLLWFPGSRC | 79 |
| | MDMRVPAQLLGLLLLWFPGSRC | 80 |
| | MDMRVPAQLLGLLLLWLPGARC | 81 |
| | MDMRVPAQRLGLLLLWFPGARC | 82 |
| | MRVPAQLLGLLLLWLPGARC | 83 |
| | MDMRVPAQLLGLLLLWLPGARC | 84 |
| | MDMRVPAQLLGLLLLWLPGARC | 85 |
| | MDMRVPAQLLGLLLLWLPGAKC | 86 |
| | MESDTLLLWVLLLWVPSTS | 308 |
| | MESQTLVFISILLWLYADG | 309 |
| | MESQTQVFLSLLLWVSTCG | 310 |
| | METDTLLLWVLLLWVPSTG | 311 |
| PV | MGWSCIMLFLAATATVHS | 312 |
| | MGWSCIMLFLAATATGVHS | 313 |
| QA | MD M RVP AQ LLGLLLLWLRGARC | 68 |
| | MD M RVP AQ LLGLLLLWLRGARC | 69 |
| | MD M RVP AQ LLGLLQLWLSGARC | 70 |
| | MD M RVP AQ LLGLLLLWLSGARC | 71 |
| | MD M RVP AQ LLGLLLLWLPDTRC | 72 |
| | MD M RVP AQ LLGLLLLWFPGARC | 73 |
| | MD M RVP AQ LLGLLLLWFPGARC | 74 |
| | MD M RVL AQ LLGLLLLCFPGARC | 75 |
| | MD M RVL AQ LLGLLLLCFPGARC | 76 |
| | MD M RVP AQ LLGLLLLWLPGARC | 77 |
| | MD M RVP AQ LLGLLLLWLPGARC | 78 |
| | MD M RVP AQ LLGLLLLWFPGSRC | 79 |
| | MD M RVP AQ LLGLLLLWFPGSRC | 80 |
| | MD M RVP AQ LLGLLLLWLPGARC | 81 |
| | MD M RVP AQ RLGLLLLWFPGARC | 82 |
| | M RVP AQ LLGLLLLWLPGARC | 83 |
| | MD M RVP AQ LLGLLLLWLPGARC | 84 |
| | MD M RVP AQ LLGLLLLWLPGARC | 85 |
| | MD M RVP AQ LLGLLLLWLPGAKC | 86 |
| | MAW TP LLLLLLSHCTGSLS | 130 |
| | MAW TP LLLLFLSHCTGSLS | 131 |
| | MAW TL LLLVLLSHCTGSLS | 132 |
| | MAW TP LFLFLLTCCPGSNS | 134 |
| | MAW TP LFLFLLTCCPGSNS | 135 |
| | MAWISLILSLLALSSAIS | 314 |
| | IGWSYIILLLVATATVHS | 315 |
| | MAWTSLILSLLALCSASS | 316 |
| | MAWTSLILSLLALCSAIS | 317 |
| | MGWSCVLLFLVSGTAVLC | 318 |
| QI | MDT LC STLLLLTIPSWVLS | 36 |
| | MDT LC YTLLLLTTPSWVLS | 37 |
| | MDFQVQIFSFLLISASIISRG | 319 |
| | MDFQVQIFSFLLISASILFRG | 320 |
| | MDFQVQIFSFLLISASILSRG | 321 |
| | MDFQVQIFSFLLISASIMSRG | 322 |
| | MDFQVQIFSFLLISASLMSRG | 323 |
| | MDFQVQIFSFLLISRILSRG | 324 |
| | MDFQVQIFSFLLISVSIMSRG | 325 |
| | MDFQVQIFSFLLMSASIMSRG | 326 |
| | MDTLCSTLLLLTIPSWVLS | 327 |
| | MGWSWIFLFLLSGTAVHC | 328 |
| | MHFQVQIFSFLLISASIMSRG | 329 |
| QL | MKH LW FFLLLVAAPRWVLS | 56 |
| | MKH LW FFLLLVAAPRWVLS | 57 |
| | MKH LW FFLLLVAAPRWVLP | 58 |

TABLE 1-continued

Set of the first two amino acids (given in one letter code) of the second polypeptide assigned to signal peptides (first polypeptide given in one letter code).

| second polypeptide starts with amino acids | first peptide (signal sequence) amino acid sequence | SEQ ID NO: |
|---|---|---|
| | MKH LW FFLLLVAAPRWVLS | 59 |
| | MKH LW FFLLLVAAPRWVLS | 60 |
| | MKH LW FFLLLVAAPRWVLS | 61 |
| | MKH LW FFLLLVAAPRWVLS | 62 |
| | MKH LW FFLLLVAAPRWVLS | 63 |
| | MAW VS FYLLPFIFSTGLCA | 127 |
| | M A WTQ LL LLFPLLLHWTGSLS | 128 |
| | M AWT PL LFLTLLLHCTGSLS | 129 |
| | MAWTPLFFFFVLHCSSFS | 330 |
| QM | MDWTWRILFLVAAATGAHS | 28 |
| | MDWTWRILFLVAAATGAHS | 29 |
| | MDWTWRILFLVAAATSAHS | 30 |
| | MDWTWSILFLVAAPTGAHS | 31 |
| | MDCTWRILFLVAAATGTHA | 32 |
| | MDWTWRILFLVAAATDAYS | 33 |
| | MDWTWRVFCLLAVAPGAHS | 34 |
| | MDWIWRILFLVGAATGAHS | 35 |
| | MRVLGFLCLVTVLPGSLS | 331 |
| QP | MAWVSFYLLPFIFSTGLCA | 127 |
| | MAWTQLLLLFPLLLHWTGSLS | 128 |
| | MAWTPLLFLTLLLHCTGSLS | 129 |
| | MAWTPLLLLLLSHCTGSLS | 130 |
| | MAWTPLLLLFLSHCTGSLS | 131 |
| | MAWTLLLLVLLSHCTGSLS | 132 |
| | MAWAPLLLTLLSLLTGSLS | 137 |
| | MAWTPLFFFFLLHCSSFS | 332 |
| QS | MAWSPLFLTLITHCAGSWA | 108 |
| | MAWSPLLLTLLAHCTGSWA | 109 |
| | MASFPLLLTLLTHCAGSWA | 110 |
| | MAGFPLLLTLLTHCAGSWA | 111 |
| | MTCSPLLLTLLIHCTGSWA | 112 |
| | MAWALLLLTLLTQGTGSWA | 113 |
| | MAWALLLLSLLTQGTGSWA | 114 |
| | MAWALLLLTLLTQGTGSWA | 115 |
| | MAWALLLLTLLTQGTGSWA | 116 |
| | MAWALLLLTLLTQDTGSWA | 117 |
| QT | MAWTPLFLFLLTCCPGSNS | 134 |
| | MAWTPLFLFLLTCCPGSNS | 135 |
| | MAWMMLLLGLLAYGSGVDS | 136 |
| QV | MDWTWRILFLVAAATGAHS | 28 |
| | MDWTWRILFLVAAATGAHS | 29 |
| | MDWTWRILFLVAAATSAHS | 30 |
| | MDWTWSILFLVAAPTGAHS | 31 |
| | MDCTWRILFLVAAATGTHA | 32 |
| | MDWTWRILFLVAAATDAYS | 33 |
| | MDWTWRVFCLLAVAPGAHS | 34 |
| | MDWIWRILFLVGAATGAHS | 35 |
| | MDTLCSTLLLLTIPSWVLS | 36 |
| | MDTLCYTLLLLTTPSWVLS | 37 |
| | MELGLSWVFLVAILEGVQC | 38 |
| | MELGLSWIFLLAILKGVQC | 39 |
| | MEFGLSWVFLVAIIKGVQC | 40 |
| | MELGLSWVFLVAILEGVQC | 41 |
| | MEFGLSWIFLAAILKGVQC | 42 |
| | MEFGLSWVFLVAILKGVQC | 43 |
| | MELGLRWVFLVAILEGVQC | 44 |
| | MEFGLSWLFLVAILKGVQC | 45 |
| | MEFGLSWVFLVALLRGVQC | 46 |
| | MEFGLSWVFLVALLRGVQC | 47 |
| | MEFGLSWVFLVAILKGVQC | 48 |
| | MELGLCWVFLVAILEGVQC | 49 |
| | MEFGLSWVFLVAILKGVQC | 50 |
| | MEFWLSWVFLVAILKGVQC | 51 |
| | MTEFGLSWVFLVAIFKGVQC | 52 |
| | MEFGLSWVFLVAILKGVQC | 53 |
| | MEFGLSWVFLVVILQGVQC | 54 |
| | MEFGLSWVFLVAILKGVQC | 55 |
| | MKHLWFFLLLVAAPRWVLS | 56 |
| | MKHLWFFLLLVAAPRWVLS | 57 |
| | MKHLWFFLLLVAAPRWVLP | 58 |
| | MKHLWFFLLLVAAPRWVLS | 59 |
| | MKHLWFFLLLVAAPRWVLS | 60 |
| | MKHLWFFLLLVAAPRWVLS | 61 |
| | MKHLWFFLLLVAAPRWVLS | 62 |
| | MKHLWFFLLLVAAPRWVLS | 63 |
| | MSVSFLIFLPVLGLPWGVLS | 66 |
| | MDWTWRILFLVAAATGAHS | 67 |
| | IFLFLLSITAVHC | 333 |
| | KGGSCVSLFLVATANVHF | 334 |
| | MAVLALLFCLVTFPSILS | 335 |
| | MAVLGLLFCLVTFPSVLS | 336 |
| | MAVLGLLLCLVTFPSVLS | 337 |
| | MAWSWVFLFFLSVTTVHS | 338 |
| | MDWIWIMLHLLAATGIQS | 339 |
| | MECSWVFLFLLSLTAVHC | 340 |
| | MEFGLSWVFLVALLRGVQC | 341 |
| | MEWLXXFLLFLSLTAVHC | 342 |
| | MEWSGVFIFLLSVTAVHS | 343 |
| | MEWSGVFIFLLSVTAVYS | 524 |
| | MEWSRVFIFLLSVTAVHS | 525 |
| | MEWSWVFLFFLSVTTVHS | 526 |
| | MEWSWVFLFLLSLTSVHS | 527 |
| | MGRLTFSFLLLLPVPAVLS | 528 |
| | MGWSCIIFFLVATATVHF | 529 |
| | MGWSCIILFLVAAANVHS | 530 |
| | MGWSCIILFLVAAATVHS | 531 |
| | MGWSCIILFLVATATVHS | 532 |
| | MGWSCIILFLVATATVHS | 533 |
| | MGWSCIILFLVSTATVHS | 534 |
| | MGWSCIILILVAAATVHS | 535 |
| | MGWSCIILILVAAATVHS | 536 |
| | MGWSCIILILVAAATVQF | 537 |
| | MGWSCIMLFLAARATVHS | 538 |
| | MGWSCIMLFLAATATVHF | 539 |
| | MGWSCIMLFLAATATVHF | 540 |
| | MGWSCIMLFLAATATVHS | 541 |
| | MGWSCIMLFLAATATVHS | 542 |
| | MGWSCIMLFLAATATVHS | 543 |
| | MGWSFLPLFLAATATGVHS | 544 |
| | MGWSRIFLFLLSITAVHC | 545 |
| | MGWSSIILFLVATATVHS | 546 |
| | MGWSWIFPFLLSGTAVHC | 547 |
| | MGWSYIIFFLVATATVHF | 548 |
| | MGWSYIIFFLVATATVHS | 549 |
| | MGWSYIILFLVATATGHS | 550 |
| | MGWSYIILFLVATATVHS | 551 |
| | MGWSYIILFLVATATVNS | 552 |
| | MRWSCIILFLVATATVHS | 553 |
| SA | METPASFLCLLLLWTT | 344 |
| SF | MAWTPLFFFFLLHCS | 345 |
| | MAWTPLFFFFVLHCS | 346 |
| SI | MKSQTQVFIFLLLCVSAHG | 347 |
| | MKSQTQVFVFLLLCVSAHG | 348 |
| SK | MDMWVQIFSLLLICVT | 349 |
| SR | MXTMDEHESGAVTPHQVLK | 350 |
| | MGEQRIRSCHATSGAE | 351 |
| | MNLPVHLLVLLLFWIP | 352 |
| | MTMFSLALLLSLLLLCVS | 353 |
| | MTMLSLAPLLSLLLL | 354 |
| | MTMLSLVLLLSFLLLC | 355 |

TABLE 1-continued

Set of the first two amino acids (given in one letter code) of the second polypeptide assigned to signal peptides (first polypeptide given in one letter code).

| second polypeptide starts with amino acids | first peptide (signal sequence) amino acid sequence | SEQ ID NO: |
|---|---|---|
| | MVFTPQILGLMLFWIS | 356 |
| | MVLGLKWVFFVVFYQ | 357 |
| | MVSTSQLLGLLLFWTS | 358 |
| | PAQFLFLLVLWIQ | 359 |
| SS | MAWIPLFLGVLAYCTGSVA | 118 |
| | MAWTALLLSLLAHFTGSVA | 119 |
| | MAWTPLLLPLLTFCTVSEA | 120 |
| | MAWIPLLLPLLTLCTGSEA | 121 |
| | MAWTPLWLTLLTLCIGSVV | 122 |
| | MAWTVLLLGLLSHCTGSVT | 123 |
| | MAWATLLLPLLNLYTGSIA | 124 |
| | MAWIPLLLPLLTLCTGSEA | 125 |
| | MAWIPLLLPLLILCTVSVA | 126 |
| | IDINVQIFRFLLISVT | 360 |
| | MKLPVLLVVLLLFTSP | 361 |
| | MKLPVRLLVLMFWIP | 362 |
| | MKLPVRLLVLMFWIP | 363 |
| ST | MEKDTLLLWVLLLWVP | 364 |
| | MESDTLLLWVLLLWVP | 365 |
| | MESDTLLLWVLLLWVP | 366 |
| | METDPLLLWVLLLWVP | 367 |
| | METDTILLWVLLLWVP | 368 |
| | METDTLLLWVLLLWVP | 369 |
| | METDTLLLWVLLLWVP | 370 |
| | METDTLLLWVLLLWVP | 371 |
| | MRFSAQLLGLLVLWIP | 372 |
| | MVFTPQILGLMLFWIS | 373 |
| SY | MAWIPLFLGVLAYCTGSVA | 118 |
| | MAWTALLLSLLAHFTGSVA | 119 |
| | MAWTPLLLPLLTFCTVSEA | 120 |
| | MAWIPLLLPLLTLCTGSEA | 121 |
| | MAWTPLWLTLLTLCIGSVV | 122 |
| | MAWTVLLLGLLSHCTGSVT | 123 |
| | MAWATLLLPLLNLYTGSIA | 124 |
| | MAWIPLLLPLLTLCTGSEA | 125 |
| | MAWIPLLLPLLILCTVSVA | 126 |
| TC | MDSQAQVLILLLLWVS | 374 |
| | MDSQAQVLMLLLLSVS | 375 |
| | MDSQAQVLMLLLLWVS | 376 |
| | MDSQARVLMLLLLWVS | 377 |
| | MESQNHVLMFLLLWVS | 378 |
| | MESQTHVLMFLLLWVS | 379 |
| | MESQTQVFLSLLLWVS | 380 |
| | MESQTQVLISLLFWVS | 381 |
| | MESQTQVLMSLLFWVS | 382 |
| TG | METPASFLCLLLLWTTSAV | 383 |
| TN | QHGHEGLCSVSWVPVA | 384 |
| | MMSPAQFLFLLVLWIQ | 385 |
| | MMSPAQFLFLLVLWIR | 386 |
| | MMSPVQFLFLLMLWIQ | 387 |
| TR | MIASAQFLGLLLLCFQ | 388 |
| | MMSSAQFLGLLLLCFQ | 389 |
| | MMSSAQFLGLLLLCFQ | 390 |
| | MDMRAPAQIFGFLLLLFQ | 391 |
| | MDMRVPAHVFGFLLLWFP | 392 |
| VC | MDCGISLVFLVLILK | 393 |
| VD | MEFQTQVFVFVLLWLS | 394 |
| | MESQIQAFVFVFLWLS | 395 |
| | MESQIQVFVFVFLWLS | 396 |
| | MESQTQVFVYMLLWLS | 397 |
| | MGFKMESHTQAFVFAFLWLS | 398 |
| VE | METHSQVFVYMLLWLS | 399 |
| VH | MEWLXXFLLFLSLTA | 400 |
| | MEWSCIFLFLLSVTA | 401 |
| | MEWSGVFIFLLSVTA | 402 |
| | MEWSRVFIFLLSVTA | 403 |
| | MEWSWVFLFFLSVTT | 404 |
| | MEWSWVFLFLLSLTS | 405 |
| | MGWNWIFILILSVTT | 406 |
| | MGWSCIIFFLVATAT | 407 |
| | MGWSCIILFLVAAAN | 408 |
| | MGWSCIILFLVAAAT | 409 |
| | MGWSCIILFLVATAT | 410 |
| | MGWSCIILFLVATAT | 411 |
| | MGWSCIILFLVATAT | 412 |
| | MGWSCIILFLVSTAT | 413 |
| | MGWSCIILILVAAAT | 414 |
| | MGWSCIILILVAAAT | 415 |
| | MGWSCIMLFLAARAT | 416 |
| | MGWSCIMLFLAATAT | 417 |
| | MGWSCIMLFLAATAT | 418 |
| | MGWSCIMLFLAATAT | 419 |
| | MGWSCIMLFLAATAT | 420 |
| | MGWSCIMLFLAATAT | 421 |
| | MGWSCIMLFLAATAT | 422 |
| | MGWSCIMLFLAATAT | 423 |
| | MGWSRIFLFLLSITA | 424 |
| | MGWSSIILFLVATAT | 425 |
| | MGWSWIFLFLLSGSA | 426 |
| | MGWSWIFLFLLSGTA | 427 |
| | MGWSWIFLFLLSGTA | 428 |
| | MGWSWIFLLFLSGTA | 429 |
| | MGWSWIFPFLLSGTA | 430 |
| | MGWSYIIFFLVATAT | 431 |
| | MGWSYIIFFLVATAT | 432 |
| | MGWSYIILFLVATAT | 433 |
| | MGWSYIILFLVATAT | 434 |
| | MGWSYIILFLVATAT | 435 |
| | MLLGLKWVFFVVFYQ | 436 |
| | MRWSCIILFLVATAT | 437 |
| | MRWSCIILFLVATAT | 438 |
| | MVSETHVLIFLLLWVS | 439 |
| | IFLFLLSITA | 440 |
| | IGWSYIILLLVATAT | 441 |
| | IKWSWIFLFLLSGTA | 442 |
| | IKWSWISLFLLSGTA | 443 |
| | KGGSCVSLFLVATAN | 444 |
| | MAWSWVFLFFLSVTT | 445 |
| | MECSWVFLFLLSLTA | 446 |
| VI | MDMRVPAQLLGLLLLWLRGARC | 68 |
| | MDMRVPAQLLGLLLLWLRGARC | 69 |
| | MDMRVPAQLLGLLQLWLSGARC | 70 |
| | MDMRVPAQLLGLLLLWLSGARC | 71 |
| | MDMRVPAQLLGLLLLWLPDTRC | 72 |
| | MDMRVPAQLLGLLLLWFPGARC | 73 |
| | MDMRVPAQLLGLLLLWFPGARC | 74 |
| | MDMRVLAQLLGLLLLCFPGARC | 75 |
| | MDMRVLAQLLGLLLLCFPGARC | 76 |
| | MDMRVPAQLLGLLLLWLPGARC | 77 |
| | MDMRVPAQLLGLLLLWLPGARC | 78 |
| | MDMRVPAQLLGLLLLWFPGSRC | 79 |
| | MDMRVPAQLLGLLLLWFPGSRC | 80 |
| | MDMRVPAQLLGLLLLWLPGARC | 81 |
| | MDMRVPAQRLGLLLLWFPGARC | 82 |
| | MRVPAQLLGLLLLWLPGARC | 83 |
| | MDMRVPAQLLGLLLLWLPGARC | 84 |
| | MDMRVPAQLLGLLLLWLPGARC | 85 |
| | MDMRVPAQLLGLLLLWLPGAKC | 86 |

TABLE 1-continued

Set of the first two amino acids (given in one letter code) of the second polypeptide assigned to signal peptides (first polypeptide given in one letter code).

| second polypeptide starts with amino acids | first peptide (signal sequence) amino acid sequence | SEQ ID NO: |
|---|---|---|
| | MIYSLQLLRMLVLWIPISK | 447 |
| | MSYSLQLLRMLVLWIPISK | 448 |
| | MSYSLQLLRMLVLWIPITK | 449 |
| VL | LVLK | 450 |
| | MAVLGLLFCLVTFPS | 451 |
| | MAVLGLLLCLVTFPS | 452 |
| | MDRLTSSFLLLIVPA | 453 |
| | MEWSWIFLFLLSGTA | 454 |
| | MGRLTFSFLLLLPVPA | 455 |
| | MGWSCVLLFLVSGTA | 456 |
| | MGWSWIFFFLLSGTA | 457 |
| | MGWSWIFLFFLSGTA | 458 |
| | MGWSWIFLFLLSGSA | 459 |
| | MGWSWIFLFLLSGTA | 460 |
| | MGWSWIFLFLLSGTA | 461 |
| | MGWSWIFLLFLSGTA | 462 |
| | MGWSWIFLLFLSGTA | 463 |
| | MGWSWVFLSFLSGTA | 464 |
| VM | MDFQVQIFSFLLISIS | 465 |
| VN | MAVVTGKGLPSPKLE | 466 |
| | MGWSYIILFLVATAT | 467 |
| | MQLGHLLPDGS | 468 |
| | RSVPTQLLGLLLLWLT | 469 |
| VQ | LILK | 470 |
| | LVLK | 471 |
| | MDFGLIFFIVALLK | 141 |
| | MDFGLSLVFLVLILK | 02 |
| | MGWSCIILILVAAAT | 05 |
| | MNFGLRLIFLVLTLK | 20 |
| | MNFGLSLIFLVLILK | 21 |
| VR | MGVPTQLLLLWLT | 22 |
| | MRVLAELLGLLLFCFL | 23 |
| | MRVLPEFLGLLLLWIS | 24 |
| VS | MRCSLQFLGVLMFWIS | 25 |
| | REWSWNFLFLLSGTT | 26 |
| VY | MEWSGVFIFLLSVTA | 27 |
| if the combination of the first two amino acids of the second poly-peptide is not listed in this table these first polypeptides may be used | ELWVLMVWVP | 142 |
| | ELWVLMVWVPSTS | 143 |
| | HDHALTSSSPQPSSPLCL | 144 |
| | LAVITSNIWFPMVCMS | 145 |
| | MDMWTSAQFLGILLLWFLARC | 146 |
| | MDRLTSSFLLLIVPAVLS | 147 |
| | MLRAIKAAPFSRFGCS | 148 |
| | MRAPAPFLGLLLFCFLARC | 149 |
| | MRCSPHFLELLVFWIL | 150 |
| | MRPTLSFLGSCCSSLILRC | 151 |
| | MRTPAHFLGLLLLCFLGRC | 152 |
| | MRTPAPFLGLLLFCFSARC | 153 |
| | MSLLTQLQGLLLLWLTDRC | 154 |
| | MSLPTQLQGLLLLWLTARC | 155 |
| | MTMLSLAPLLSLLLLCVS | 156 |
| | MTSLSQLLGMLMLQSL | 157 |
| | MVFAPQILGFLLLWIS | 158 |
| | MVFTPHILGLLLFWIS | 159 |
| | QHGHEGLCSVSWVPVATNS | 160 |
| | REWSWNFLFLLSGTTVSS | 161 |
| | TDFHMQIFSFMLISFTARC | 162 |

If the dipeptide of the first two amino acids of the second polypeptide is not explicitly listed in Table 1, and no sequence as listed in the last row of Table 1 is intended to be used, it is beneficial not to string the first polypeptide and the second polypeptide directly together. In such a case it is favorable to insert a short sequence of up to five amino acids to resemble the beginning of the immunoglobulin FR1 region sequence which would naturally follow the first polypeptide. This sequence can be a single amino acid or a dipeptide, the peptide QIWNN (SEQ ID NO: 472) or a fragment thereof to resemble the first two amino acids of the naturally following immunoglobulin FR1 region.

After the first polypeptide or optionally after the inserted short sequence the second polypeptide comprises a heterologous polypeptide. This heterologous polypeptide has an amino acid sequence of from 5 to 500 amino acid residues. In a preferred embodiment of the invention the amino acid sequence is of from 10 to 350 amino acid residues and in a more preferred embodiment of from 15 to 150 amino acid residues. The polypeptide conjugated to the immunoglobulin is selected from the group comprising biological active molecules. These molecules exhibit a biological effect when administered to an artificial biological system or a living cell, such as in assay-systems, or to a living organism, such as birds or mammals, including humans. These biologically active compounds comprise, but are not limited to, agonists as well as antagonists of receptors, inhibitors as well as activators of enzymes, and the like, and also peptides, polypeptides, and proteins exhibiting cytotoxic, antiviral, antibacterial, or anticancer activity, as well as antigens. The biological effect can be, but is not limited, to enzyme inhibition, binding to a receptor, either at the binding site or circumferential, and signal triggering. These biologically active compounds are, for example, useful for pharmaceutic, therapeutic, or diagnostic applications.

The second polypeptide further comprises after the heterologous polypeptide a linker. Linkers that can preferably be used with the current invention are listed in Table 2.

TABLE 2

Possible linkers.

| linker | linker amino acid sequence | SEQ ID NO: |
|---|---|---|
| 1 | $[Ser(Gly)_4]_3$ | 06 |
| 2 | $[Ser(Gly)_4]_5$ | 07 |
| 3 | $[Gly(Gln)_4]_3$ | 08 |
| 4 | $Gly(Ser)_{15}Gly$ | 09 |
| 5 | GST | 10 |
| 6 | $[(Gly)_4Ser]_3$-Gly-Ala-Ser | 139 |
| 7 | $Gly(Ser)_{15}$Gly-Ala-Ser | 140 |
| 8 | $[(Gly)_4Ser]_3$-Gly | 554 |
| 9 | $[(Gly)_4Ser]_5$-Gly | 555 |
| 10 | $[(Gly)_4Ser]_3$-$Gly_2$ | 556 |
| 11 | $[(Gly)_4Ser]_5$-$Gly_2$ | 557 |

After the linker an immunoglobulin fragment follows as the carboxy-terminal part of the second polypeptide.

The second polypeptide comprises a heterologous polypeptide followed by a linker and followed by an immunoglobulin fragment as carboxy-terminal part, i.e. a nucleic acid encoding the second polypeptide comprises in a 5' to 3' direction nucleic acids encoding a heterologous polypeptide, a linker, and an immunoglobulin fragment.

Immunoglobulin molecules are assigned to five different classes: IgA (Immunoglobulin A), IgD, IgE, IgG and IgM. Of these IgG and IgE are more frequently used in pharmaceutic and diagnostic applications. Within these classes the immunoglobulins differ in their overall structure but the building blocks are similar. All immunoglobulins are built up of two different polypeptide chains, a light chain and a heavy chain.

An immunoglobulin fragment comprises the carboxy-terminal constant domain(s) of an immunoglobulin light or heavy chain, e.g. it comprises either at least the $C_H1$-, $C_H2$-, $C_H3$-domain and the hinge-region of an immunoglobulin heavy chain and optionally a $C_H4$-domain, or the $C_L$-domain of an immunoglobulin light chain. The immunoglobulin from which the fragment is derived can be a naturally occurring or a synthetic immunoglobulin. In one embodiment of the invention the immunoglobulin fragment additionally contains a fragment of a heavy or light chain variable domain or of a variant thereof. In the variable domain fragment amino acid(s) or region(s) are deleted. In one embodiment of from one to six amino acids of the variable domain are deleted. In another embodiment of from one to six regions of the variable domain are deleted. In a further embodiment the variable domain is deleted. The presence of a functional, i.e. antigen recognizing, variable domain is not essential for the current invention. A not functionable immunoglobulin according to the invention is an immunoglobulin not possessing an antigen recognizing variable domain.

The different nucleic acid sequences are operably linked on an expression plasmid. For expression the plasmid is introduced into a host cell. Proteins are preferably produced in mammalian cells such as CHO cells, NS0 cells, Sp2/0 cells, COS cells, HEK cells, K562 cells, BHK cells, PER.C6 cells, and the like.

The following examples, sequence listing and figures are provided to aid the understanding of the present invention, the true scope of which is set forth in the appended claims. It is understood that modifications can be made in the procedures set forth without departing from the spirit of the invention.

EXAMPLES

Material & Methods

Figure 1:
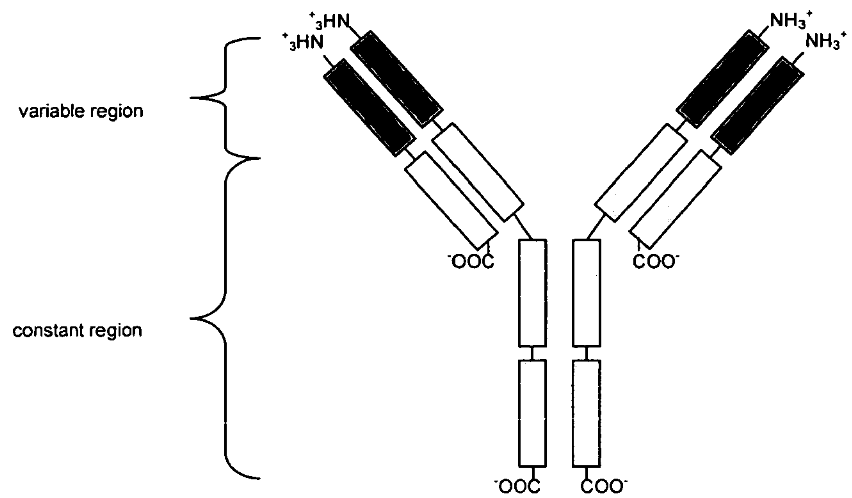
FIG. 1 Common structure of immunoglobulins of the IgG class.
Figure 1:
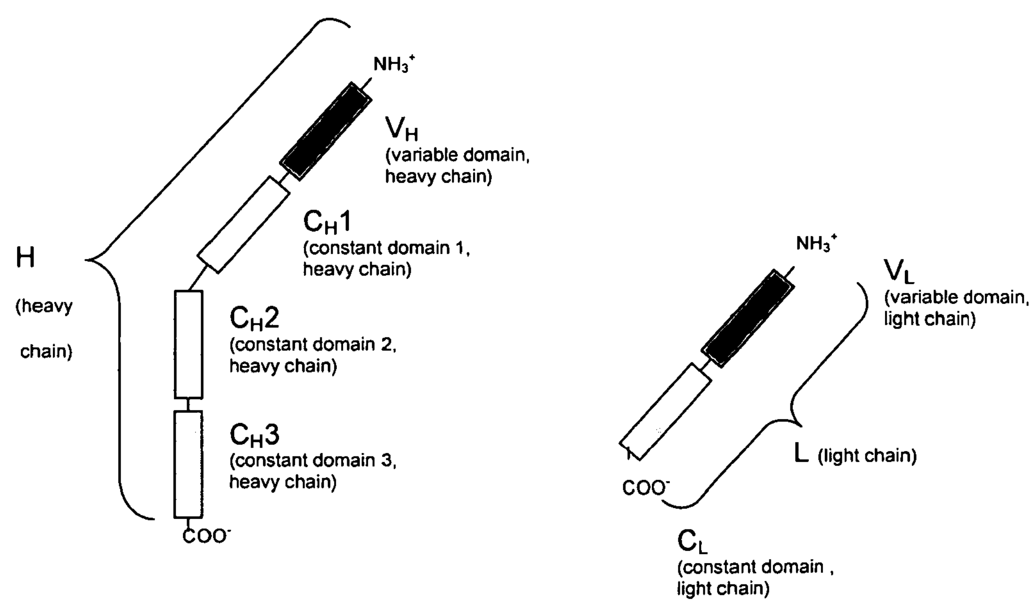

General information regarding the nucleotide sequences of human immunoglobulins light and heavy chains is given in: Kabat, E. A. et al., (1991) Sequences of Proteins of Immunological Interest, Fifth Ed., NIH Publication No 91-3242.

Amino acids of antibody chains are numbered according to EU numbering (Edelman, G. M., et al., *Proc Natl Acad Sci USA* 63 (1969) 78-85; Kabat, E. A., et al., (1991) Sequences of Proteins of Immunological Interest, Fifth Ed., NIH Publication No 91-3242).

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Protein Determination

The protein concentration was determined by determining the optical density (OD) at 280 nm, using the molar extinction coefficient calculated on the basis of the amino acid sequence.

DNA Sequence Determination

DNA sequences were determined by double strand sequencing performed at MediGenomix GmbH (Martinsried, Germany).

DNA and Protein Sequence Analysis and Sequence Data Management

The GCG's (Genetics Computer Group, Madison, Wis.) software package version 10.2 and Infomax's Vector NTI Advance suite version 8.0 was used for sequence creation, mapping, analysis, annotation and illustration.

Gene Synthesis

Desired gene segments were prepared by Medigenomix GmbH (Martinsried, Germany) from oligonucleotides made by chemical synthesis. The 100-600 bp long gene segments which are flanked by singular restriction endonuclease cleavage sites were assembled by annealing and ligation of oligonucleotides including PCR amplification and subsequently cloned into the pCR2.1-TOPO-TA cloning vector (Invitrogen Corp., USA) via A-overhangs. The DNA sequence of the subcloned gene fragments were confirmed by DNA sequencing.

Affinity Purification of Immunoglobulin Conjugates

The expressed and secreted immunoglobulin conjugates were purified by affinity chromatography using Protein A-Sepharose™ CL-4B (GE Healthcare, formerly Amersham Bioscience, Sweden) according to known methods. Briefly, after centrifugation (10,000 g for 10 minutes) and filtration through a 0.45 μm filter the immunoglobulin conjugate containing clarified culture supernatants were applied on a Protein A-Sepharose™ CL-4B column equilibrated with PBS buffer (10 mM $Na_2HPO_4$, 1 mM $KH_2PO_4$, 137 mM NaCl and 2.7 mM KCl, pH 7.4). Unbound proteins were washed out with PBS equilibration buffer and 0.1 M citrate buffer, pH 5.5. The immunoglobulin conjugates were eluted with 0.1 M citrate buffer, pH 3.0 and the immunoglobulin conjugate containing fractions were neutralized with 1 M Tris-Base. Then, the immunoglobulin conjugates were extensively dialyzed against PBS buffer at 4° C., concentrated with a ultrafree centrifugal filter device equipped with a Biomax-SK membrane (Millipore Corp., USA) and stored in an ice-water bath at 0° C.

Example 1

Making of the Expression Plasmids

The gene segments encoding an insulin-like growth factor I receptor (IGF-1R) antibody light chain variable region ($V_L$) and the human kappa-light chain constant region ($C_L$) were joined as were gene segments for the anti-IGF-1R heavy chain variable region ($V_H$) and the human gamma1-heavy chain constant region ($C_H$1-Hinge-$C_H$2-$C_H$3).

a) Vector 4818

Vector 4818 is the expression plasmid for the transient expression of anti-IGF-1R antibody (also denoted as anti-IGF-1R in the following) heavy chain (genomically organized expression cassette; exon-intron organization) in HEK293 EBNA cells (for sequences see US 2005/0008642). It comprises the following functional elements:

Beside the anti-IGF-1R γ1-heavy chain expression cassette this vector contains:

- a hygromycin resistance gene as a selectable marker,
- an origin of replication, oriP, of Epstein-Barr virus (EBV),
- an origin of replication from the vector pUC18 which allows replication of this plasmid in *E. coli*, and
- a beta-lactamase gene which confers ampicillin resistance in *E. coli*.

The transcription unit of the anti-IGF-1R gamma1-heavy gene is composed of the following elements:

- the immediate early enhancer and promoter from the human cytomegalovirus (HCMV),
- a synthetic 5'-untranslated region (UT),
- a murine immunoglobulin heavy chain signal sequence including a signal sequence intron (signal sequence 1, intron, signal sequence 2 [L1-intron-L2]),
- the cloned anti-IGF-1R variable heavy chain encoding segment arranged with a unique BsmI restriction site at the 5'-end (L2 signal sequence) and a splice donor site and a unique NotI restriction site at the 3'-end,
- a mouse/human heavy chain hybrid intron 2 including the mouse heavy chain enhancer element (part $JH_3$, $JH_4$) (Neuberger, M. S., *EMBO J.* 2 (1983) 1373-1378),
- the genomic human γ1-heavy gene constant region,
- the human γ1-immunoglobulin polyadenylation ("poly A") signal sequence, and
- the unique restriction sites AscI and SgrAI at the 5'- and 3'-end, respectively.

Figure 2:
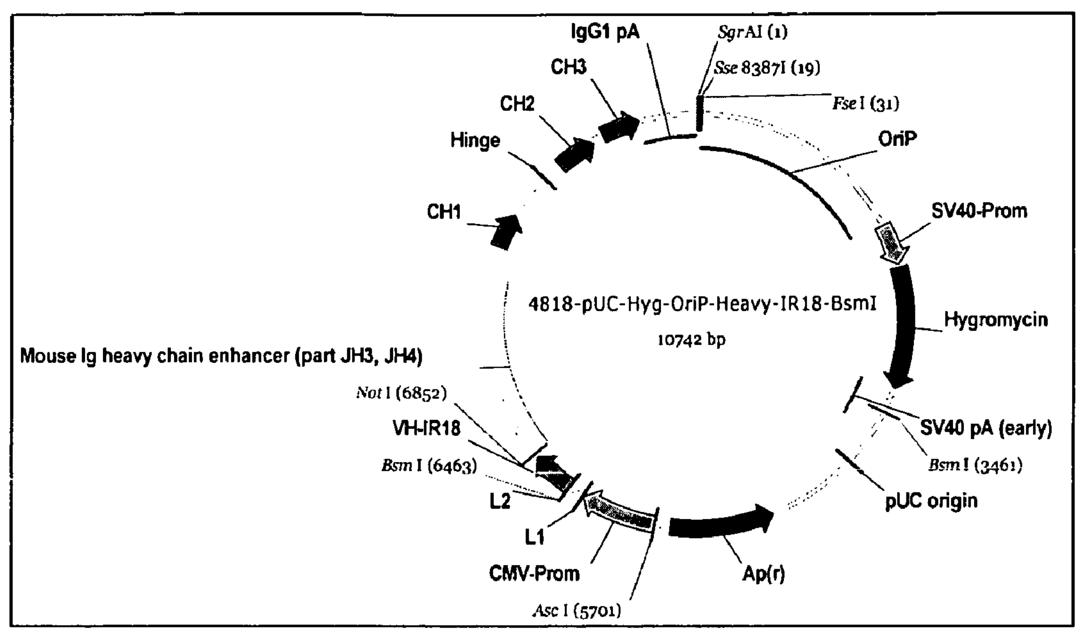
FIG. 2 Plasmid map of the anti-IGF-1R γ1-heavy chain expression vector 4818.

The plasmid map of the anti-IGF-1R γ1-heavy chain expression vector 4818 is shown in FIG. 2.

b) Vector 4802

Vector 4802 is the expression plasmid for the transient expression of anti-IGF-1R antibody light chain (cDNA) in HEK293 EBNA cells. It comprises the following functional elements.

Beside the anti-IGF-1R kappa-light chain expression cassette this vector contains:

- a hygromycin resistance gene as a selectable marker, a an origin of replication, oriP, of Epstein-Barr virus (EBV),
- an origin of replication from the vector pUC18 which allows replication of this plasmid in *E. coli*, and
- a β-lactamase gene which confers ampicillin resistance in *E. coli*.

The transcription unit of the anti-IGF-1R κ-light gene is composed of the following elements:

- the immediate early enhancer and promoter from the human cytomegalovirus (HCMV),
- the cloned anti-IGF-1R variable light chain cDNA including
- the native 5'-UT and
- the native light chain signal sequence of the human immunoglobulin germline gene arranged with a unique BglII restriction site at the 5'-end,
- the human κ-light gene constant region,
- the human immunoglobulin κ-polyadenylation ("poly A") signal sequence, and
- the unique restriction sites AscI and FseI at the 5'- and 3'-end, respectively.

Figure 3:
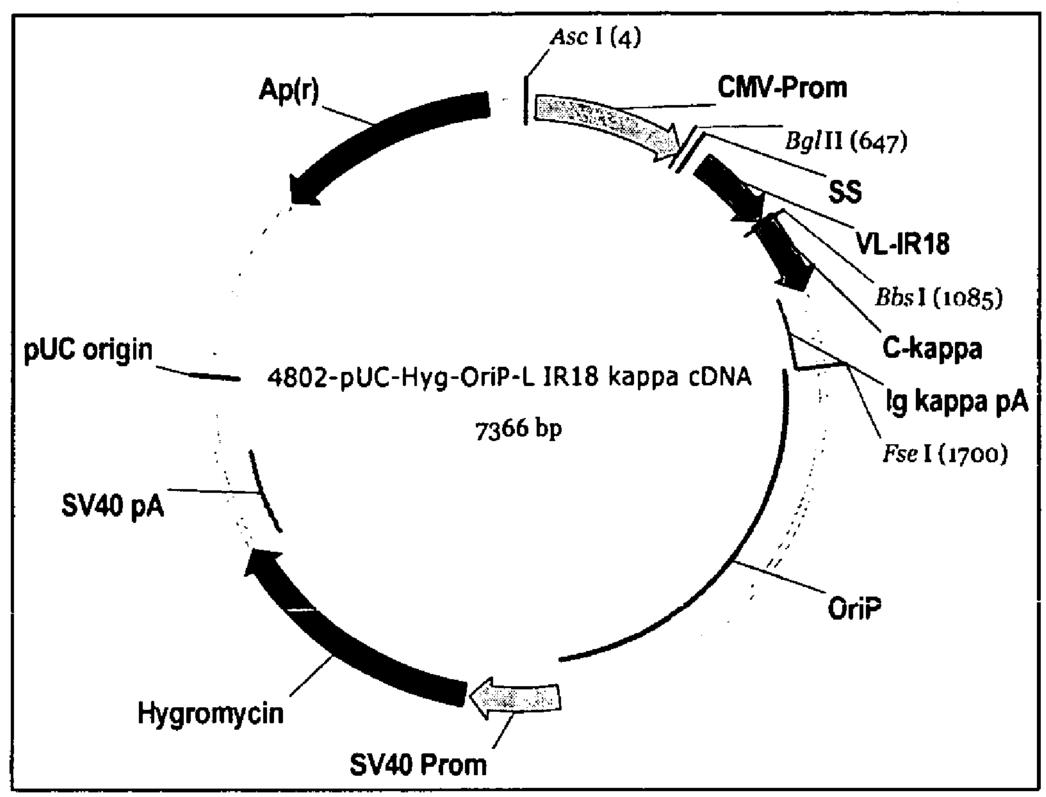
FIG. 3 Plasmid map of the anti-IGF-1R κ-light chain expression vector 4802.

The plasmid map of the anti-IGF-1R κ-light chain expression vector 4802 is shown in FIG. 3.

c) Plasmid 4962

Vector 4962 served as basic structure for the assembling of expression plasmids 4965, 4966 and 4967. These plasmids enabled the transient expression of modified antibody heavy chains (N-terminal conjugation without variable domain, cDNA organization) in HEK 293 EBNA cells. Plasmid 4962 comprises the following functional elements.

Beside the expression cassette for the gamma 1-heavy chain constant region this vector contains:

- a hygromycin resistance gene as a selectable marker,
- an origin of replication, oriP, of Epstein-Barr virus (EBV),
- an origin of replication from the vector pUC18 which allows replication of this plasmid in *E. coli*, and
- a beta-lactamase gene which confers ampicillin resistance in *E. coli*.

The transcription unit of the γ1-heavy chain constant region gene ($C_H$1-Hinge-$C_H$2-$C_H$3) is composed of the following elements:

- the immediate early enhancer and promoter from the human cytomegalovirus (HCMV),
- a synthetic linker (SEQ ID NO: 01) comprising a single BglII restriction site at the 5'-end and a single NheI restriction site at the 3'-end (NheI site within the $C_H$1 N-terminus)

```
HCMV-promoter                  AlaSer(CH1)
             ...agatctttgccaccgctagc...
                BglII          NheI
```

- the human γ1-heavy chain gene constant region ($C_H$1-Hinge-$C_H$2-$C_H$3, cDNA organization),
- the human γ1-immunoglobulin polyadenylation ("poly A") signal sequence, and
- the unique restriction sites AscI and FseI at the 5'- and 3'-end, respectively.

Figure 4:
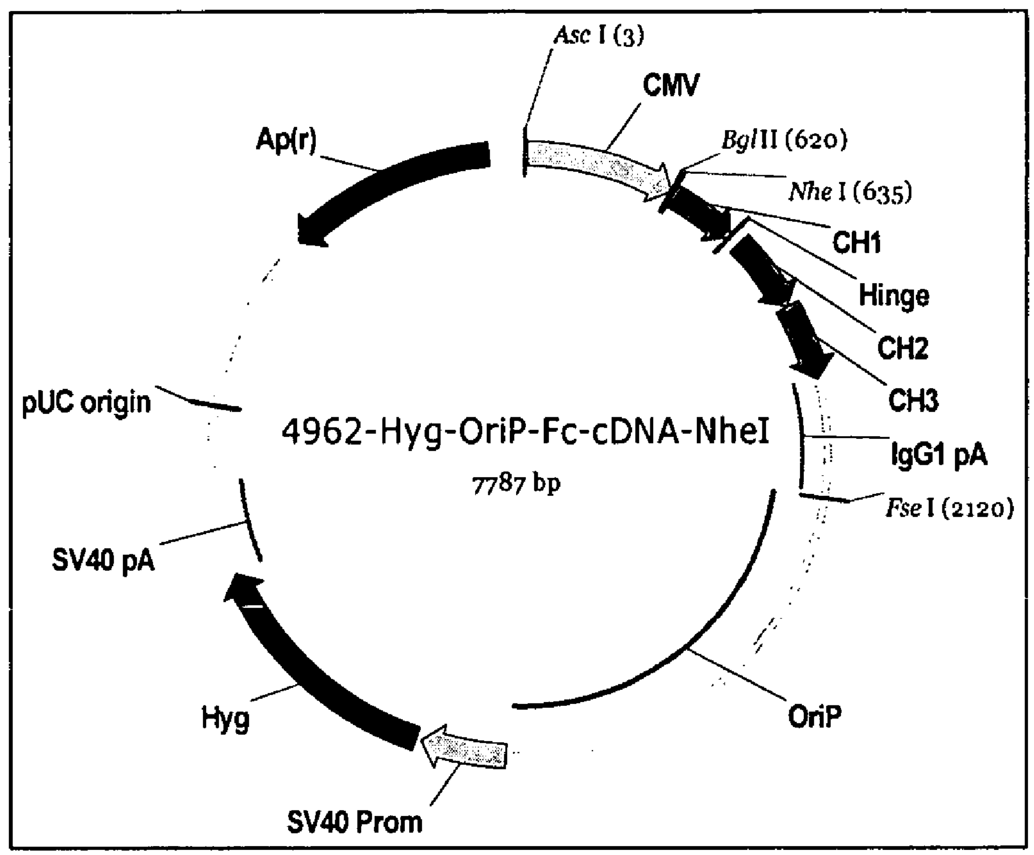
FIG. 4 Plasmid map of the γ1-heavy chain constant region gene vector 4962.

The plasmid map of the γ1-heavy chain constant region gene vector 4962 is shown in FIG. 4.

d) Plasmid 4964

Vector 4964 served as basic structure for the assembling of expression plasmids 4976 and 4977. These plasmids enabled the transient expression of modified anti-IGF-1R antibody light chains (N-terminal conjugation) in HEK 293 EBNA cells.

The plasmid 4964 is a variant of expression plasmid 4802.

The transcription unit of the anti-IGF-1R κ-light gene was modified as indicated below:

The native light chain signal sequence is replaced by a synthetic linker arranged with a unique BglII restriction site at the 5'- and a unique NheI restriction site at the 3'-end directly joined to the $V_L$-IGF-1R variable region (SEQ ID NO: 03).

```
                        |- V_L-1R18
...agatctatatatatatatgctagcgaaattgtgttgaca...
                     AlaSerGluIleValLeuThr...
   BglII             NheI
```

Figure 5:
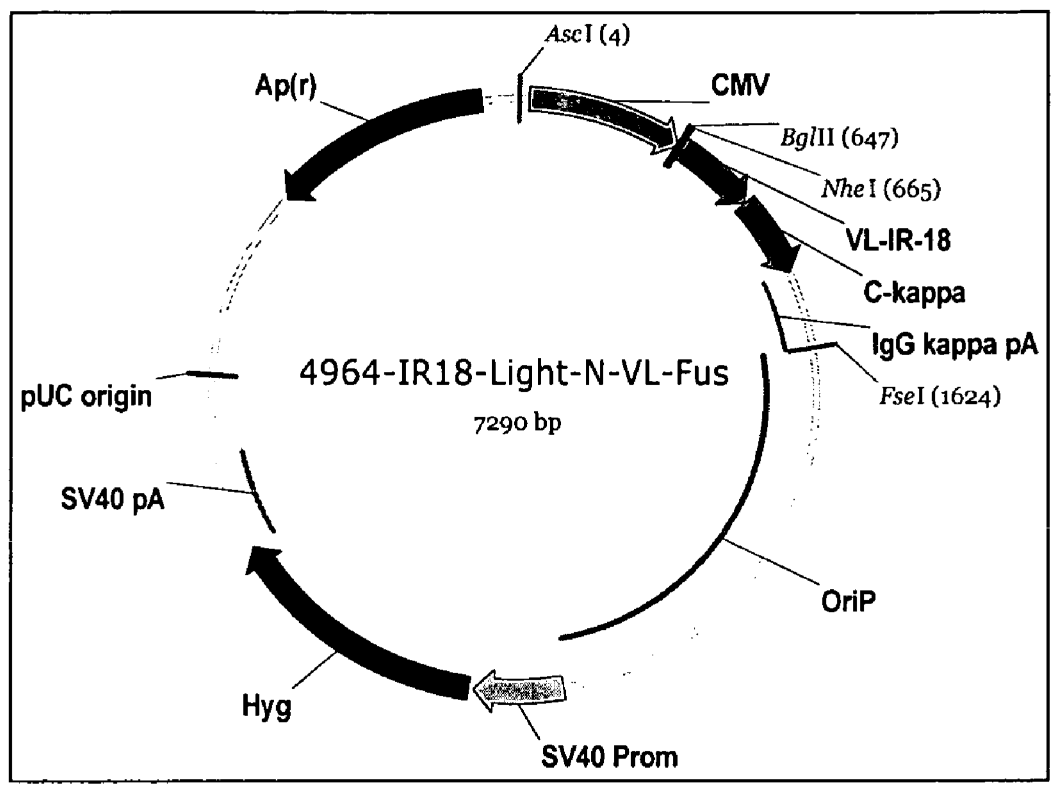
FIG. 5 Plasmid map of the modified anti-IGF-1R κ-light chain expression vector 4964.

The plasmid map of the modified anti-IGF-1R κ-light chain expression vector 4964 is shown in FIG. 5.

e) Plasmid 4969

The expression plasmid 4969 is derived from plasmid 4802 which is an expression plasmid for the anti-IGF-1R antibody light chain. The plasmid encodes a modified antibody light chain fragment (N-terminal conjugation without variable domain; polypeptide-linker-constant region of kappa chain).

For the construction of plasmid 4969 a unique BglII restriction site was introduced at the 3'-end of the CMV-promoter and a unique BbsI restriction site was introduced inside of the constant region of the anti-IGF-1R antibody light chain (SEQ ID NO: 04).

```
|--  C-kappa          BbsI
cgaactgtggctgcaccatctgtcttcatcttc...
ArgThrValAlaAlaProSerValPheIlePhe...
```

f) Plasmid 4963

This plasmid enabled the transient expression of anti-IGF-1R antibody light chains in HEK 293 EBNA cells.

The plasmid 4963 is a variant of expression plasmid 4802.

The transcription unit of the anti-IGF-1R κ-light gene was modified as indicated below:

the human κ-light chain constant gene region was slightly modified at the C-kappa-Ig-kappa pA joining region (insertion of a unique HindIII and KasI restriction site, SEQ ID NO: 558).

```
...C-kappa                       Ig-kappa-pA
...AaaagcttcaacaggggagagtgtTGAagggagaggcgcccccca
...LysSerPheAsnArgGlyGluCys
   HindIII                              KasI
```

Figure 6:
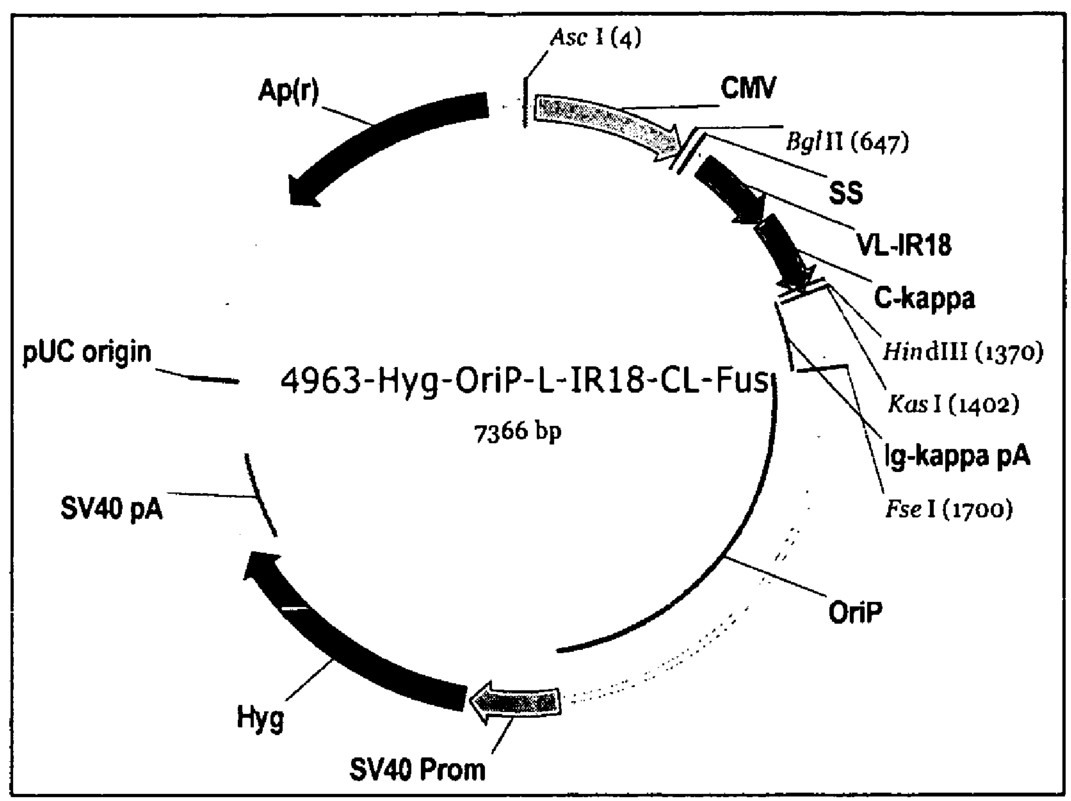
FIG. 6 Plasmid map of the modified anti-IGF-1R light chain expression vector 4963.

The plasmid map of the modified anti-IGF-1R light chain expression vector 4963 is shown FIG. 6.

Example 2

Making the Final Expression Plasmids

The immunoglobulin fusion genes (heavy and light chain) comprising the immunoglobulin gene segment, linker gene segment and polypeptide gene segment have been assembled with known recombinant methods and techniques by connection of the according gene segments.

The nucleic acid sequences encoding the peptide linkers and polypeptides were each synthesized by chemical synthesis and then ligated into an *E. coli* plasmid. The subcloned nucleic acid sequences were verified by DNA sequencing.

The employed immunoglobulin polypeptide chains, the immunoglobulin fragment, the location of the polypeptide conjugation (N-terminal), the employed linker and the employed polypeptide are listed in Table 2 (page 30), Table 3 and Table 3a.

TABLE 3

Employed proteins and polypeptides; the amino acid sequence and the numbering of the positions is as in the BH8 reference strain (Locus HIVH3BH8; HIV-1 isolate LAI/IIIB clone BH8 from France; Ratner, L., et al., Nature 313 (1985) 277-384).

| proteins and polypeptides | SEQ ID NO: |
|---|---|
| HIV-1 gp41 (position 507-851 of BH8 gp 160) | 11 |
| T-651 (see e.g. U.S. Pat. No. 6,656,906) | 12 |
| HIV-1 gp41 ectodomain variant single mutant: I568P | 13 |
| HIV-1 gp41 ectodomain variant quadruple mutant: I568P, L550E, L566E, I580E | 14 |

TABLE 3a

Chemically prepared gene segments used for immunoglobulin conjugate gene construction.

| Insert | SEQ ID NO: |
|---|---|
| Insert 4964 (introduction of unique restriction sites) | 15 |
| Insert 4965 (with T-651) comprising signal sequence (MDTLCSTLLLLTIPSWVLS), inserted short sequence (QIWNN), heterologous polypeptide (MTWMEWDREINNYTSLIHSLIEESQNQQEKNEQELL), linker (GGGGSGGGGSGGGGSG) | 16 |
| Insert 4966 (with T-651) comprising signal sequence (MDTLCSTLLLLTIPSWVLS), inserted short sequence (QIWNN), heterologous polypeptide (MTWMEWDREINNYTSLIHSLIEESQNQQEKNEQELL, linker (GGGGSGGGGSGGGGSGGGGSGGGGSG) | 17 |
| Insert 4967 (with T-651) comprising signal sequence (MDTLCSTLLLLTIPSWVLS), inserted short sequence (QIWNN), heterologous polypeptide (MTWMEWDREINNYTSLIHSLIEESQNQQEKNEQELL), linker (GSSSSSSSSSSSSSSG) | 18 |
| Insert 4969 (gp41 single mutant) comprising signal peptide (MEFGLSWVFLVALLRGVQC), inserted short sequence (Q), heterologous polypeptide (VQARQLLSGIVQQQNNLLRAIEGQQHLLQLTVWGPKQLQARIL AVERYLKDQQLLGIWGCSGKLICTTAVPWNASWSNKSLEQIWNN MTWMEWDREINNYTSLIHSLIEESQNQQEKNEQELL), linker (GGGGSGGGGSGGGGSG) | 19 |

The components used for the construction of the final expression plasmids for transient expression of the modified immunoglobulin polypeptide light and heavy chains (the expression cassettes) are listed in Table 4 with respect to the used basis plasmid, cloning site, and inserted nucleic acid sequence encoding the conjugated immunoglobulin polypeptides.

TABLE 4

Components employed in the construction of the used expression plasmids.

| Expression plasmid | Basis vector | Inserted DNA gene segment | Cloning sites |
|---|---|---|---|
| N-terminal conjugation: Heavy chain (without variable domain) | | | |
| 4965 | 4962 | Insert 4965 (249 Bp) | BglII/NheI |
| 4966 | 4962 | Insert 4966 (279 Bp) | BglII/NheI |
| 4967 | 4962 | Insert 4967 (252 Bp) | BglII/NheI |

TABLE 4-continued

| Components employed in the construction of the used expression plasmids. | | | |
|---|---|---|---|
| Expression plasmid | Basis vector | Inserted DNA gene segment | Cloning sites |
| N-terminal conjugation: Light chain (without variable domain) | | | |
| 4969 | 4802 | Insert 4969 (589 Bp) | BglII/BbsI |
| N-terminal conjugation: Light chain (including the variable domain) | | | |
| 4976 | 4964 | Insert 4965 (249 Bp) | HindIII/KasI |
| 4977 | 4964 | Insert 4967 (252 Bp) | HindIII/KasI |

In Table 5 is listed: the used polypeptides with HIV-1 inhibitory properties (T-651 and HIV-1 gp41 ectodomain variants), the used linkers to join the immunoglobulin light or heavy chain with the polypeptide and the deduced molecular weight of the modified antibody chains as deduced from the encoded amino acid sequences.

TABLE 5

| Summary of the employed polypeptides and the deduced molecular weight of the modified immunoglobulin polypeptide chains. | | | |
|---|---|---|---|
| expression plasmid | polypeptide | molecular weight [Da] | linker SEQ ID NO: |
| Reference plasmids | | | |
| 4818 | anti-IGF-1R heavy chain | 49263.5 | no linker |
| 4802 | anti-IGF-1R light chain | 23572.2 | no linker |
| N-terminal fusions: Heavy chain (without variable domain) | | | |
| 4965 | T-651 | 42227.3 | 554 |
| 4966 | T-651 | 42857.9 | 555 |
| 4967 | T-651 | 42644.7 | 09 |
| N-terminal fusions: Light chain (without variable domain) | | | |
| 4969 | Gp41 single mutant | 27247.3 | 554 |
| N-terminal fusions: Light chain (including the variable domain) | | | |
| 4976 | T-651 | 29851.9 | 139 |
| 4977 | T-651 | 30269.2 | 140 |

Example 3

Transient Expression of Immunoglobulin Variants in HEK293 EBNA Cells

Recombinant immunoglobulin variants were generated by transient transfection of adherent growing K293-EBNA cells (human embryonic kidney cell line 293 expressing Epstein-Barr-Virus nuclear antigen; American type culture collection deposit number ATCC # CRL-10852) cultivated in DMEM (Dulbecco's modified Eagle's medium, Gibco, Invitrogen Corp., USA) supplemented with 10% ultra-low IgG FCS (fetal calf serum, Gibco, Invitrogen Corp., USA), 2 mM Glutamine (Gibco, Invitrogen Corp., USA), 1% volume by volume (v/v) nonessential amino acids (Gibco, Invitrogen Corp., USA) and 250 μg/ml G418 (Roche Molecular Biochemicals, Roche Diagnostics GmbH, Germany). For transfection Fugene™ 6 Transfection Reagent (Roche Molecular Biochemicals, Roche Diagnostics GmbH, Germany) was used in a ratio of reagent (μl) to DNA (μg) ranging from 3:1 to 6:1. Immunoglobulin polypeptide light and heavy chains were expressed from two different plasmids using a molar ratio of light chain to heavy chain encoding plasmid from 1:2 to 2:1. Immunoglobulin variants containing cell culture supernatants were harvested at day 4 to 11 after transfection. Supernatants were stored at 0° C. in an ice-water bath until purification.

General information regarding the recombinant expression of human immunoglobulins in e.g. HEK293 cells is given in: Meissner, P. et al., *Biotechnol. Bioeng.* 75 (2001) 197-203.

Example 4

Expression Analysis Using SDS Page, Western Blotting Transfer and Detection with Immunoglobulin Specific Antibody Conjugates The expressed and secreted polypeptides were processed by sodium dodecyl sulfate (SDS) polyacrylamide gel electrophoresis (SDS-PAGE), and the separated polypeptides were transferred to a membrane from the gel and subsequently detected by an immunological method.

SDS-PAGE

LDS sample buffer, fourfold concentrate (4×): 4 g glycerol, 0.682 g Tris-Base, 0.666 g Tris-hydrochloride, 0.8 g LDS (lithium dodecyl sulfate), 0.006 g EDTA (ethylene diamine tetra-acetic acid), 0.75 ml of a 1% by weight (w/w) solution of Serva Blue G250 in water, 0.75 ml of a 1% by weight (w/w) solution of phenol red, add water to make a total volume of 10 ml.

The culture broth containing the secreted polypeptide was centrifuged to remove cells and cell debris. An aliquot of the clarified supernatant was admixed with 1/4 volumes (v/v) of 4×LDS sample buffer and 1/10 volume (v/v) of 0.5 M 1,4-dithiothreitol (DTT). Then the samples were incubated for 10 min. at 70° C. and protein separated by SDS-PAGE. The NuPAGE® Pre-Cast gel system (Invitrogen Corp., USA) was used according to the manufacturer's instruction. In particular, 10% NuPAGE® Novex® Bis-Tris Pre-Cast gels (pH 6.4) and a NuPAGE® MOPS running buffer was used.

Western Blot

Transfer buffer: 39 mM glycine, 48 mM Tris-hydrochloride, 0.04% by weight (w/w) SDS, and 20% by volume methanol (v/v)

After SDS-PAGE the separated immunoglobulin conjugate polypeptide chains were transferred electrophoretically to a nitrocellulose filter membrane (pore size: 0.45 μm) according to the "Semidry-Blotting-Method" of Burnette (Burnette, W. N., Anal. Biochem. 112 (1981) 195-203).

Immunological Detection

TBS-buffer: 50 mM Tris-hydrochloride, 150 mM NaCl, adjusted to pH 7.5

Blocking solution: 1% (w/v) Western Blocking Reagent (Roche Molecular Biochemicals, Roche Diagnostics GmbH, Germany) in TBS-buffer TBST-Buffer: 1×TBS-buffer with 0.05% by volume (v/v) Tween-20

For immunological detection the western blotting membranes were incubated with shaking at room temperature two times for 5 minutes in TBS-buffer and once for 90 minutes in blocking solution.

Detection of the Immunoglobulin Conjugate Polypeptide Chains

Heavy chain: For detection of the heavy chain or heavy chain fragment containing polypeptides a purified rabbit anti-human IgG antibody conjugated to a peroxidase was used (Code No. P 0214, DAKO, Denmark).

Light chain: Polypeptides containing light chain or light chain fragments were detected with a purified peroxidase conjugated rabbit anti-human kappa light chain antibody (DAKO, Denmark, Code No. P 0129).

For visualization of the antibody light and heavy chains or fragments thereof washed and blocked Western blot membranes were first incubated in case of a heavy chain with a purified rabbit anti-human IgG antibody conjugated to a peroxidase or in case of a light chain with a purified peroxidase conjugated rabbit anti-human kappa light chain antibody in a 1:10,000 dilution in 10 ml blocking solution at 4° C. with shaking over night. After washing the membranes three times with TBTS-buffer and once with TBS buffer for 10 min. at room temperature. The Western-blot membranes were developed with a Luminol/peroxid-solution generating chemi-luminescence (Lumi-Light$^{PLUS}$ Western Blotting Substrate, Roche Molecular Biochemicals, Roche Diagnostics GmbH, Germany). Therefore the membranes were incubated in 10 ml Luminol/peroxide-solution for 10 seconds to 5 minutes and the emitted light was detected afterwards with a Lumi-Imager F1 Analysator (Roche Molecular Biochemicals, Roche Diagnostics GmbH, Germany) and/or was recorded with an x-ray-film.

The intensity of the spots was quantified with the Lumi-Analyst Software (Version 3.1).

Multiple-Staining of Immunoblots

The secondary peroxidase-labeled antibody conjugate used for the detection can be removed from the stained blot by incubating the membrane for one hour at 70° C. in 1 M Tris-hydrochloride-buffer (pH 6.7) containing 100 mM beta-mercaptoethanol and 20% (w/v) SDS. After this treatment the blot can be stained with a different secondary antibody a second time. Prior to the second detection the blot is washed three times at room temperature with shaking in TBS-buffer for 10 minutes each.

The sample arrangement is listed in table 6.

TABLE 6

Sample arrangement of SDS PAGE gels/Western blots

| sample | expression plasmids light chain | expression plasmids heavy chain | note |
|---|---|---|---|
| MW marker | | | |
| anti-IGF-1R (reference Ab), 50 ng | | | |
| anti-IGF-1R (reference Ab), 150 ng | | | |
| anti-IGF-1R (reference Ab), 500 ng | | | |
| HEK293 culture medium | | | |
| 3 | 4802 (wt) | 4818 (wt) | anti-IGF-1R (reference Ab) control |
| 4 | 4802 (wt) | 4961 (wt) | anti-IGF-1R (reference Ab) control |
| 5 | 4963 (wt) | 4818 (wt) | anti-IGF-1R (reference Ab) control |
| 6 | 4802 (wt) | 4965 | N-term; heavy; without VH |
| 7 | 4802 (wt) | 4966 | N-term; heavy; without VH |
| 8 | 4802 (wt) | 4967 | N-term; heavy; without VH |
| 9 | 4969 | 4818 (wt) | N-term; light; without VL |
| 10 | 4976 | 4818 (wt) | N-term; light |
| 11 | 4977 | 4918 (wt) | N-term; light |
| 12 | 4969 | 4966 | N-term; light; without VL N-term; heavy; without VH |
| 13 | 4976 | 4966 | N-term; light; N-term; heavy; without VH |
| 14 | 4977 | 4967 | N-term; light N-term; heavy; without VH |

Example 5

Detection of Assembled Immunoglobulin Polypeptides

Purification and Concentration of Immunoglobulin Polypeptides by Affinity Binding to Protein A Sepharose™ CL-4B HEK 293 EBNA cells containing one or more plasmids were cultivated under conditions suitable for the transient expression of the polypeptide gene(s) located on the plasmid (s) for 6 to 10 days. To 1 ml clarified culture supernatant in a 1.8 ml Eppendorf cup 0.1 ml of a Protein A Sepharose™ CL-4B (GE Healthcare, formerly Amersham Biosciences, Sweden) suspension (1:1 (v/v) suspension of Protein A Sepharose in PBS buffer (10 mM $Na_2HPO_4$, 1 mM $KH_2PO_4$, 137 mM NaCl and 2.7 mM KCl, pH 7.4)) was added. The suspension was incubated for a time of between one and sixteen hours at room temperature with shaking. Thereafter the Sepharose beads were sedimented by centrifugation (30 s, 5000 rpm) and the supernatant was discarded. The Sepharose pellet was washed subsequently each with 1.6 ml PBS buffer, 1.6 ml 0.1 M citrate buffer pH 5.0 and 1.6 ml distilled water. The protein A bound immunoglobulin was extracted from the Sepharose beads with 0.1 ml 1×LDS-PAGE sample buffer at 70° C. for 5 to 10 min. The analysis was done by SDS-PAGE separation and staining with Coomassie brilliant blue as described in example 4.

Figure 7A:
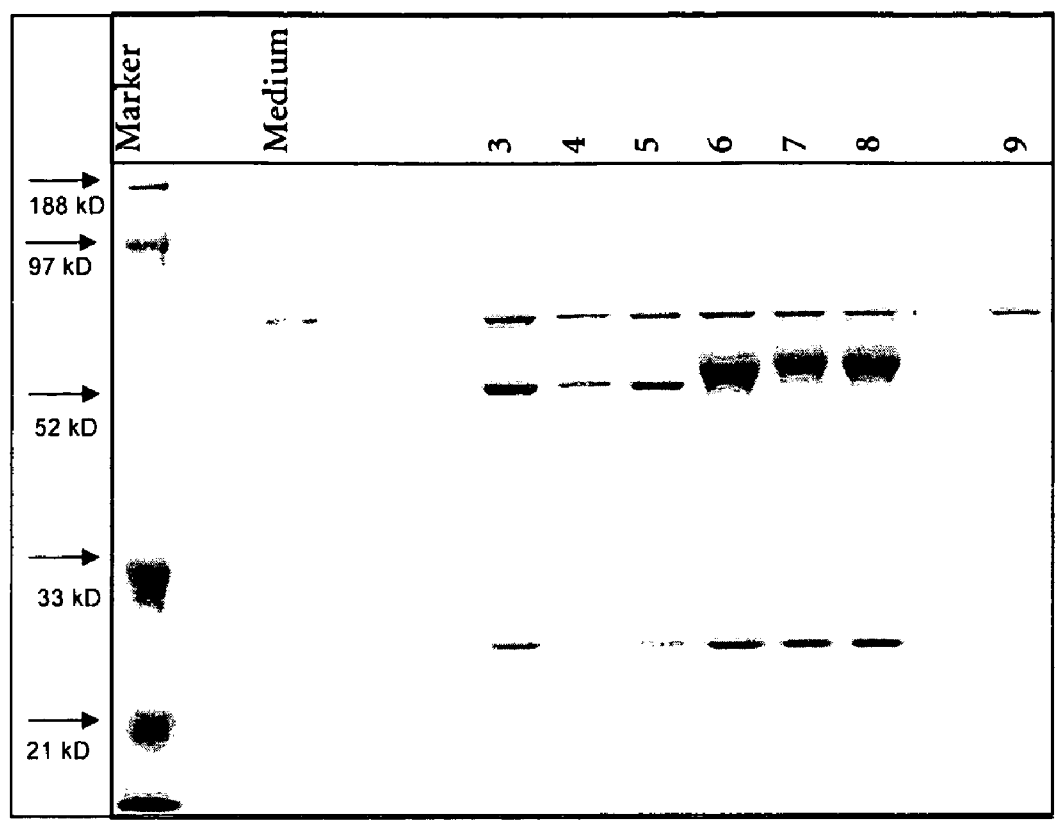
FIGS. 7*a*, 7*b*, and 7*c* Coomassie Blue stained SDS-PAGE-gels of affinity purified immunoglobulin conjugates; sample arrangement according to table 6.
Figure 7B:
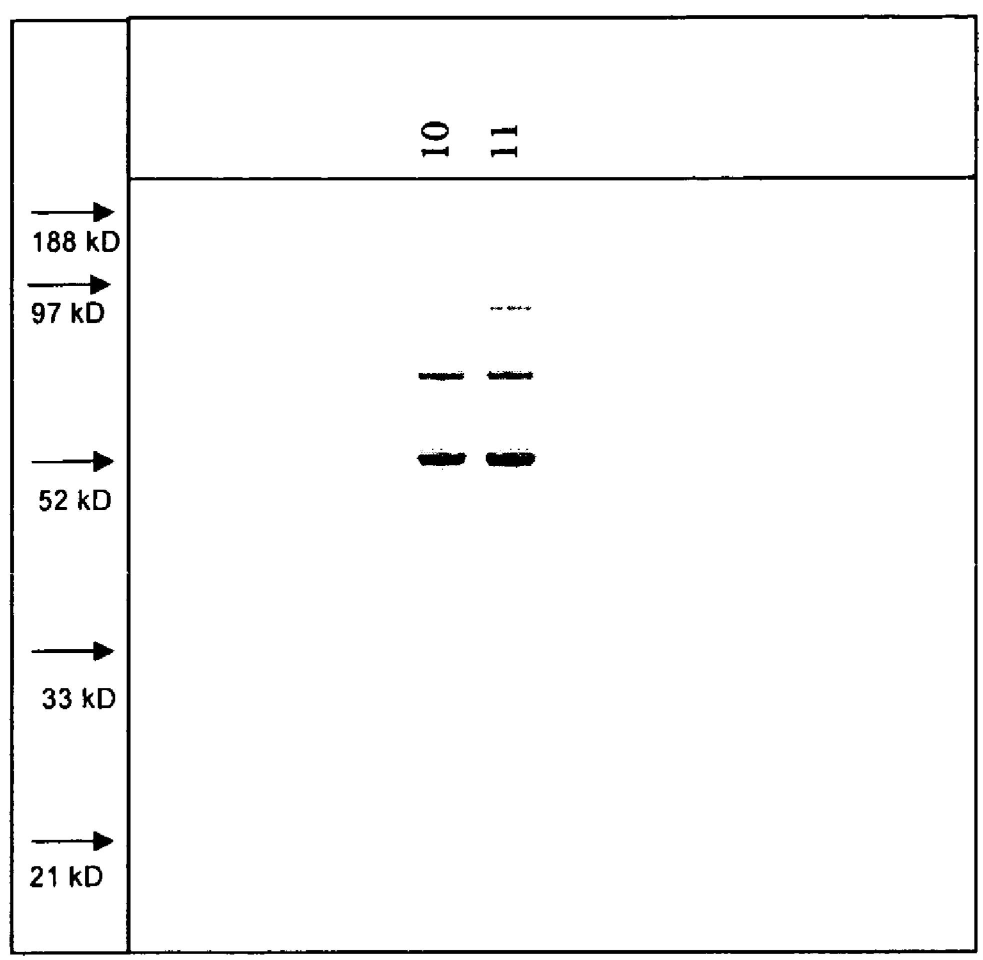
Figure 7C:
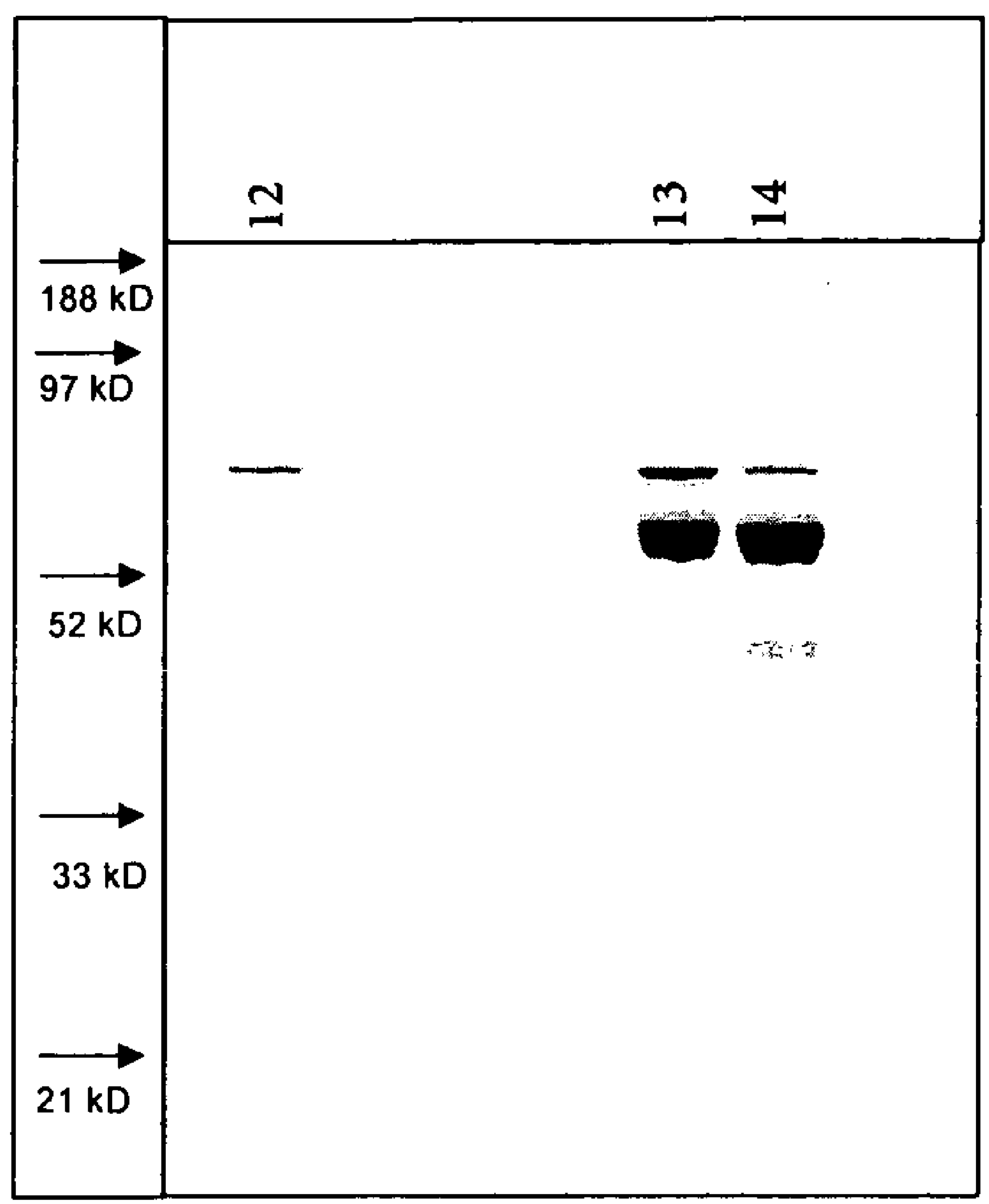

Results:

Expression/Secretion-Analysis of Heavy and/or Light Chain Fragment Containing Polypeptides After Transient Expression:

FIG. 7*a-c*: Coomassie Blue stained SDS-PAGE-gels of affinity purified polypeptides; sample arrangement according to table 6.

Figure 8A:
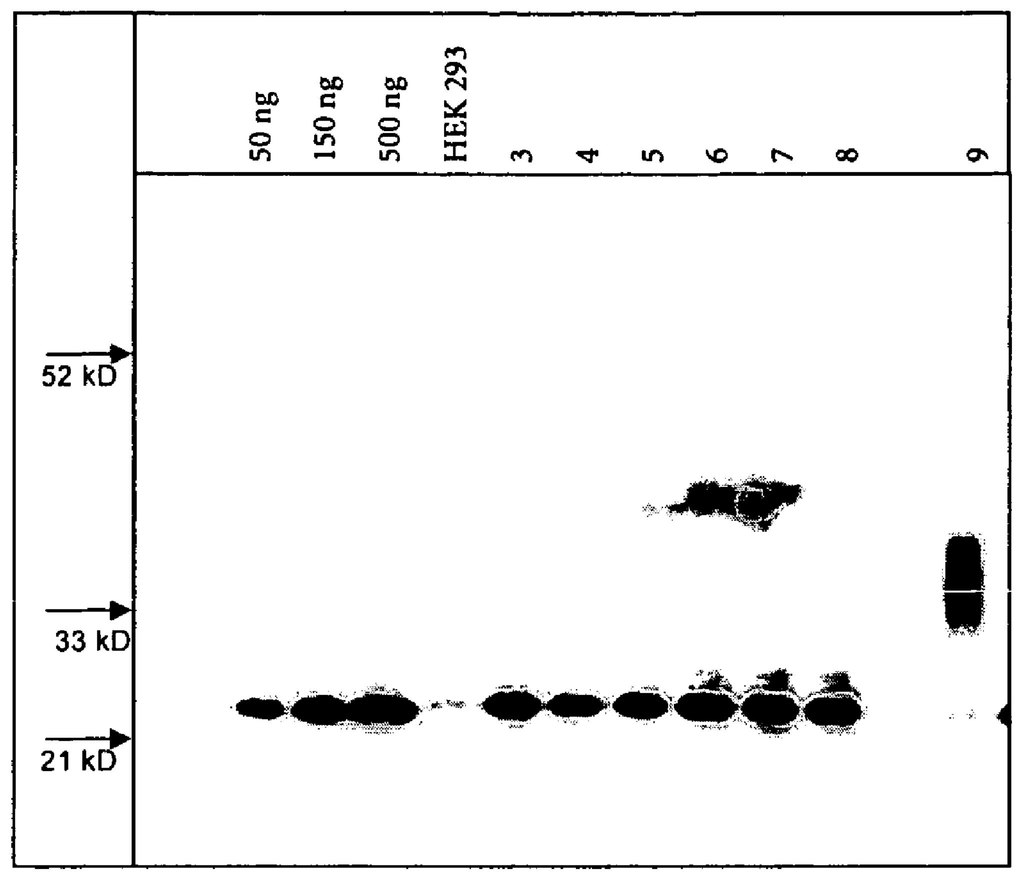
FIGS. 8*a*, 8*b*, and 8*c* Immunodetection of the light chain in cell culture supernatants after transient expression in HEK293 EBNA cells; sample arrangement according to table 6.
Figure 8B:
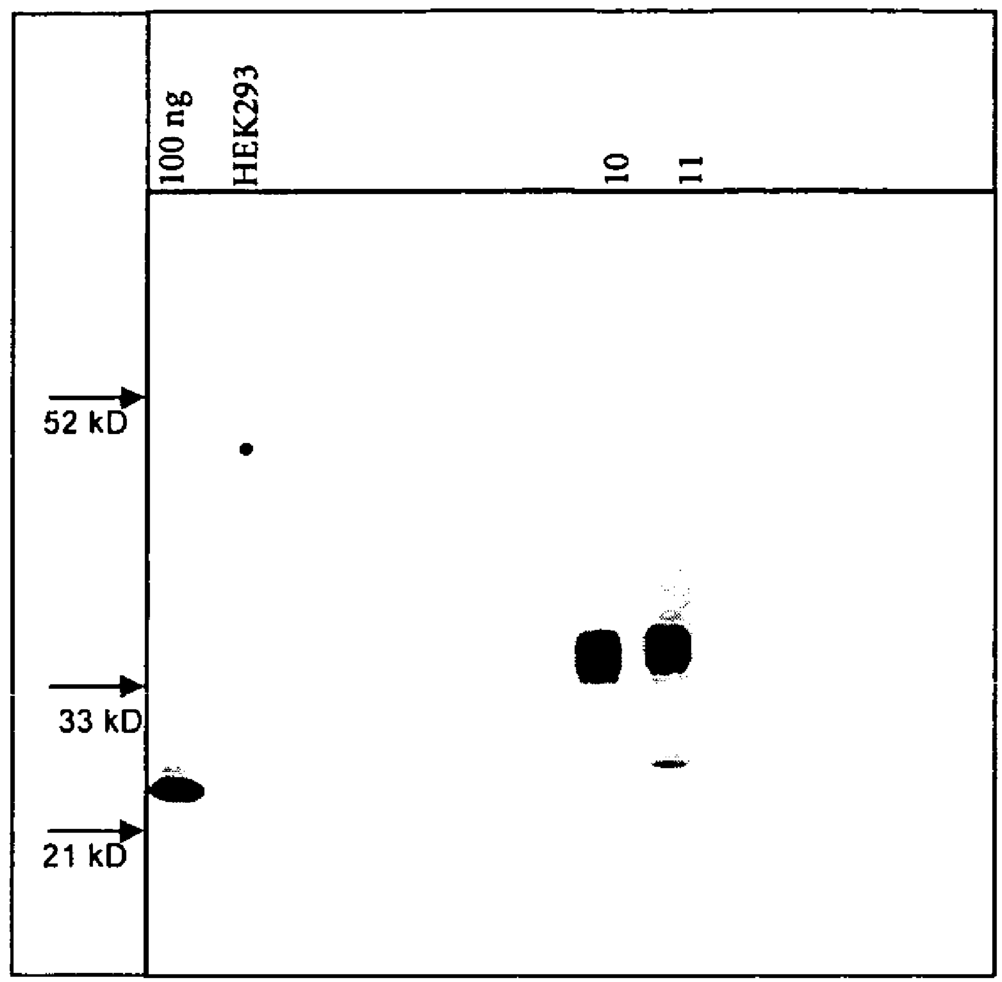
Figure 8C:
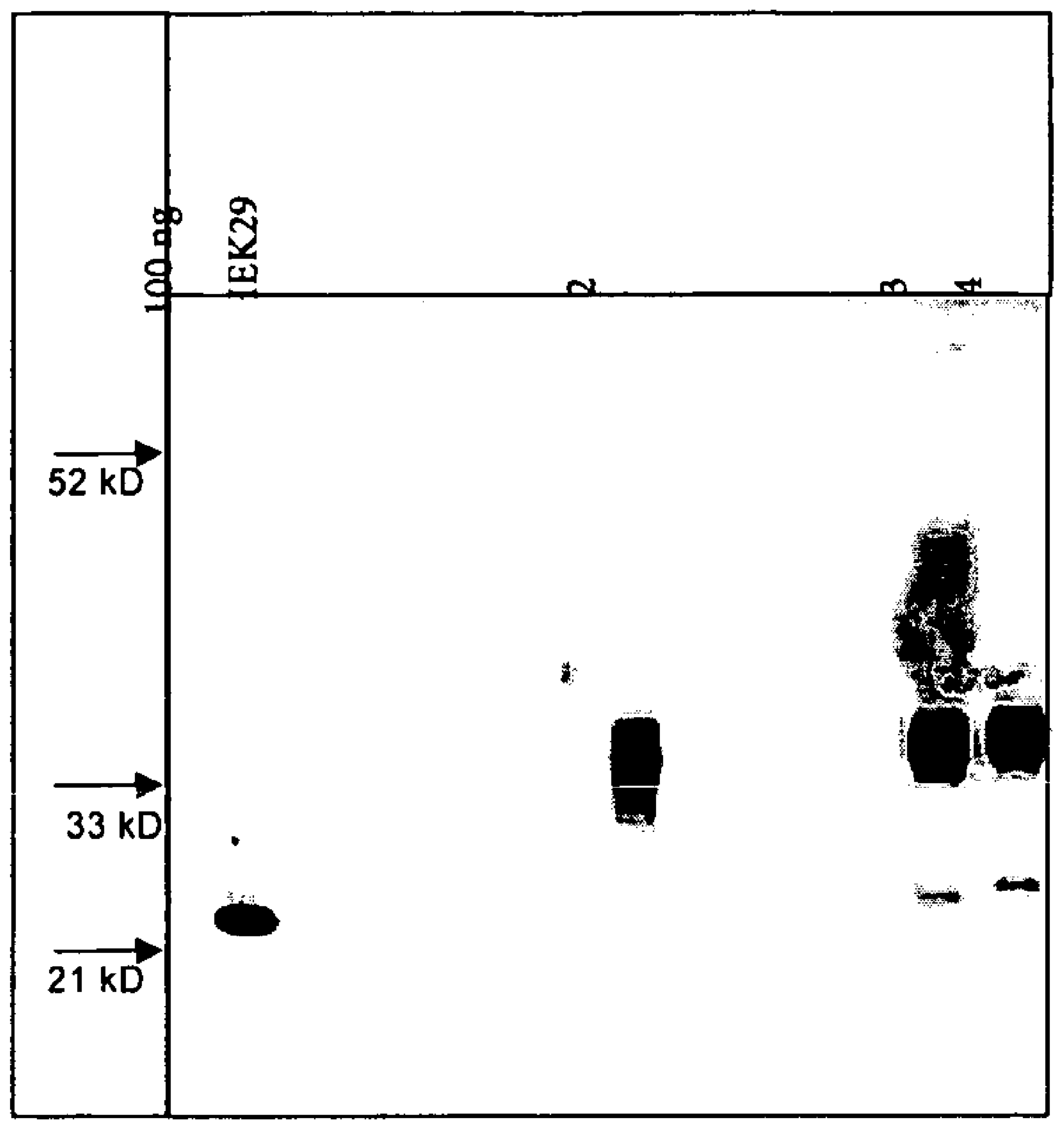

Immunodetection of Immunoglobulin Containing Polypeptides:

FIG. 8*a-c*: Immunodetection of light chain fragment containing polypeptides in cell culture supernatants after transient expression in HEK293 EBNA cells.

Figure 9A:
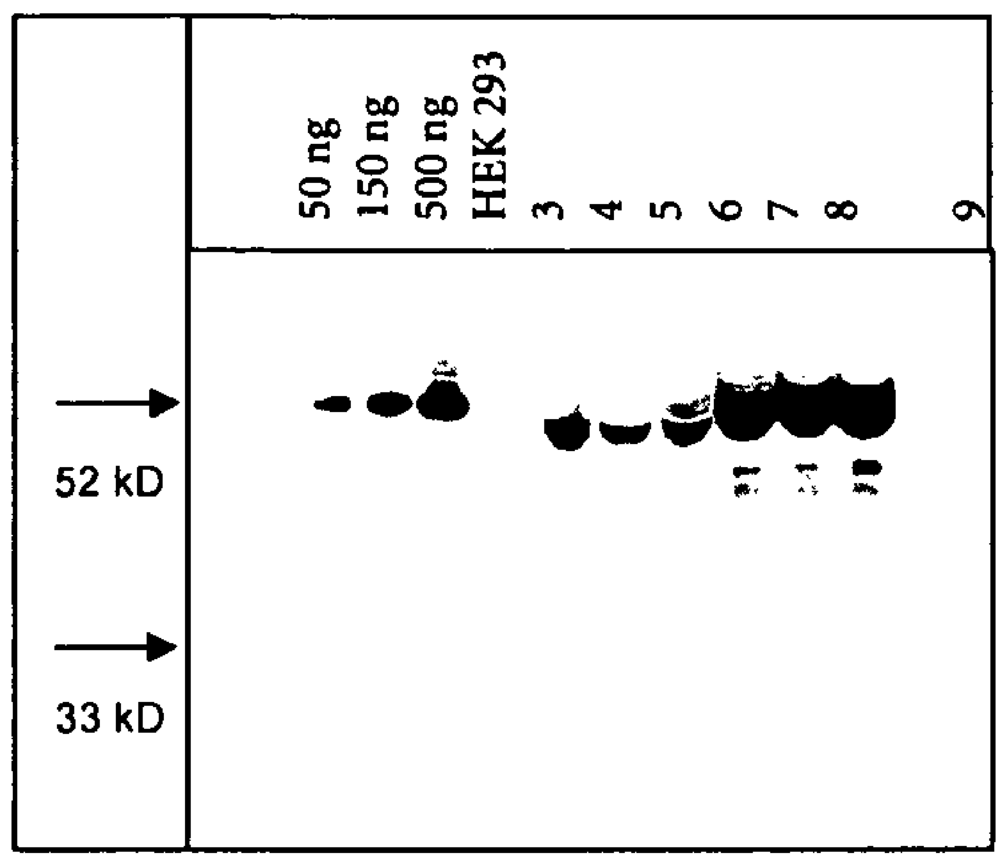
FIG. 9 Immunodetection of the heavy chain in cell culture supernatants after transient expression in HEK293 EBNA cells; sample arrangement according to table 6.
Figure 9B:
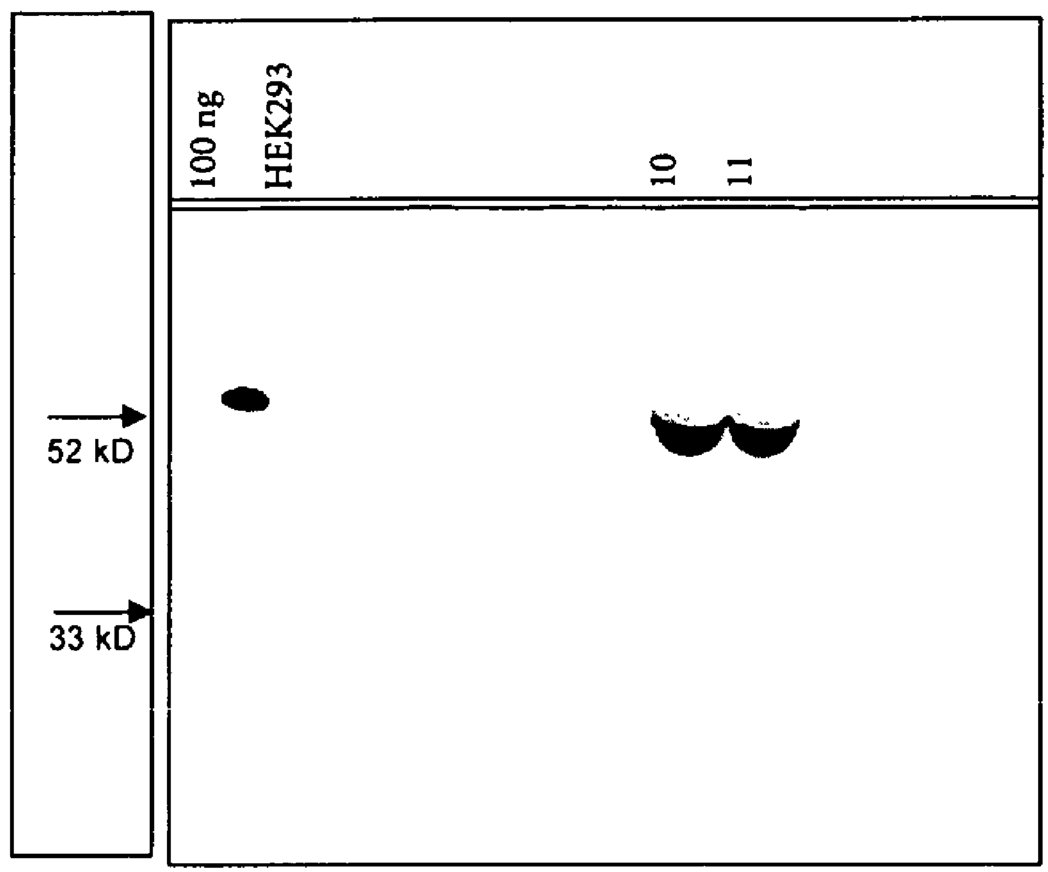
Figure 9C:
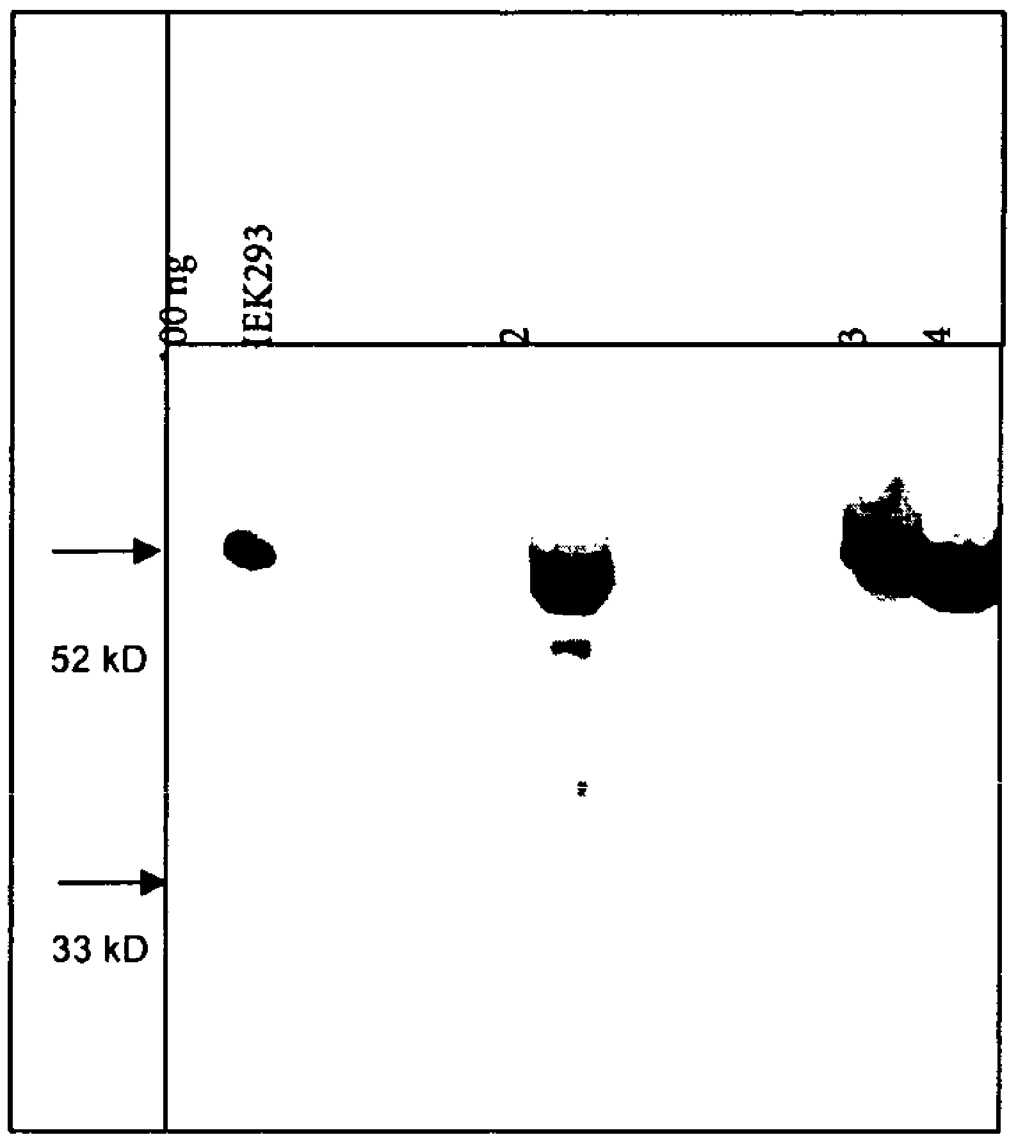

FIG. 9*a-c*: Immunodetection of the heavy chain fragment containing polypeptides in cell culture supernatants after transient expression in HEK293 EBNA cells.

From FIGS. 7*a-c*, 9*a-c* and 10 *a-c* it can be deduced that the polypeptides are transiently expressed and secreted into the culture medium. In the case that the immunoglobulin containing polypeptide possesses one or several glycosylation sites the final polypeptides have no exactly defined molecular weight but a molecular weight distribution depending on the extent of glycosylation. This causes in SDS-PAGE that the species all representing one polypeptide do not migrate homogeneously and thus the bands are broadened.

Example 6

Quantitation of the Expressed Heavy Chain Containing Polypeptides with Human IgG ELISA The immunoglobulin heavy chain fragment containing polypeptide concentration in cell culture supernatants was determined by a sandwich ELISA which used a biotinylated anti-human IgG $F(ab')_2$ fragment as the capture reagent and for detection a peroxidase-conjugated anti-human IgG $F(ab')_2$ antibody fragment.

Streptavidin coated 96-well plates (Pierce Reacti-Bind™ Streptavidin Coated Polystyrene Strip Plates, Code No. 15121, Pierce Chemical Company, USA) were coated with 0.5 μg/ml biotinylated goat polyclonal anti-human IgG $F(ab')_2$ antibody fragment (($F(ab')_2$<h-Fcγ>Bi; Dianova, Germany, Code No. 109-066-098) capture antibody (0.1 ml/well) in diluent buffer (diluent buffer: PBS buffer containing 0.5% weight by volume (w/v) bovine serum albumin) by incubation for one hour at room temperature (RT) under shaking. Thereafter, the plates were washed three times with more than 0.3 ml wash buffer (wash buffer: PBS containing 1% weight by volume (w/v) Tween 20). IgG immunoglobulin conjugate containing cell culture supernatants (samples) were diluted serially (twofold) up to a concentration of 0.5-20 ng/ml in diluent buffer, added to plates and incubated for one hour at RT with shaking. Purified anti-IGF-1R standard antibody (0.5-20 ng/ml) in diluent buffer was used for the generation of an IgG protein standard curve. After washing the plates three times with 0.3 ml/well wash buffer, bound complexes to human Fcgamma were detected with a peroxidase-conjugated $F(ab')_2$ fragment of goat polyclonal anti-human $F(ab')_2$-specific IgG [$F(ab')_2$<h-Fcγ>POD; Dianova, Code No. 109-036-098]. After washing the plates thrice with 0.3 ml/well wash buffer the plates were developed with ABTS® (2,2'-azino-bis(3-ethylbenzthiazoline-6-sulfonic acid) peroxidase substrate solution (Roche Molecular Biochemicals, Code No. 1684302, Roche Diagnostics GmbH, Germany). After 10-30 minutes the absorbance was measured at 405 nm and 490 nm against a reagent blank (incubation buffer+ABTS solution) on a Tecan Spectrafluorplus plate reader (Tecan Deutschland GmbH, Germany). For background correction the absorbance at 490 nm was subtracted from the absorbance at 405 nm according to formula I. All samples were assayed at least as duplicates, and the values from double or triple absorbance measurements were averaged. The IgG content of the samples were calculated from a standard curve.

$$\Delta A=(A_{sample}^{405}-A_{sample}^{490})-(A_{blank}^{405}-A_{blank}^{490}) \quad \text{Formula I}$$

The invention claimed is:

1. A method for the recombinant production of a heterologous polypeptide in a eukaryotic host cell, said method comprising:

a) providing a eukaryotic host cell comprising an expression plasmid, wherein the expression plasmid comprises in a 5' to 3' direction:

aa) a promoter, ab) a nucleic acid encoding a first polypeptide, wherein said first polypeptide is murine immunoglobulin signal sequence comprising SEQ ID NO: 327, ac) a nucleic acid encoding a said second polypeptide, comprising i) a nucleic acid encoding said heterologous polypeptide comprising SEQ ID NO: 12, ii) a nucleic acid encoding a linker, iii) a nucleic acid encoding an immunoglobulin fragment, wherein said second polypeptide further comprises an additional nucleic acid encoding the peptide QIWNN (SEQ ID NO: 472) in 5' position to the nucleic acid encoding said heterologous polypeptide, ad) a 3' untranslated region comprising a polyadenylation signal, and b) cultivating the host cell in a culture medium under conditions suitable for the expression of the second polypeptide.

2. The method of claim 1, further comprising:

c) recovering the second polypeptide from the culture medium.

3. The method of claim 1, wherein said immunoglobulin fragment is obtained either from an IgG or from an IgE.

4. The method of claim 1, wherein said eukaryotic cell is a mammalian cell.

5. The method of claim 4, wherein the mammalian cell is selected from the group consisting of a CHO cell, NS0 cell, Sp2/0 cell, COS cell, K562 cell, BHK cell, PER.C6 cell and HEK cell.

6. The method of claim 1, wherein said linker comprises a polypeptide selected from the group consisting of SEQ ID NO: 06, 07, 08, 09, 10, 139, 140, 554, 555, 556, and 557.

7. The method of claim 1, wherein said immunoglobulin fragment comprises a) either the $C_H1$-, $C_H2$-, $C_H3$-domain and the hinge region of an immunoglobulin heavy chain or the $C_L$-domain of an immunoglobulin light chain; and b) a fragment of a variable immunoglobulin heavy or light chain domain.

8. The method of claim 1, wherein said immunoglobulin fragment comprises only constant domains.

9. A plasmid, comprising in 5' to 3' direction:

a) a promoter, b) a nucleic acid encoding a first polypeptide, wherein said first polypeptide is murine immunoglobulin signal sequence comprising SEQ ID NO: 327;

c) a nucleic acid encoding a second polypeptide comprising i) a nucleic acid encoding a heterologous polypeptide comprising SEQ ID NO: 12, ii) a nucleic acid encoding a linker, iii) a nucleic acid encoding an immunoglobulin fragment;

wherein said second polypeptide further comprises an additional nucleic acid encoding the peptide QIWNN (SEQ ID NO: 472) in 5' position to the nucleic acid encoding said heterologous polypeptide, and d) a 3' untranslated region comprising a polyadenylation signal.

10. The plasmid of claim 9 wherein said linker comprises a polypeptide selected from the group consisting of SEQ ID NO: 06, 07, 08, 09, 10, 139, 140, 554, 555, 556, and 557.

* * * * *

SEQUENCE LISTING

```
<160> NUMBER OF SEQ ID NOS: 558

<210> SEQ ID NO 1
<211> LENGTH: 21
<212> TYPE: DNA
<213> ORGANISM: Artificial
<220> FEATURE:
<223> OTHER INFORMATION: synthetic linker comprising a BglII restriction
      site at the 5-end and a NheI restriction site at the 3-end (NheI
      site within the CH1 N-terminus)

<400> SEQUENCE: 1

agatcttttg ccaccgctag c                                              21


<210> SEQ ID NO 2
<211> LENGTH: 15
<212> TYPE: PRT
<213> ORGANISM: Mus musculus

<400> SEQUENCE: 2

Met Asp Phe Gly Leu Ser Leu Val Phe Leu Val Leu Ile Leu Lys
1               5                   10                  15


<210> SEQ ID NO 3
<211> LENGTH: 24
<212> TYPE: DNA
<213> ORGANISM: Artificial
<220> FEATURE:
<223> OTHER INFORMATION: synthetic linker arranged with a BglII
      restriction site at the 5- and a NheI restriction site at the
      3-end directly joined to the VL-IR variable region

<400> SEQUENCE: 3

agatctatat atatatatgc tagc                                           24


<210> SEQ ID NO 4
```

-continued

```
<211> LENGTH: 27
<212> TYPE: DNA
<213> ORGANISM: Artificial
<220> FEATURE:
<223> OTHER INFORMATION: BglII restriction site at the 3-end of
      CMV-promoter and BbsI restriction site inside the constant region
      of <IGF-IR>HuMab antibody light chain

<400> SEQUENCE: 4

cgaactgtgg ctgcaccatc tgtcttc                                         27


<210> SEQ ID NO 5
<211> LENGTH: 15
<212> TYPE: PRT
<213> ORGANISM: Mus musculus

<400> SEQUENCE: 5

Met Gly Trp Ser Cys Ile Ile Leu Ile Leu Val Ala Ala Ala Thr
1               5                   10                  15


<210> SEQ ID NO 6
<211> LENGTH: 15
<212> TYPE: PRT
<213> ORGANISM: Artificial
<220> FEATURE:
<223> OTHER INFORMATION: linker 1

<400> SEQUENCE: 6

Ser Gly Gly Gly Gly Ser Gly Gly Gly Gly Ser Gly Gly Gly Gly
1               5                   10                  15


<210> SEQ ID NO 7
<211> LENGTH: 25
<212> TYPE: PRT
<213> ORGANISM: Artificial
<220> FEATURE:
<223> OTHER INFORMATION: linker 2

<400> SEQUENCE: 7

Ser Gly Gly Gly Gly Ser Gly Gly Gly Gly Ser Gly Gly Gly Gly Ser
1               5                   10                  15

Gly Gly Gly Gly Ser Gly Gly Gly Gly
            20                  25


<210> SEQ ID NO 8
<211> LENGTH: 15
<212> TYPE: PRT
<213> ORGANISM: Artificial
<220> FEATURE:
<223> OTHER INFORMATION: linker 3

<400> SEQUENCE: 8

Gly Gln Gln Gln Gln Gly Gln Gln Gln Gln Gly Gln Gln Gln Gln
1               5                   10                  15


<210> SEQ ID NO 9
<211> LENGTH: 17
<212> TYPE: PRT
<213> ORGANISM: Artificial
<220> FEATURE:
<223> OTHER INFORMATION: linker 4

<400> SEQUENCE: 9

Gly Ser Ser Ser Ser Ser Ser Ser Ser Ser Ser Ser Ser Ser Ser Ser
1               5                   10                  15

Gly
```

<210> SEQ ID NO 10
<211> LENGTH: 3
<212> TYPE: PRT
<213> ORGANISM: Artificial
<220> FEATURE:
<223> OTHER INFORMATION: linker 5

<400> SEQUENCE: 10

```
Gly Ser Thr
1
```

<210> SEQ ID NO 11
<211> LENGTH: 345
<212> TYPE: PRT
<213> ORGANISM: Human immunodeficiency virus
<220> FEATURE:
<221> NAME/KEY: misc_feature
<223> OTHER INFORMATION: Natural amino acid sequence derived from the HIV-1 gp41 glycoprotein of HN-1 isolate LAI/IIIB clone BH8 (locus HIVH3BH8) (bp-position: 507-851)

<400> SEQUENCE: 11

```
Ala Val Gly Ile Gly Ala Leu Phe Leu Gly Phe Leu Gly Ala Ala Gly
1               5                   10                  15

Ser Thr Met Gly Ala Ala Ser Met Thr Leu Thr Val Gln Ala Arg Gln
            20                  25                  30

Leu Leu Ser Gly Ile Val Gln Gln Gln Asn Asn Leu Leu Arg Ala Ile
        35                  40                  45

Glu Gly Gln Gln His Leu Leu Gln Leu Thr Val Trp Gly Ile Lys Gln
    50                  55                  60

Leu Gln Ala Arg Ile Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Glu Gln Ile Trp
            100                 105                 110

Asn Asn Met Thr Trp Met Glu Trp Asp Arg Glu Ile Asn Asn Tyr Thr
        115                 120                 125

Ser Leu Ile His Ser Leu Ile Glu Glu Ser Gln Asn Gln Gln Glu Lys
    130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Leu Phe Ile Met
                165                 170                 175

Ile Val Gly Gly Leu Val Gly Leu Arg Ile Val Phe Ala Val Leu Ser
            180                 185                 190

Ile Val Asn Arg Val Arg Gln Gly Tyr Ser Pro Leu Ser Phe Gln Thr
        195                 200                 205

His Leu Pro Asn Pro Arg Gly Pro Asp Arg Pro Glu Gly Ile Glu Glu
    210                 215                 220

Glu Gly Gly Glu Arg Asp Arg Asp Arg Ser Ile Arg Leu Val Asn Gly
225                 230                 235                 240

Ser Leu Ala Leu Ile Trp Asp Asp Leu Arg Ser Leu Cys Leu Phe Ser
                245                 250                 255

Tyr His Arg Leu Arg Asp Leu Leu Leu Ile Val Thr Arg Ile Val Glu
            260                 265                 270

Leu Leu Gly Arg Arg Gly Trp Glu Ala Leu Lys Tyr Trp Trp Asn Leu
```

-continued

```
        275                 280                 285

Leu Gln Tyr Trp Ser Gln Glu Leu Lys Asn Ser Ala Val Asn Leu Leu
    290                 295                 300

Asn Ala Thr Ala Ile Ala Val Ala Glu Gly Thr Asp Arg Val Ile Glu
305                 310                 315                 320

Leu Val Gln Ala Ala Tyr Arg Ala Ile Arg His Ile Pro Arg Arg Ile
                325                 330                 335

Arg Gln Gly Leu Glu Arg Ile Leu Leu
            340                 345


<210> SEQ ID NO 12
<211> LENGTH: 36
<212> TYPE: PRT
<213> ORGANISM: Human immunodeficiency virus
<220> FEATURE:
<221> NAME/KEY: misc_feature
<223> OTHER INFORMATION: Natural amino acid sequence derived from the
      HIV-1 gp41 ectodomain (bp-position: 621-656)

<400> SEQUENCE: 12

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu
        35


<210> SEQ ID NO 13
<211> LENGTH: 123
<212> TYPE: PRT
<213> ORGANISM: Human immunodeficiency virus
<220> FEATURE:
<221> NAME/KEY: misc_feature
<223> OTHER INFORMATION: HIV-1 gp41 ectodomain variant I568P (single
      mutant), pb-position 534-656

<400> SEQUENCE: 13

Val Gln Ala Arg Gln Leu Leu Ser Gly Ile Val Gln Gln Gln Asn Asn
1               5                   10                  15

Leu Leu Arg Ala Ile Glu Gly Gln Gln His Leu Leu Gln Leu Thr Val
            20                  25                  30

Trp Gly Pro Lys Gln Leu Gln Ala Arg Ile Leu Ala Val Glu Arg Tyr
        35                  40                  45

Leu Lys Asp Gln Gln Leu Leu Gly Ile Trp Gly Cys Ser Gly Lys Leu
    50                  55                  60

Ile Cys Thr Thr Ala Val Pro Trp Asn Ala Ser Trp Ser Asn Lys Ser
65                  70                  75                  80

Leu Glu Gln Ile Trp Asn Asn Met Thr Trp Met Glu Trp Asp Arg Glu
                85                  90                  95

Ile Asn Asn Tyr Thr Ser Leu Ile His Ser Leu Ile Glu Glu Ser Gln
            100                 105                 110

Asn Gln Gln Glu Lys Asn Glu Gln Glu Leu Leu
        115                 120


<210> SEQ ID NO 14
<211> LENGTH: 135
<212> TYPE: PRT
<213> ORGANISM: Human immunodeficiency virus
<220> FEATURE:
<221> NAME/KEY: misc_feature
<223> OTHER INFORMATION: HIV-1 gp41 ectodomain variant I568P, L550E,
```

-continued

L566E, I580E (quadruple mutant), bp-position 522-656

<400> SEQUENCE: 14

```
Gly Ser Thr Met Gly Ala Ala Ser Met Thr Leu Thr Val Gln Ala Arg
1               5                   10                  15

Gln Leu Leu Ser Gly Ile Val Gln Gln Gln Asn Asn Glu Leu Arg Ala
            20                  25                  30

Ile Glu Gly Gln Gln His Leu Glu Gln Leu Thr Val Trp Gly Pro Lys
        35                  40                  45

Gln Leu Gln Ala Arg Glu Leu Ala Val Glu Arg Tyr Leu Lys Asp Gln
    50                  55                  60

Gln Leu Leu Gly Ile Trp Gly Cys Ser Gly Lys Leu Ile Cys Thr Thr
65                  70                  75                  80

Ala Val Pro Trp Asn Ala Ser Trp Ser Asn Lys Ser Leu Glu Gln Ile
                85                  90                  95

Trp Asn Asn Met Thr Trp Met Glu Trp Asp Arg Glu Ile Asn Asn Tyr
            100                 105                 110

Thr Ser Leu Ile His Ser Leu Ile Glu Glu Ser Gln Asn Gln Gln Glu
        115                 120                 125

Lys Asn Glu Gln Glu Leu Leu
    130                 135
```

<210> SEQ ID NO 15
<211> LENGTH: 133
<212> TYPE: DNA
<213> ORGANISM: Human immunodeficiency virus
<220> FEATURE:
<221> NAME/KEY: misc_feature
<223> OTHER INFORMATION: Insert 4964

<400> SEQUENCE: 15

```
agatctatat atatatatgc tagcgaaatt gtgttgacac agtctccagc caccctgtct     60

ttgtctccag gggaaagagc caccctctcc tgcagggcca gtcagagtgt tagtagctac    120

ttagcctggt acc                                                       133
```

<210> SEQ ID NO 16
<211> LENGTH: 249
<212> TYPE: DNA
<213> ORGANISM: Human immunodeficiency virus
<220> FEATURE:
<221> NAME/KEY: misc_feature
<223> OTHER INFORMATION: Insert 4965

<400> SEQUENCE: 16

```
agatcttttg ccaccatgga caccctgtgc agcaccctgc tcctgctgac catccccagc     60

tgggtgctct cccaaatctg gaacaacatg acctggatgg agtgggaccg cgagatcaat    120

aactacacaa gcttgatcca ctctctgatc gaggaaagcc agaaccagca ggagaagaac    180

gagcaggagc tcctgggcgg gggtggatcc ggcggcgggg gcagcggcgg gggaggctcc    240

ggcgctagc                                                            249
```

<210> SEQ ID NO 17
<211> LENGTH: 279
<212> TYPE: DNA
<213> ORGANISM: Human immunodeficiency virus
<220> FEATURE:
<221> NAME/KEY: misc_feature
<223> OTHER INFORMATION: Insert 4966

<400> SEQUENCE: 17

```
agatcttttg ccaccatgga caccctgtgc agcaccctgc tcctgctgac catccccagc     60

tgggtgctct cccaaatctg gaacaacatg acctggatgg agtgggaccg cgagatcaat    120

aactacacaa gcttgatcca ctctctgatc gaggaaagcc agaaccagca ggagaagaac    180

gagcaggagc tcctgggcgg gggtggctcc ggcggcgggg gcagcggcgg gggaggctcc    240

ggcgggggcg gatccggggg cggtggcagc ggcgctagc                           279


<210> SEQ ID NO 18
<211> LENGTH: 252
<212> TYPE: DNA
<213> ORGANISM: Human immunodeficiency virus
<220> FEATURE:
<221> NAME/KEY: misc_feature
<223> OTHER INFORMATION: Insert 4967

<400> SEQUENCE: 18

agatcttttg ccaccatgga caccctgtgc agcaccctgc tcctgctgac catccccagc     60

tgggtgctct cccaaatctg gaacaacatg acctggatgg agtgggaccg cgagatcaat    120

aactacacaa gcttgatcca ctccctgatc gaggaaagcc agaaccagca ggagaagaac    180

gagcaggagc tcctgggatc cagctccagc tccagctcca gctccagcag tagctccagc    240

tctggcgcta gc                                                        252


<210> SEQ ID NO 19
<211> LENGTH: 589
<212> TYPE: DNA
<213> ORGANISM: Human immunodeficiency virus
<220> FEATURE:
<221> NAME/KEY: misc_feature
<223> OTHER INFORMATION: Insert 4969

<400> SEQUENCE: 19

agatctagct ctgggagagg agcccagcac tagaagtcgg cggtgtttcc attcggtgat     60

cagcactgaa cacagaggac tcaccatgga gtttgggctg agctgggtgt tcctcgtggc    120

actgctcagg ggtgtacagt gtcaggtgca ggcccgccag ctgctctccg gcatcgtcca    180

gcagcaaaac aatctgctgc gggcgatcga ggggcagcag cacctcctgc agctgacggt    240

gtggggtccc aagcagctgc aggcccgcat tctggccgtg gaacggtacc tgaaggacca    300

gcagctgctc ggcatctggg gatgctctgg caagcttatc tgcaccacag ccgtcccctg    360

gaacgctagc tggagtaaca aaagcctgga gcaaatttgg aacaacatga cctggatgga    420

gtgggatcgc gagatcaata attacacaag cctgatccac tccctgatcg aggaaagcca    480

gaaccagcag gagaagaacg agcaggagct cctgggcggg ggcggatccg gcggcggggg    540

cagcggtggg ggcggctccg gccgaactgt ggctgcacca tctgtcttc                589


<210> SEQ ID NO 20
<211> LENGTH: 15
<212> TYPE: PRT
<213> ORGANISM: Mus musculus

<400> SEQUENCE: 20

Met Asn Phe Gly Leu Arg Leu Ile Phe Leu Val Leu Thr Leu Lys
1               5                   10                  15


<210> SEQ ID NO 21
<211> LENGTH: 15
<212> TYPE: PRT
<213> ORGANISM: Mus musculus
```

<400> SEQUENCE: 21

```
Met Asn Phe Gly Leu Ser Leu Ile Phe Leu Val Leu Ile Leu Lys
1               5                   10                  15
```

<210> SEQ ID NO 22
<211> LENGTH: 13
<212> TYPE: PRT
<213> ORGANISM: Mus musculus

<400> SEQUENCE: 22

```
Met Gly Val Pro Thr Gln Leu Leu Leu Leu Trp Leu Thr
1               5                   10
```

<210> SEQ ID NO 23
<211> LENGTH: 16
<212> TYPE: PRT
<213> ORGANISM: Mus musculus

<400> SEQUENCE: 23

```
Met Arg Val Leu Ala Glu Leu Leu Gly Leu Leu Leu Phe Cys Phe Leu
1               5                   10                  15
```

<210> SEQ ID NO 24
<211> LENGTH: 16
<212> TYPE: PRT
<213> ORGANISM: Mus musculus

<400> SEQUENCE: 24

```
Met Arg Val Leu Pro Glu Phe Leu Gly Leu Leu Leu Leu Trp Ile Ser
1               5                   10                  15
```

<210> SEQ ID NO 25
<211> LENGTH: 16
<212> TYPE: PRT
<213> ORGANISM: Mus musculus

<400> SEQUENCE: 25

```
Met Arg Cys Ser Leu Gln Phe Leu Gly Val Leu Met Phe Trp Ile Ser
1               5                   10                  15
```

<210> SEQ ID NO 26
<211> LENGTH: 15
<212> TYPE: PRT
<213> ORGANISM: Mus musculus

<400> SEQUENCE: 26

```
Arg Glu Trp Ser Trp Asn Phe Leu Phe Leu Leu Ser Gly Thr Thr
1               5                   10                  15
```

<210> SEQ ID NO 27
<211> LENGTH: 15
<212> TYPE: PRT
<213> ORGANISM: Mus musculus

<400> SEQUENCE: 27

```
Met Glu Trp Ser Gly Val Phe Ile Phe Leu Leu Ser Val Thr Ala
1               5                   10                  15
```

<210> SEQ ID NO 28
<211> LENGTH: 19
<212> TYPE: PRT
<213> ORGANISM: Homo sapiens

<400> SEQUENCE: 28

```
Met Asp Trp Thr Trp Arg Ile Leu Phe Leu Val Ala Ala Ala Thr Gly
1               5                   10                  15

Ala His Ser


<210> SEQ ID NO 29
<211> LENGTH: 19
<212> TYPE: PRT
<213> ORGANISM: Homo sapiens

<400> SEQUENCE: 29

Met Asp Trp Thr Trp Arg Ile Leu Phe Leu Val Ala Ala Ala Thr Gly
1               5                   10                  15

Ala His Ser


<210> SEQ ID NO 30
<211> LENGTH: 19
<212> TYPE: PRT
<213> ORGANISM: Homo sapiens

<400> SEQUENCE: 30

Met Asp Trp Thr Trp Arg Ile Leu Phe Leu Val Ala Ala Ala Thr Ser
1               5                   10                  15

Ala His Ser


<210> SEQ ID NO 31
<211> LENGTH: 19
<212> TYPE: PRT
<213> ORGANISM: Homo sapiens

<400> SEQUENCE: 31

Met Asp Trp Thr Trp Ser Ile Leu Phe Leu Val Ala Ala Pro Thr Gly
1               5                   10                  15

Ala His Ser


<210> SEQ ID NO 32
<211> LENGTH: 19
<212> TYPE: PRT
<213> ORGANISM: Homo sapiens

<400> SEQUENCE: 32

Met Asp Cys Thr Trp Arg Ile Leu Phe Leu Val Ala Ala Ala Thr Gly
1               5                   10                  15

Thr His Ala


<210> SEQ ID NO 33
<211> LENGTH: 19
<212> TYPE: PRT
<213> ORGANISM: Homo sapiens

<400> SEQUENCE: 33

Met Asp Trp Thr Trp Arg Ile Leu Phe Leu Val Ala Ala Ala Thr Asp
1               5                   10                  15

Ala Tyr Ser


<210> SEQ ID NO 34
<211> LENGTH: 19
<212> TYPE: PRT
<213> ORGANISM: Homo sapiens

<400> SEQUENCE: 34
```

-continued

```
Met Asp Trp Thr Trp Arg Val Phe Cys Leu Leu Ala Val Ala Pro Gly
1               5                   10                  15

Ala His Ser


<210> SEQ ID NO 35
<211> LENGTH: 19
<212> TYPE: PRT
<213> ORGANISM: Homo sapiens

<400> SEQUENCE: 35

Met Asp Trp Ile Trp Arg Ile Leu Phe Leu Val Gly Ala Ala Thr Gly
1               5                   10                  15

Ala His Ser


<210> SEQ ID NO 36
<211> LENGTH: 19
<212> TYPE: PRT
<213> ORGANISM: Homo sapiens

<400> SEQUENCE: 36

Met Asp Thr Leu Cys Ser Thr Leu Leu Leu Leu Thr Ile Pro Ser Trp
1               5                   10                  15

Val Leu Ser


<210> SEQ ID NO 37
<211> LENGTH: 19
<212> TYPE: PRT
<213> ORGANISM: Homo sapiens

<400> SEQUENCE: 37

Met Asp Thr Leu Cys Tyr Thr Leu Leu Leu Leu Thr Thr Pro Ser Trp
1               5                   10                  15

Val Leu Ser


<210> SEQ ID NO 38
<211> LENGTH: 19
<212> TYPE: PRT
<213> ORGANISM: Homo sapiens

<400> SEQUENCE: 38

Met Glu Leu Gly Leu Ser Trp Val Phe Leu Val Ala Ile Leu Glu Gly
1               5                   10                  15

Val Gln Cys


<210> SEQ ID NO 39
<211> LENGTH: 19
<212> TYPE: PRT
<213> ORGANISM: Homo sapiens

<400> SEQUENCE: 39

Met Glu Leu Gly Leu Ser Trp Ile Phe Leu Leu Ala Ile Leu Lys Gly
1               5                   10                  15

Val Gln Cys


<210> SEQ ID NO 40
<211> LENGTH: 19
<212> TYPE: PRT
<213> ORGANISM: Homo sapiens

<400> SEQUENCE: 40

Met Glu Phe Gly Leu Ser Trp Val Phe Leu Val Ala Ile Ile Lys Gly
```

1 5 10 15

Val Gln Cys

<210> SEQ ID NO 41
<211> LENGTH: 19
<212> TYPE: PRT
<213> ORGANISM: Homo sapiens

<400> SEQUENCE: 41

Met Glu Leu Gly Leu Ser Trp Val Phe Leu Val Ala Ile Leu Glu Gly
1 5 10 15

Val Gln Cys

<210> SEQ ID NO 42
<211> LENGTH: 19
<212> TYPE: PRT
<213> ORGANISM: Homo sapiens

<400> SEQUENCE: 42

Met Glu Phe Gly Leu Ser Trp Ile Phe Leu Ala Ala Ile Leu Lys Gly
1 5 10 15

Val Gln Cys

<210> SEQ ID NO 43
<211> LENGTH: 19
<212> TYPE: PRT
<213> ORGANISM: Homo sapiens

<400> SEQUENCE: 43

Met Glu Phe Gly Leu Ser Trp Val Phe Leu Val Ala Ile Leu Lys Gly
1 5 10 15

Val Gln Cys

<210> SEQ ID NO 44
<211> LENGTH: 19
<212> TYPE: PRT
<213> ORGANISM: Homo sapiens

<400> SEQUENCE: 44

Met Glu Leu Gly Leu Arg Trp Val Phe Leu Val Ala Ile Leu Glu Gly
1 5 10 15

Val Gln Cys

<210> SEQ ID NO 45
<211> LENGTH: 19
<212> TYPE: PRT
<213> ORGANISM: Homo sapiens

<400> SEQUENCE: 45

Met Glu Phe Gly Leu Ser Trp Leu Phe Leu Val Ala Ile Leu Lys Gly
1 5 10 15

Val Gln Cys

<210> SEQ ID NO 46
<211> LENGTH: 19
<212> TYPE: PRT
<213> ORGANISM: Homo sapiens

<400> SEQUENCE: 46

Met Glu Phe Gly Leu Ser Trp Val Phe Leu Val Ala Leu Leu Arg Gly
1 5 10 15

Val Gln Cys

<210> SEQ ID NO 47
<211> LENGTH: 19
<212> TYPE: PRT
<213> ORGANISM: Homo sapiens

<400> SEQUENCE: 47

Met Glu Phe Gly Leu Ser Trp Val Phe Leu Val Ala Leu Leu Arg Gly
1 5 10 15

Val Gln Cys

<210> SEQ ID NO 48
<211> LENGTH: 19
<212> TYPE: PRT
<213> ORGANISM: Homo sapiens

<400> SEQUENCE: 48

Met Glu Phe Gly Leu Ser Trp Val Phe Leu Val Ala Ile Leu Lys Gly
1 5 10 15

Val Gln Cys

<210> SEQ ID NO 49
<211> LENGTH: 19
<212> TYPE: PRT
<213> ORGANISM: Homo sapiens

<400> SEQUENCE: 49

Met Glu Leu Gly Leu Cys Trp Val Phe Leu Val Ala Ile Leu Glu Gly
1 5 10 15

Val Gln Cys

<210> SEQ ID NO 50
<211> LENGTH: 19
<212> TYPE: PRT
<213> ORGANISM: Homo sapiens

<400> SEQUENCE: 50

Met Glu Phe Gly Leu Ser Trp Val Phe Leu Val Ala Ile Leu Lys Gly
1 5 10 15

Val Gln Cys

<210> SEQ ID NO 51
<211> LENGTH: 19
<212> TYPE: PRT
<213> ORGANISM: Homo sapiens

<400> SEQUENCE: 51

Met Glu Phe Trp Leu Ser Trp Val Phe Leu Val Ala Ile Leu Lys Gly
1 5 10 15

Val Gln Cys

<210> SEQ ID NO 52
<211> LENGTH: 20
<212> TYPE: PRT
<213> ORGANISM: human germline sequence

<400> SEQUENCE: 52

Met Thr Glu Phe Gly Leu Ser Trp Val Phe Leu Val Ala Ile Phe Lys
1 5 10 15

```
Gly Val Gln Cys
            20


<210> SEQ ID NO 53
<211> LENGTH: 19
<212> TYPE: PRT
<213> ORGANISM: Homo sapiens

<400> SEQUENCE: 53

Met Glu Phe Gly Leu Ser Trp Val Phe Leu Val Ala Ile Leu Lys Gly
1               5                   10                  15

Val Gln Cys


<210> SEQ ID NO 54
<211> LENGTH: 19
<212> TYPE: PRT
<213> ORGANISM: Homo sapiens

<400> SEQUENCE: 54

Met Glu Phe Gly Leu Ser Trp Val Phe Leu Val Val Ile Leu Gln Gly
1               5                   10                  15

Val Gln Cys


<210> SEQ ID NO 55
<211> LENGTH: 19
<212> TYPE: PRT
<213> ORGANISM: Homo sapiens

<400> SEQUENCE: 55

Met Glu Phe Gly Leu Ser Trp Val Phe Leu Val Ala Ile Leu Lys Gly
1               5                   10                  15

Val Gln Cys


<210> SEQ ID NO 56
<211> LENGTH: 19
<212> TYPE: PRT
<213> ORGANISM: Homo sapiens

<400> SEQUENCE: 56

Met Lys His Leu Trp Phe Phe Leu Leu Leu Val Ala Ala Pro Arg Trp
1               5                   10                  15

Val Leu Ser


<210> SEQ ID NO 57
<211> LENGTH: 19
<212> TYPE: PRT
<213> ORGANISM: Homo sapiens

<400> SEQUENCE: 57

Met Lys His Leu Trp Phe Phe Leu Leu Leu Val Ala Ala Pro Arg Trp
1               5                   10                  15

Val Leu Ser


<210> SEQ ID NO 58
<211> LENGTH: 19
<212> TYPE: PRT
<213> ORGANISM: Homo sapiens

<400> SEQUENCE: 58

Met Lys His Leu Trp Phe Phe Leu Leu Leu Val Ala Ala Pro Arg Trp
1               5                   10                  15
```

-continued

Val Leu Pro

<210> SEQ ID NO 59
<211> LENGTH: 19
<212> TYPE: PRT
<213> ORGANISM: Homo sapiens

<400> SEQUENCE: 59

Met Lys His Leu Trp Phe Phe Leu Leu Leu Val Ala Ala Pro Arg Trp
1 5 10 15

Val Leu Ser

<210> SEQ ID NO 60
<211> LENGTH: 19
<212> TYPE: PRT
<213> ORGANISM: Homo sapiens

<400> SEQUENCE: 60

Met Lys His Leu Trp Phe Phe Leu Leu Leu Val Ala Ala Pro Arg Trp
1 5 10 15

Val Leu Ser

<210> SEQ ID NO 61
<211> LENGTH: 19
<212> TYPE: PRT
<213> ORGANISM: Homo sapiens

<400> SEQUENCE: 61

Met Lys His Leu Trp Phe Phe Leu Leu Leu Val Ala Ala Pro Arg Trp
1 5 10 15

Val Leu Ser

<210> SEQ ID NO 62
<211> LENGTH: 19
<212> TYPE: PRT
<213> ORGANISM: Homo sapiens

<400> SEQUENCE: 62

Met Lys His Leu Trp Phe Phe Leu Leu Leu Val Ala Ala Pro Arg Trp
1 5 10 15

Val Leu Ser

<210> SEQ ID NO 63
<211> LENGTH: 19
<212> TYPE: PRT
<213> ORGANISM: Homo sapiens

<400> SEQUENCE: 63

Met Lys His Leu Trp Phe Phe Leu Leu Leu Val Ala Ala Pro Arg Trp
1 5 10 15

Val Leu Ser

<210> SEQ ID NO 64
<211> LENGTH: 19
<212> TYPE: PRT
<213> ORGANISM: Homo sapiens

<400> SEQUENCE: 64

Met Gly Ser Thr Ala Ile Leu Ala Leu Leu Leu Ala Val Leu Gln Gly
1 5 10 15

Val Cys Ser

-continued

<210> SEQ ID NO 65
<211> LENGTH: 19
<212> TYPE: PRT
<213> ORGANISM: human germline sequence

<400> SEQUENCE: 65

Met Gly Ser Thr Ala Ile Leu Gly Leu Leu Leu Ala Val Leu Gln Gly
1 5 10 15

Val Cys Ala

<210> SEQ ID NO 66
<211> LENGTH: 20
<212> TYPE: PRT
<213> ORGANISM: Homo sapiens

<400> SEQUENCE: 66

Met Ser Val Ser Phe Leu Ile Phe Leu Pro Val Leu Gly Leu Pro Trp
1 5 10 15

Gly Val Leu Ser
20

<210> SEQ ID NO 67
<211> LENGTH: 19
<212> TYPE: PRT
<213> ORGANISM: Homo sapiens

<400> SEQUENCE: 67

Met Asp Trp Thr Trp Arg Ile Leu Phe Leu Val Ala Ala Ala Thr Gly
1 5 10 15

Ala His Ser

<210> SEQ ID NO 68
<211> LENGTH: 22
<212> TYPE: PRT
<213> ORGANISM: Homo sapiens

<400> SEQUENCE: 68

Met Asp Met Arg Val Pro Ala Gln Leu Leu Gly Leu Leu Leu Leu Trp
1 5 10 15

Leu Arg Gly Ala Arg Cys
20

<210> SEQ ID NO 69
<211> LENGTH: 22
<212> TYPE: PRT
<213> ORGANISM: human germline sequence

<400> SEQUENCE: 69

Met Asp Met Arg Val Pro Ala Gln Leu Leu Gly Leu Leu Leu Leu Trp
1 5 10 15

Leu Arg Gly Ala Arg Cys
20

<210> SEQ ID NO 70
<211> LENGTH: 22
<212> TYPE: PRT
<213> ORGANISM: Homo sapiens

<400> SEQUENCE: 70

Met Asp Met Arg Val Pro Ala Gln Leu Leu Gly Leu Leu Gln Leu Trp
1 5 10 15

Leu Ser Gly Ala Arg Cys
20

<210> SEQ ID NO 71
<211> LENGTH: 22
<212> TYPE: PRT
<213> ORGANISM: Homo sapiens

<400> SEQUENCE: 71

Met Asp Met Arg Val Pro Ala Gln Leu Leu Gly Leu Leu Leu Leu Trp
1 5 10 15

Leu Ser Gly Ala Arg Cys
20

<210> SEQ ID NO 72
<211> LENGTH: 22
<212> TYPE: PRT
<213> ORGANISM: Homo sapiens

<400> SEQUENCE: 72

Met Asp Met Arg Val Pro Ala Gln Leu Leu Gly Leu Leu Leu Leu Trp
1 5 10 15

Leu Pro Asp Thr Arg Cys
20

<210> SEQ ID NO 73
<211> LENGTH: 22
<212> TYPE: PRT
<213> ORGANISM: Homo sapiens

<400> SEQUENCE: 73

Met Asp Met Arg Val Pro Ala Gln Leu Leu Gly Leu Leu Leu Leu Trp
1 5 10 15

Phe Pro Gly Ala Arg Cys
20

<210> SEQ ID NO 74
<211> LENGTH: 22
<212> TYPE: PRT
<213> ORGANISM: Homo sapiens

<400> SEQUENCE: 74

Met Asp Met Arg Val Pro Ala Gln Leu Leu Gly Leu Leu Leu Leu Trp
1 5 10 15

Phe Pro Gly Ala Arg Cys
20

<210> SEQ ID NO 75
<211> LENGTH: 22
<212> TYPE: PRT
<213> ORGANISM: Homo sapiens

<400> SEQUENCE: 75

Met Asp Met Arg Val Leu Ala Gln Leu Leu Gly Leu Leu Leu Leu Cys
1 5 10 15

Phe Pro Gly Ala Arg Cys
20

<210> SEQ ID NO 76
<211> LENGTH: 22
<212> TYPE: PRT
<213> ORGANISM: Homo sapiens

<400> SEQUENCE: 76

Met Asp Met Arg Val Leu Ala Gln Leu Leu Gly Leu Leu Leu Leu Cys
1 5 10 15

Phe Pro Gly Ala Arg Cys
20

<210> SEQ ID NO 77
<211> LENGTH: 22
<212> TYPE: PRT
<213> ORGANISM: Homo sapiens

<400> SEQUENCE: 77

Met Asp Met Arg Val Pro Ala Gln Leu Leu Gly Leu Leu Leu Leu Trp
1 5 10 15

Leu Pro Gly Ala Arg Cys
20

<210> SEQ ID NO 78
<211> LENGTH: 22
<212> TYPE: PRT
<213> ORGANISM: Homo sapiens

<400> SEQUENCE: 78

Met Asp Met Arg Val Pro Ala Gln Leu Leu Gly Leu Leu Leu Leu Trp
1 5 10 15

Leu Pro Gly Ala Arg Cys
20

<210> SEQ ID NO 79
<211> LENGTH: 22
<212> TYPE: PRT
<213> ORGANISM: Homo sapiens

<400> SEQUENCE: 79

Met Asp Met Arg Val Pro Ala Gln Leu Leu Gly Leu Leu Leu Leu Trp
1 5 10 15

Phe Pro Gly Ser Arg Cys
20

<210> SEQ ID NO 80
<211> LENGTH: 22
<212> TYPE: PRT
<213> ORGANISM: Homo sapiens

<400> SEQUENCE: 80

Met Asp Met Arg Val Pro Ala Gln Leu Leu Gly Leu Leu Leu Leu Trp
1 5 10 15

Phe Pro Gly Ser Arg Cys
20

<210> SEQ ID NO 81
<211> LENGTH: 22
<212> TYPE: PRT
<213> ORGANISM: Homo sapiens

<400> SEQUENCE: 81

Met Asp Met Arg Val Pro Ala Gln Leu Leu Gly Leu Leu Leu Leu Trp
1 5 10 15

Leu Pro Gly Ala Arg Cys
20

<210> SEQ ID NO 82
<211> LENGTH: 22
<212> TYPE: PRT
<213> ORGANISM: Homo sapiens

<400> SEQUENCE: 82

```
Met Asp Met Arg Val Pro Ala Gln Arg Leu Gly Leu Leu Leu Leu Trp
1               5                   10                  15

Phe Pro Gly Ala Arg Cys
            20
```

<210> SEQ ID NO 83
<211> LENGTH: 20
<212> TYPE: PRT
<213> ORGANISM: Homo sapiens

<400> SEQUENCE: 83

```
Met Arg Val Pro Ala Gln Leu Leu Gly Leu Leu Leu Leu Trp Leu Pro
1               5                   10                  15

Gly Ala Arg Cys
            20
```

<210> SEQ ID NO 84
<211> LENGTH: 22
<212> TYPE: PRT
<213> ORGANISM: Homo sapiens

<400> SEQUENCE: 84

```
Met Asp Met Arg Val Pro Ala Gln Leu Leu Gly Leu Leu Leu Leu Trp
1               5                   10                  15

Leu Pro Gly Ala Arg Cys
            20
```

<210> SEQ ID NO 85
<211> LENGTH: 22
<212> TYPE: PRT
<213> ORGANISM: human germline sequence

<400> SEQUENCE: 85

```
Met Asp Met Arg Val Pro Ala Gln Leu Leu Gly Leu Leu Leu Leu Trp
1               5                   10                  15

Leu Pro Gly Ala Arg Cys
            20
```

<210> SEQ ID NO 86
<211> LENGTH: 22
<212> TYPE: PRT
<213> ORGANISM: Homo sapiens

<400> SEQUENCE: 86

```
Met Asp Met Arg Val Pro Ala Gln Leu Leu Gly Leu Leu Leu Leu Trp
1               5                   10                  15

Leu Pro Gly Ala Lys Cys
            20
```

<210> SEQ ID NO 87
<211> LENGTH: 20
<212> TYPE: PRT
<213> ORGANISM: Homo sapiens

<400> SEQUENCE: 87

```
Met Arg Leu Pro Ala Gln Leu Leu Gly Leu Leu Met Leu Trp Val Pro
```

```
1               5                   10                  15

Gly Ser Ser Glu
            20


<210> SEQ ID NO 88
<211> LENGTH: 20
<212> TYPE: PRT
<213> ORGANISM: Homo sapiens

<400> SEQUENCE: 88

Met Arg Leu Pro Ala Gln Leu Leu Gly Leu Leu Met Leu Trp Val Pro
1               5                   10                  15

Gly Ser Ser Glu
            20


<210> SEQ ID NO 89
<211> LENGTH: 20
<212> TYPE: PRT
<213> ORGANISM: Homo sapiens

<400> SEQUENCE: 89

Met Arg Leu Pro Ala Gln Leu Leu Gly Leu Leu Met Leu Trp Val Pro
1               5                   10                  15

Gly Ser Ser Gly
            20


<210> SEQ ID NO 90
<211> LENGTH: 20
<212> TYPE: PRT
<213> ORGANISM: Homo sapiens

<400> SEQUENCE: 90

Met Arg Leu Pro Ala Gln Leu Leu Gly Leu Leu Met Leu Trp Val Pro
1               5                   10                  15

Gly Ser Ser Gly
            20


<210> SEQ ID NO 91
<211> LENGTH: 20
<212> TYPE: PRT
<213> ORGANISM: Homo sapiens

<400> SEQUENCE: 91

Met Arg Leu Pro Ala Gln Leu Leu Gly Leu Leu Met Leu Trp Ile Pro
1               5                   10                  15

Gly Ser Ser Ala
            20


<210> SEQ ID NO 92
<211> LENGTH: 20
<212> TYPE: PRT
<213> ORGANISM: Homo sapiens

<400> SEQUENCE: 92

Met Arg Leu Pro Ala Gln Leu Leu Gly Leu Leu Met Leu Trp Ile Pro
1               5                   10                  15

Gly Ser Ser Ala
            20


<210> SEQ ID NO 93
<211> LENGTH: 20
<212> TYPE: PRT
```

<213> ORGANISM: Homo sapiens

<400> SEQUENCE: 93

Met Arg Leu Pro Ala Gln Leu Leu Gly Leu Leu Met Leu Trp Val Ser
1 5 10 15

Gly Ser Ser Gly
20

<210> SEQ ID NO 94
<211> LENGTH: 20
<212> TYPE: PRT
<213> ORGANISM: Homo sapiens

<400> SEQUENCE: 94

Met Arg Leu Pro Ala Gln Leu Leu Gly Leu Leu Met Leu Trp Val Ser
1 5 10 15

Gly Ser Ser Gly
20

<210> SEQ ID NO 95
<211> LENGTH: 20
<212> TYPE: PRT
<213> ORGANISM: Homo sapiens

<400> SEQUENCE: 95

Met Arg Leu Leu Ala Gln Leu Leu Gly Leu Leu Met Leu Trp Val Pro
1 5 10 15

Gly Ser Ser Gly
20

<210> SEQ ID NO 96
<211> LENGTH: 20
<212> TYPE: PRT
<213> ORGANISM: Homo sapiens

<400> SEQUENCE: 96

Met Glu Thr Pro Ala Gln Leu Leu Phe Leu Leu Leu Leu Trp Leu Pro
1 5 10 15

Asp Thr Thr Gly
20

<210> SEQ ID NO 97
<211> LENGTH: 20
<212> TYPE: PRT
<213> ORGANISM: Homo sapiens

<400> SEQUENCE: 97

Met Glu Thr Pro Ala Gln Leu Leu Phe Leu Leu Leu Leu Trp Leu Pro
1 5 10 15

Asp Thr Thr Gly
20

<210> SEQ ID NO 98
<211> LENGTH: 20
<212> TYPE: PRT
<213> ORGANISM: Homo sapiens

<400> SEQUENCE: 98

Met Glu Ala Pro Ala Gln Leu Leu Phe Leu Leu Leu Leu Trp Leu Pro
1 5 10 15

Asp Thr Thr Gly
20

<210> SEQ ID NO 99
<211> LENGTH: 20
<212> TYPE: PRT
<213> ORGANISM: Homo sapiens

<400> SEQUENCE: 99

Met Glu Ala Pro Ala Gln Leu Leu Phe Leu Leu Leu Leu Trp Leu Pro
1               5                   10                  15

Asp Thr Thr Gly
            20

<210> SEQ ID NO 100
<211> LENGTH: 20
<212> TYPE: PRT
<213> ORGANISM: Homo sapiens

<400> SEQUENCE: 100

Met Glu Ala Pro Ala Gln Leu Leu Phe Leu Leu Leu Leu Trp Leu Pro
1               5                   10                  15

Asp Thr Thr Gly
            20

<210> SEQ ID NO 101
<211> LENGTH: 20
<212> TYPE: PRT
<213> ORGANISM: Homo sapiens

<400> SEQUENCE: 101

Met Glu Ala Pro Ala Gln Leu Leu Phe Leu Leu Leu Leu Trp Leu Thr
1               5                   10                  15

Asp Thr Thr Gly
            20

<210> SEQ ID NO 102
<211> LENGTH: 23
<212> TYPE: PRT
<213> ORGANISM: Homo sapiens

<400> SEQUENCE: 102

Met Glu Pro Trp Lys Pro Gln His Ser Phe Phe Phe Leu Leu Leu Leu
1               5                   10                  15

Trp Leu Pro Asp Thr Thr Gly
            20

<210> SEQ ID NO 103
<211> LENGTH: 20
<212> TYPE: PRT
<213> ORGANISM: Homo sapiens

<400> SEQUENCE: 103

Met Val Leu Gln Thr Gln Val Phe Ile Ser Leu Leu Leu Trp Ile Ser
1               5                   10                  15

Gly Ala Tyr Gly
            20

<210> SEQ ID NO 104
<211> LENGTH: 20
<212> TYPE: PRT
<213> ORGANISM: Homo sapiens

<400> SEQUENCE: 104

```
Met Gly Ser Gln Val His Leu Leu Ser Phe Leu Leu Leu Trp Ile Ser
1               5                   10                  15

Asp Thr Arg Ala
            20


<210> SEQ ID NO 105
<211> LENGTH: 19
<212> TYPE: PRT
<213> ORGANISM: Homo sapiens

<400> SEQUENCE: 105

Met Leu Pro Ser Gln Leu Ile Gly Phe Leu Leu Leu Trp Val Pro Ala
1               5                   10                  15

Ser Arg Gly


<210> SEQ ID NO 106
<211> LENGTH: 19
<212> TYPE: PRT
<213> ORGANISM: Homo sapiens

<400> SEQUENCE: 106

Met Leu Pro Ser Gln Leu Ile Gly Phe Leu Leu Leu Trp Val Pro Ala
1               5                   10                  15

Ser Arg Gly


<210> SEQ ID NO 107
<211> LENGTH: 20
<212> TYPE: PRT
<213> ORGANISM: Homo sapiens

<400> SEQUENCE: 107

Met Val Ser Pro Leu Gln Phe Leu Arg Leu Leu Leu Leu Trp Val Pro
1               5                   10                  15

Ala Ser Arg Gly
            20


<210> SEQ ID NO 108
<211> LENGTH: 19
<212> TYPE: PRT
<213> ORGANISM: Homo sapiens

<400> SEQUENCE: 108

Met Ala Trp Ser Pro Leu Phe Leu Thr Leu Ile Thr His Cys Ala Gly
1               5                   10                  15

Ser Trp Ala


<210> SEQ ID NO 109
<211> LENGTH: 19
<212> TYPE: PRT
<213> ORGANISM: Homo sapiens

<400> SEQUENCE: 109

Met Ala Trp Ser Pro Leu Leu Leu Thr Leu Leu Ala His Cys Thr Gly
1               5                   10                  15

Ser Trp Ala


<210> SEQ ID NO 110
<211> LENGTH: 19
<212> TYPE: PRT
<213> ORGANISM: Homo sapiens

<400> SEQUENCE: 110
```

```
Met Ala Ser Phe Pro Leu Leu Leu Thr Leu Leu Thr His Cys Ala Gly
1               5                   10                  15

Ser Trp Ala


<210> SEQ ID NO 111
<211> LENGTH: 19
<212> TYPE: PRT
<213> ORGANISM: Homo sapiens

<400> SEQUENCE: 111

Met Ala Gly Phe Pro Leu Leu Leu Thr Leu Leu Thr His Cys Ala Gly
1               5                   10                  15

Ser Trp Ala


<210> SEQ ID NO 112
<211> LENGTH: 19
<212> TYPE: PRT
<213> ORGANISM: Homo sapiens

<400> SEQUENCE: 112

Met Thr Cys Ser Pro Leu Leu Leu Thr Leu Leu Ile His Cys Thr Gly
1               5                   10                  15

Ser Trp Ala


<210> SEQ ID NO 113
<211> LENGTH: 19
<212> TYPE: PRT
<213> ORGANISM: Homo sapiens

<400> SEQUENCE: 113

Met Ala Trp Ala Leu Leu Leu Leu Thr Leu Leu Thr Gln Gly Thr Gly
1               5                   10                  15

Ser Trp Ala


<210> SEQ ID NO 114
<211> LENGTH: 19
<212> TYPE: PRT
<213> ORGANISM: Homo sapiens

<400> SEQUENCE: 114

Met Ala Trp Ala Leu Leu Leu Leu Ser Leu Leu Thr Gln Gly Thr Gly
1               5                   10                  15

Ser Trp Ala


<210> SEQ ID NO 115
<211> LENGTH: 19
<212> TYPE: PRT
<213> ORGANISM: Homo sapiens

<400> SEQUENCE: 115

Met Ala Trp Ala Leu Leu Leu Leu Thr Leu Leu Thr Gln Gly Thr Gly
1               5                   10                  15

Ser Trp Ala


<210> SEQ ID NO 116
<211> LENGTH: 19
<212> TYPE: PRT
<213> ORGANISM: Homo sapiens

<400> SEQUENCE: 116
```

-continued

Met Ala Trp Ala Leu Leu Leu Leu Thr Leu Leu Thr Gln Gly Thr Gly
1 5 10 15

Ser Trp Ala

<210> SEQ ID NO 117
<211> LENGTH: 19
<212> TYPE: PRT
<213> ORGANISM: Homo sapiens

<400> SEQUENCE: 117

Met Ala Trp Ala Leu Leu Leu Leu Thr Leu Leu Thr Gln Asp Thr Gly
1 5 10 15

Ser Trp Ala

<210> SEQ ID NO 118
<211> LENGTH: 19
<212> TYPE: PRT
<213> ORGANISM: Homo sapiens

<400> SEQUENCE: 118

Met Ala Trp Ile Pro Leu Phe Leu Gly Val Leu Ala Tyr Cys Thr Gly
1 5 10 15

Ser Val Ala

<210> SEQ ID NO 119
<211> LENGTH: 19
<212> TYPE: PRT
<213> ORGANISM: Homo sapiens

<400> SEQUENCE: 119

Met Ala Trp Thr Ala Leu Leu Leu Ser Leu Leu Ala His Phe Thr Gly
1 5 10 15

Ser Val Ala

<210> SEQ ID NO 120
<211> LENGTH: 19
<212> TYPE: PRT
<213> ORGANISM: Homo sapiens

<400> SEQUENCE: 120

Met Ala Trp Thr Pro Leu Leu Leu Pro Leu Leu Thr Phe Cys Thr Val
1 5 10 15

Ser Glu Ala

<210> SEQ ID NO 121
<211> LENGTH: 19
<212> TYPE: PRT
<213> ORGANISM: Homo sapiens

<400> SEQUENCE: 121

Met Ala Trp Ile Pro Leu Leu Leu Pro Leu Leu Thr Leu Cys Thr Gly
1 5 10 15

Ser Glu Ala

<210> SEQ ID NO 122
<211> LENGTH: 19
<212> TYPE: PRT
<213> ORGANISM: Homo sapiens

<400> SEQUENCE: 122

Met Ala Trp Thr Pro Leu Trp Leu Thr Leu Leu Thr Leu Cys Ile Gly

```
1               5                   10                  15

Ser Val Val


<210> SEQ ID NO 123
<211> LENGTH: 19
<212> TYPE: PRT
<213> ORGANISM: Homo sapiens

<400> SEQUENCE: 123

Met Ala Trp Thr Val Leu Leu Leu Gly Leu Leu Ser His Cys Thr Gly
1               5                   10                  15

Ser Val Thr


<210> SEQ ID NO 124
<211> LENGTH: 19
<212> TYPE: PRT
<213> ORGANISM: Homo sapiens

<400> SEQUENCE: 124

Met Ala Trp Ala Thr Leu Leu Leu Pro Leu Leu Asn Leu Tyr Thr Gly
1               5                   10                  15

Ser Ile Ala


<210> SEQ ID NO 125
<211> LENGTH: 19
<212> TYPE: PRT
<213> ORGANISM: Homo sapiens

<400> SEQUENCE: 125

Met Ala Trp Ile Pro Leu Leu Leu Pro Leu Leu Thr Leu Cys Thr Gly
1               5                   10                  15

Ser Glu Ala


<210> SEQ ID NO 126
<211> LENGTH: 19
<212> TYPE: PRT
<213> ORGANISM: Homo sapiens

<400> SEQUENCE: 126

Met Ala Trp Ile Pro Leu Leu Leu Pro Leu Leu Ile Leu Cys Thr Val
1               5                   10                  15

Ser Val Ala


<210> SEQ ID NO 127
<211> LENGTH: 19
<212> TYPE: PRT
<213> ORGANISM: Homo sapiens

<400> SEQUENCE: 127

Met Ala Trp Val Ser Phe Tyr Leu Leu Pro Phe Ile Phe Ser Thr Gly
1               5                   10                  15

Leu Cys Ala


<210> SEQ ID NO 128
<211> LENGTH: 21
<212> TYPE: PRT
<213> ORGANISM: Homo sapiens

<400> SEQUENCE: 128

Met Ala Trp Thr Gln Leu Leu Leu Leu Phe Pro Leu Leu Leu His Trp
1               5                   10                  15
```

```
Thr Gly Ser Leu Ser
            20


<210> SEQ ID NO 129
<211> LENGTH: 20
<212> TYPE: PRT
<213> ORGANISM: Homo sapiens

<400> SEQUENCE: 129

Met Ala Trp Thr Pro Leu Leu Phe Leu Thr Leu Leu Leu His Cys Thr
1               5                   10                  15

Gly Ser Leu Ser
            20


<210> SEQ ID NO 130
<211> LENGTH: 19
<212> TYPE: PRT
<213> ORGANISM: Homo sapiens

<400> SEQUENCE: 130

Met Ala Trp Thr Pro Leu Leu Leu Leu Leu Leu Ser His Cys Thr Gly
1               5                   10                  15

Ser Leu Ser


<210> SEQ ID NO 131
<211> LENGTH: 19
<212> TYPE: PRT
<213> ORGANISM: Homo sapiens

<400> SEQUENCE: 131

Met Ala Trp Thr Pro Leu Leu Leu Leu Phe Leu Ser His Cys Thr Gly
1               5                   10                  15

Ser Leu Ser


<210> SEQ ID NO 132
<211> LENGTH: 19
<212> TYPE: PRT
<213> ORGANISM: Homo sapiens

<400> SEQUENCE: 132

Met Ala Trp Thr Leu Leu Leu Leu Val Leu Leu Ser His Cys Thr Gly
1               5                   10                  15

Ser Leu Ser


<210> SEQ ID NO 133
<211> LENGTH: 19
<212> TYPE: PRT
<213> ORGANISM: Homo sapiens

<400> SEQUENCE: 133

Met Ala Trp Ala Pro Leu Leu Leu Thr Leu Leu Ala His Cys Thr Gly
1               5                   10                  15

Ser Trp Ala


<210> SEQ ID NO 134
<211> LENGTH: 19
<212> TYPE: PRT
<213> ORGANISM: Homo sapiens

<400> SEQUENCE: 134

Met Ala Trp Thr Pro Leu Phe Leu Phe Leu Leu Thr Cys Cys Pro Gly
```

```
1               5                   10                  15

Ser Asn Ser


<210> SEQ ID NO 135
<211> LENGTH: 19
<212> TYPE: PRT
<213> ORGANISM: Homo sapiens

<400> SEQUENCE: 135

Met Ala Trp Thr Pro Leu Phe Leu Phe Leu Leu Thr Cys Cys Pro Gly
1               5                   10                  15

Ser Asn Ser


<210> SEQ ID NO 136
<211> LENGTH: 19
<212> TYPE: PRT
<213> ORGANISM: Homo sapiens

<400> SEQUENCE: 136

Met Ala Trp Met Met Leu Leu Leu Gly Leu Leu Ala Tyr Gly Ser Gly
1               5                   10                  15

Val Asp Ser


<210> SEQ ID NO 137
<211> LENGTH: 19
<212> TYPE: PRT
<213> ORGANISM: Homo sapiens

<400> SEQUENCE: 137

Met Ala Trp Ala Pro Leu Leu Leu Thr Leu Leu Ser Leu Leu Thr Gly
1               5                   10                  15

Ser Leu Ser


<210> SEQ ID NO 138
<211> LENGTH: 19
<212> TYPE: PRT
<213> ORGANISM: Homo sapiens

<400> SEQUENCE: 138

Met Pro Trp Ala Leu Leu Leu Leu Thr Leu Leu Thr His Ser Ala Val
1               5                   10                  15

Ser Val Val


<210> SEQ ID NO 139
<211> LENGTH: 18
<212> TYPE: PRT
<213> ORGANISM: Artificial
<220> FEATURE:
<223> OTHER INFORMATION: linker 6

<400> SEQUENCE: 139

Gly Gly Gly Gly Ser Gly Gly Gly Gly Ser Gly Gly Gly Gly Ser Gly
1               5                   10                  15

Ala Ser


<210> SEQ ID NO 140
<211> LENGTH: 19
<212> TYPE: PRT
<213> ORGANISM: Artificial
<220> FEATURE:
<223> OTHER INFORMATION: linker 7
```

<400> SEQUENCE: 140

Gly Ser Ser Ser Ser Ser Ser Ser Ser Ser Ser Ser Ser Ser Ser Ser
1 5 10 15

Gly Ala Ser

<210> SEQ ID NO 141
<211> LENGTH: 14
<212> TYPE: PRT
<213> ORGANISM: Mus musculus

<400> SEQUENCE: 141

Met Asp Phe Gly Leu Ile Phe Phe Ile Val Ala Leu Leu Lys
1 5 10

<210> SEQ ID NO 142
<211> LENGTH: 10
<212> TYPE: PRT
<213> ORGANISM: Mus musculus

<400> SEQUENCE: 142

Glu Leu Trp Val Leu Met Val Trp Val Pro
1 5 10

<210> SEQ ID NO 143
<211> LENGTH: 13
<212> TYPE: PRT
<213> ORGANISM: Mus musculus

<400> SEQUENCE: 143

Glu Leu Trp Val Leu Met Val Trp Val Pro Ser Thr Ser
1 5 10

<210> SEQ ID NO 144
<211> LENGTH: 18
<212> TYPE: PRT
<213> ORGANISM: Mus musculus

<400> SEQUENCE: 144

His Asp His Ala Leu Thr Ser Ser Ser Pro Gln Pro Ser Ser Pro Leu
1 5 10 15

Cys Leu

<210> SEQ ID NO 145
<211> LENGTH: 16
<212> TYPE: PRT
<213> ORGANISM: Mus musculus

<400> SEQUENCE: 145

Leu Ala Val Ile Thr Ser Asn Ile Trp Phe Pro Met Val Cys Met Ser
1 5 10 15

<210> SEQ ID NO 146
<211> LENGTH: 21
<212> TYPE: PRT
<213> ORGANISM: Mus musculus

<400> SEQUENCE: 146

Met Asp Met Trp Thr Ser Ala Gln Phe Leu Gly Ile Leu Leu Leu Trp
1 5 10 15

Phe Leu Ala Arg Cys
20

<210> SEQ ID NO 147
<211> LENGTH: 18
<212> TYPE: PRT
<213> ORGANISM: Mus musculus

<400> SEQUENCE: 147

```
Met Asp Arg Leu Thr Ser Ser Phe Leu Leu Leu Ile Val Pro Ala Val
1               5                   10                  15

Leu Ser
```

<210> SEQ ID NO 148
<211> LENGTH: 16
<212> TYPE: PRT
<213> ORGANISM: Mus musculus

<400> SEQUENCE: 148

```
Met Leu Arg Ala Ile Lys Ala Ala Pro Phe Ser Arg Phe Gly Cys Ser
1               5                   10                  15
```

<210> SEQ ID NO 149
<211> LENGTH: 19
<212> TYPE: PRT
<213> ORGANISM: Mus musculus

<400> SEQUENCE: 149

```
Met Arg Ala Pro Ala Pro Phe Leu Gly Leu Leu Leu Phe Cys Phe Leu
1               5                   10                  15

Ala Arg Cys
```

<210> SEQ ID NO 150
<211> LENGTH: 16
<212> TYPE: PRT
<213> ORGANISM: Mus musculus

<400> SEQUENCE: 150

```
Met Arg Cys Ser Pro His Phe Leu Glu Leu Leu Val Phe Trp Ile Leu
1               5                   10                  15
```

<210> SEQ ID NO 151
<211> LENGTH: 19
<212> TYPE: PRT
<213> ORGANISM: Mus musculus

<400> SEQUENCE: 151

```
Met Arg Pro Thr Leu Ser Phe Leu Gly Ser Cys Cys Ser Ser Leu Ile
1               5                   10                  15

Leu Arg Cys
```

<210> SEQ ID NO 152
<211> LENGTH: 19
<212> TYPE: PRT
<213> ORGANISM: Mus musculus

<400> SEQUENCE: 152

```
Met Arg Thr Pro Ala His Phe Leu Gly Leu Leu Leu Leu Cys Phe Leu
1               5                   10                  15

Gly Arg Cys
```

<210> SEQ ID NO 153
<211> LENGTH: 19
<212> TYPE: PRT
<213> ORGANISM: Mus musculus

<400> SEQUENCE: 153

Met Arg Thr Pro Ala Pro Phe Leu Gly Leu Leu Leu Phe Cys Phe Ser
1 5 10 15

Ala Arg Cys

<210> SEQ ID NO 154
<211> LENGTH: 19
<212> TYPE: PRT
<213> ORGANISM: Mus musculus

<400> SEQUENCE: 154

Met Ser Leu Leu Thr Gln Leu Gln Gly Leu Leu Leu Leu Trp Leu Thr
1 5 10 15

Asp Arg Cys

<210> SEQ ID NO 155
<211> LENGTH: 19
<212> TYPE: PRT
<213> ORGANISM: Mus musculus

<400> SEQUENCE: 155

Met Ser Leu Pro Thr Gln Leu Gln Gly Leu Leu Leu Leu Trp Leu Thr
1 5 10 15

Ala Arg Cys

<210> SEQ ID NO 156
<211> LENGTH: 18
<212> TYPE: PRT
<213> ORGANISM: Mus musculus

<400> SEQUENCE: 156

Met Thr Met Leu Ser Leu Ala Pro Leu Leu Ser Leu Leu Leu Leu Cys
1 5 10 15

Val Ser

<210> SEQ ID NO 157
<211> LENGTH: 16
<212> TYPE: PRT
<213> ORGANISM: Mus musculus

<400> SEQUENCE: 157

Met Thr Ser Leu Ser Gln Leu Leu Gly Met Leu Met Leu Gln Ser Leu
1 5 10 15

<210> SEQ ID NO 158
<211> LENGTH: 16
<212> TYPE: PRT
<213> ORGANISM: Mus musculus

<400> SEQUENCE: 158

Met Val Phe Ala Pro Gln Ile Leu Gly Phe Leu Leu Leu Trp Ile Ser
1 5 10 15

<210> SEQ ID NO 159
<211> LENGTH: 16
<212> TYPE: PRT
<213> ORGANISM: Mus musculus

<400> SEQUENCE: 159

Met Val Phe Thr Pro His Ile Leu Gly Leu Leu Leu Phe Trp Ile Ser
1 5 10 15

<210> SEQ ID NO 160
<211> LENGTH: 19
<212> TYPE: PRT
<213> ORGANISM: Mus musculus

<400> SEQUENCE: 160

Gln His Gly His Glu Gly Leu Cys Ser Val Ser Trp Val Pro Val Ala
1 5 10 15

Thr Asn Ser

<210> SEQ ID NO 161
<211> LENGTH: 18
<212> TYPE: PRT
<213> ORGANISM: Mus musculus

<400> SEQUENCE: 161

Arg Glu Trp Ser Trp Asn Phe Leu Phe Leu Leu Ser Gly Thr Thr Val
1 5 10 15

Ser Ser

<210> SEQ ID NO 162
<211> LENGTH: 19
<212> TYPE: PRT
<213> ORGANISM: Mus musculus

<400> SEQUENCE: 162

Thr Asp Phe His Met Gln Ile Phe Ser Phe Met Leu Ile Ser Phe Thr
1 5 10 15

Ala Arg Cys

<210> SEQ ID NO 163
<211> LENGTH: 16
<212> TYPE: PRT
<213> ORGANISM: Mus musculus

<400> SEQUENCE: 163

Met Glu Phe Gln Thr Gln Val Leu Met Ser Leu Leu Leu Cys Met Ser
1 5 10 15

<210> SEQ ID NO 164
<211> LENGTH: 16
<212> TYPE: PRT
<213> ORGANISM: Mus musculus

<400> SEQUENCE: 164

Met Glu Ser Gln Thr Gln Val Leu Met Phe Leu Leu Leu Trp Val Ser
1 5 10 15

<210> SEQ ID NO 165
<211> LENGTH: 16
<212> TYPE: PRT
<213> ORGANISM: Mus musculus

<400> SEQUENCE: 165

Met Val Ser Thr Pro Gln Phe Leu Val Phe Leu Leu Phe Trp Ile Pro
1 5 10 15

<210> SEQ ID NO 166
<211> LENGTH: 16
<212> TYPE: PRT
<213> ORGANISM: Mus musculus

<400> SEQUENCE: 166

Met Val Ser Thr Pro Gln Phe Leu Val Phe Leu Leu Phe Trp Ile Pro
1               5                   10                  15

<210> SEQ ID NO 167
<211> LENGTH: 16
<212> TYPE: PRT
<213> ORGANISM: Mus musculus

<400> SEQUENCE: 167

Met Ser Val Pro Thr Gln Leu Leu Gly Leu Leu Leu Leu Trp Leu Thr
1               5                   10                  15

<210> SEQ ID NO 168
<211> LENGTH: 16
<212> TYPE: PRT
<213> ORGANISM: Mus musculus

<400> SEQUENCE: 168

Met Lys Ser Gln Thr Gln Val Phe Ile Phe Leu Leu Leu Cys Val Ser
1               5                   10                  15

<210> SEQ ID NO 169
<211> LENGTH: 16
<212> TYPE: PRT
<213> ORGANISM: Mus musculus

<400> SEQUENCE: 169

Met Lys Ser Gln Thr Gln Val Phe Val Phe Leu Leu Leu Cys Val Ser
1               5                   10                  15

<210> SEQ ID NO 170
<211> LENGTH: 15
<212> TYPE: PRT
<213> ORGANISM: Mus musculus

<400> SEQUENCE: 170

Met Ala Trp Ile Ser Leu Ile Leu Ser Leu Leu Ala Leu Ser Ser
1               5                   10                  15

<210> SEQ ID NO 171
<211> LENGTH: 15
<212> TYPE: PRT
<213> ORGANISM: Mus musculus

<400> SEQUENCE: 171

Met Ala Trp Thr Ser Leu Ile Leu Ser Leu Leu Ala Leu Cys Ser
1               5                   10                  15

<210> SEQ ID NO 172
<211> LENGTH: 16
<212> TYPE: PRT
<213> ORGANISM: Mus musculus

<400> SEQUENCE: 172

Met Arg Cys Leu Ala Glu Phe Leu Gly Leu Leu Val Leu Trp Ile Pro
1               5                   10                  15

<210> SEQ ID NO 173
<211> LENGTH: 15
<212> TYPE: PRT
<213> ORGANISM: Mus musculus

<400> SEQUENCE: 173

Met Gly Trp Asn Trp Ile Phe Ile Leu Ile Leu Ser Val Thr Thr 1 5 10 15

<210> SEQ ID NO 174
<211> LENGTH: 16
<212> TYPE: PRT
<213> ORGANISM: Mus musculus

<400> SEQUENCE: 174

Met Arg Phe Gln Val Gln Val Leu Gly Leu Leu Leu Leu Trp Ile Ser
1 5 10 15

<210> SEQ ID NO 175
<211> LENGTH: 16
<212> TYPE: PRT
<213> ORGANISM: Mus musculus

<400> SEQUENCE: 175

Met Arg Pro Ser Ile Gln Phe Leu Gly Leu Leu Leu Phe Trp Leu His
1 5 10 15

<210> SEQ ID NO 176
<211> LENGTH: 18
<212> TYPE: PRT
<213> ORGANISM: Mus musculus

<400> SEQUENCE: 176

Met Asp Ile Arg Ala Pro Ala Gln Phe Leu Gly Ile Leu Leu Leu Trp
1 5 10 15

Phe Pro

<210> SEQ ID NO 177
<211> LENGTH: 18
<212> TYPE: PRT
<213> ORGANISM: Mus musculus

<400> SEQUENCE: 177

Met Asp Met Met Val Leu Ala Gln Phe Leu Ala Phe Leu Leu Leu Trp
1 5 10 15

Phe Pro

<210> SEQ ID NO 178
<211> LENGTH: 18
<212> TYPE: PRT
<213> ORGANISM: Mus musculus

<400> SEQUENCE: 178

Met Asp Met Arg Ala Pro Ala Gln Phe Leu Gly Ile Leu Leu Leu Trp
1 5 10 15

Phe Pro

<210> SEQ ID NO 179
<211> LENGTH: 18
<212> TYPE: PRT
<213> ORGANISM: Mus musculus

<400> SEQUENCE: 179

Met Asp Met Arg Ala Pro Ala Gln Phe Leu Gly Ile Leu Leu Leu Trp
1 5 10 15

Phe Pro

<210> SEQ ID NO 180
<211> LENGTH: 18

<212> TYPE: PRT
<213> ORGANISM: Mus musculus

<400> SEQUENCE: 180

Met Asp Met Arg Ala Pro Ala Gln Val Phe Gly Phe Leu Leu Leu Trp
1 5 10 15

Phe Pro

<210> SEQ ID NO 181
<211> LENGTH: 18
<212> TYPE: PRT
<213> ORGANISM: Mus musculus

<400> SEQUENCE: 181

Met Asp Met Arg Ala Ser Ala Gln Phe His Gly Ile Leu Leu Leu Trp
1 5 10 15

Phe Pro

<210> SEQ ID NO 182
<211> LENGTH: 18
<212> TYPE: PRT
<213> ORGANISM: Mus musculus

<400> SEQUENCE: 182

Met Asp Met Arg Ala Ser Ala Gln Phe His Gly Ile Leu Leu Leu Trp
1 5 10 15

Phe Pro

<210> SEQ ID NO 183
<211> LENGTH: 18
<212> TYPE: PRT
<213> ORGANISM: Mus musculus

<400> SEQUENCE: 183

Met Asp Met Trp Thr Ser Ala Gln Phe Leu Gly Ile Leu Leu Leu Trp
1 5 10 15

Phe Leu

<210> SEQ ID NO 184
<211> LENGTH: 18
<212> TYPE: PRT
<213> ORGANISM: Mus musculus

<400> SEQUENCE: 184

Met Asn Thr Arg Ala Pro Ala Glu Phe Leu Gly Phe Leu Leu Leu Trp
1 5 10 15

Phe Leu

<210> SEQ ID NO 185
<211> LENGTH: 16
<212> TYPE: PRT
<213> ORGANISM: Mus musculus

<400> SEQUENCE: 185

Met Arg Ala Pro Ala Pro Phe Leu Gly Leu Leu Leu Phe Cys Phe Leu
1 5 10 15

<210> SEQ ID NO 186
<211> LENGTH: 16
<212> TYPE: PRT
<213> ORGANISM: Mus musculus

<400> SEQUENCE: 186

Met Arg Thr Pro Ala Pro Phe Leu Gly Leu Leu Leu Phe Cys Phe Ser
1 5 10 15

<210> SEQ ID NO 187
<211> LENGTH: 16
<212> TYPE: PRT
<213> ORGANISM: Mus musculus

<400> SEQUENCE: 187

Met Ser Ile Ser Thr Gln Leu Leu Gly Leu Leu Leu Leu Trp Leu Thr
1 5 10 15

<210> SEQ ID NO 188
<211> LENGTH: 16
<212> TYPE: PRT
<213> ORGANISM: Mus musculus

<400> SEQUENCE: 188

Met Ser Leu Pro Thr Gln Leu Gln Gly Leu Leu Leu Leu Trp Leu Thr
1 5 10 15

<210> SEQ ID NO 189
<211> LENGTH: 16
<212> TYPE: PRT
<213> ORGANISM: Mus musculus

<400> SEQUENCE: 189

Met Ser Val Leu Thr Gln Val Leu Ala Leu Leu Leu Leu Trp Leu Thr
1 5 10 15

<210> SEQ ID NO 190
<211> LENGTH: 16
<212> TYPE: PRT
<213> ORGANISM: Mus musculus

<400> SEQUENCE: 190

Met Ser Val Pro Thr Gln Leu Leu Ala Leu Leu Leu Leu Trp Leu Thr
1 5 10 15

<210> SEQ ID NO 191
<211> LENGTH: 16
<212> TYPE: PRT
<213> ORGANISM: Mus musculus

<400> SEQUENCE: 191

Met Ser Val Pro Thr Gln Val Leu Gly Leu Leu Leu Leu Trp Leu Thr
1 5 10 15

<210> SEQ ID NO 192
<211> LENGTH: 16
<212> TYPE: PRT
<213> ORGANISM: Mus musculus

<400> SEQUENCE: 192

Thr Asp Phe His Met Gln Ile Phe Ser Phe Met Leu Ile Ser Phe Thr
1 5 10 15

<210> SEQ ID NO 193
<211> LENGTH: 15
<212> TYPE: PRT
<213> ORGANISM: Mus musculus

<400> SEQUENCE: 193

```
Met Ala Trp Thr Ser Leu Ile Leu Ser Leu Leu Ala Leu Cys Ser
1               5                   10                  15


<210> SEQ ID NO 194
<211> LENGTH: 16
<212> TYPE: PRT
<213> ORGANISM: Mus musculus

<400> SEQUENCE: 194

Met Arg Cys Leu Ala Glu Phe Leu Arg Leu Leu Val Leu Trp Ile Pro
1               5                   10                  15


<210> SEQ ID NO 195
<211> LENGTH: 18
<212> TYPE: PRT
<213> ORGANISM: Mus musculus

<400> SEQUENCE: 195

Met Lys Leu Pro Val Arg Leu Leu Val Leu Met Phe Trp Ile Pro Ser
1               5                   10                  15

Ser Ser


<210> SEQ ID NO 196
<211> LENGTH: 21
<212> TYPE: PRT
<213> ORGANISM: Mus musculus

<400> SEQUENCE: 196

Met Asp Ile Arg Ala Pro Ala Gln Phe Leu Gly Ile Leu Leu Leu Trp
1               5                   10                  15

Phe Pro Ala Arg Cys
            20


<210> SEQ ID NO 197
<211> LENGTH: 21
<212> TYPE: PRT
<213> ORGANISM: Mus musculus

<400> SEQUENCE: 197

Met Asp Met Met Val Leu Ala Gln Phe Leu Ala Phe Leu Leu Leu Trp
1               5                   10                  15

Phe Pro Ala Arg Cys
            20


<210> SEQ ID NO 198
<211> LENGTH: 21
<212> TYPE: PRT
<213> ORGANISM: Mus musculus

<400> SEQUENCE: 198

Met Asp Met Arg Ala Pro Ala Gln Phe Phe Gly Ile Leu Leu Leu Trp
1               5                   10                  15

Phe Pro Ile Arg Cys
            20


<210> SEQ ID NO 199
<211> LENGTH: 21
<212> TYPE: PRT
<213> ORGANISM: Mus musculus

<400> SEQUENCE: 199

Met Asp Met Arg Ala Pro Ala Gln Phe Leu Gly Ile Leu Leu Leu Trp
1               5                   10                  15
```

-continued

Phe Pro Ala Arg Cys
20

<210> SEQ ID NO 200
<211> LENGTH: 21
<212> TYPE: PRT
<213> ORGANISM: Mus musculus

<400> SEQUENCE: 200

Met Asp Met Arg Ala Pro Ala Gln Ile Phe Gly Phe Leu Leu Leu Leu
1 5 10 15

Phe Gln Thr Arg Cys
20

<210> SEQ ID NO 201
<211> LENGTH: 21
<212> TYPE: PRT
<213> ORGANISM: Mus musculus

<400> SEQUENCE: 201

Met Asp Met Arg Ala Pro Ala Gln Val Phe Gly Phe Leu Leu Leu Trp
1 5 10 15

Phe Pro Ala Arg Cys
20

<210> SEQ ID NO 202
<211> LENGTH: 18
<212> TYPE: PRT
<213> ORGANISM: Mus musculus

<400> SEQUENCE: 202

Met Asp Met Arg Ala Ser Ala Gln Phe Leu Gly Phe Leu Leu Leu Trp
1 5 10 15

Phe Pro

<210> SEQ ID NO 203
<211> LENGTH: 18
<212> TYPE: PRT
<213> ORGANISM: Mus musculus

<400> SEQUENCE: 203

Met Asp Met Arg Asp Pro Pro Gln Phe Leu Ala Phe Leu Leu Leu Trp
1 5 10 15

Ile Pro

<210> SEQ ID NO 204
<211> LENGTH: 21
<212> TYPE: PRT
<213> ORGANISM: Mus musculus

<400> SEQUENCE: 204

Met Asp Met Arg Thr Pro Ala Gln Phe Leu Gly Ile Leu Leu Leu Trp
1 5 10 15

Phe Pro Ile Lys Cys
20

<210> SEQ ID NO 205
<211> LENGTH: 21
<212> TYPE: PRT
<213> ORGANISM: Mus musculus

<400> SEQUENCE: 205

Met Asp Met Arg Val Pro Ala His Val Phe Gly Phe Leu Leu Leu Trp
1 5 10 15

Phe Pro Thr Arg Cys
20

<210> SEQ ID NO 206
<211> LENGTH: 19
<212> TYPE: PRT
<213> ORGANISM: Mus musculus

<400> SEQUENCE: 206

Met Asp Ser Gln Ala Gln Val Leu Ile Leu Leu Leu Leu Trp Val Ser
1 5 10 15

Thr Cys Gly

<210> SEQ ID NO 207
<211> LENGTH: 19
<212> TYPE: PRT
<213> ORGANISM: Mus musculus

<400> SEQUENCE: 207

Met Asp Ser Gln Ala Gln Val Leu Met Leu Leu Leu Leu Ser Val Ser
1 5 10 15

Thr Cys Gly

<210> SEQ ID NO 208
<211> LENGTH: 19
<212> TYPE: PRT
<213> ORGANISM: Mus musculus

<400> SEQUENCE: 208

Met Asp Ser Gln Ala Gln Val Leu Met Leu Leu Leu Leu Trp Val Ser
1 5 10 15

Thr Cys Gly

<210> SEQ ID NO 209
<211> LENGTH: 19
<212> TYPE: PRT
<213> ORGANISM: Mus musculus

<400> SEQUENCE: 209

Met Asp Ser Gln Ala Arg Val Leu Met Leu Leu Leu Leu Trp Val Ser
1 5 10 15

Thr Cys Gly

<210> SEQ ID NO 210
<211> LENGTH: 19
<212> TYPE: PRT
<213> ORGANISM: Mus musculus

<400> SEQUENCE: 210

Met Glu Phe Gln Thr Gln Val Phe Val Phe Val Leu Leu Trp Leu Ser
1 5 10 15

Val Asp Gly

<210> SEQ ID NO 211
<211> LENGTH: 19
<212> TYPE: PRT
<213> ORGANISM: Mus musculus

<400> SEQUENCE: 211

-continued

```
Met Glu Phe Gln Thr Gln Val Leu Met Ser Leu Leu Leu Cys Met Ser
1               5                   10                  15

Ala Cys Ala


<210> SEQ ID NO 212
<211> LENGTH: 19
<212> TYPE: PRT
<213> ORGANISM: Mus musculus

<400> SEQUENCE: 212

Met Glu Lys Asp Thr Leu Leu Leu Trp Val Leu Leu Leu Trp Val Pro
1               5                   10                  15

Ser Thr Gly


<210> SEQ ID NO 213
<211> LENGTH: 19
<212> TYPE: PRT
<213> ORGANISM: Mus musculus

<400> SEQUENCE: 213

Met Glu Ser Asp Thr Leu Leu Leu Trp Val Leu Leu Leu Trp Val Pro
1               5                   10                  15

Ser Thr Gly


<210> SEQ ID NO 214
<211> LENGTH: 19
<212> TYPE: PRT
<213> ORGANISM: Mus musculus

<400> SEQUENCE: 214

Met Glu Ser Gln Ile Gln Ala Phe Val Phe Val Phe Leu Trp Leu Ser
1               5                   10                  15

Val Asp Gly


<210> SEQ ID NO 215
<211> LENGTH: 19
<212> TYPE: PRT
<213> ORGANISM: Mus musculus

<400> SEQUENCE: 215

Met Glu Ser Gln Ile Gln Val Phe Val Phe Val Phe Leu Trp Leu Ser
1               5                   10                  15

Val Asp Gly


<210> SEQ ID NO 216
<211> LENGTH: 16
<212> TYPE: PRT
<213> ORGANISM: Mus musculus

<400> SEQUENCE: 216

Met Ser Leu Leu Thr Gln Leu Gln Gly Leu Leu Leu Leu Trp Leu Thr
1               5                   10                  15


<210> SEQ ID NO 217
<211> LENGTH: 7
<212> TYPE: PRT
<213> ORGANISM: Mus musculus

<400> SEQUENCE: 217

Leu Ile Leu Lys Val Gln Cys
1               5
```

<210> SEQ ID NO 218
<211> LENGTH: 7
<212> TYPE: PRT
<213> ORGANISM: Mus musculus

<400> SEQUENCE: 218

```
Leu Val Leu Lys Val Leu Cys
1               5
```

<210> SEQ ID NO 219
<211> LENGTH: 21
<212> TYPE: PRT
<213> ORGANISM: Mus musculus

<400> SEQUENCE: 219

```
Met Asp Met Arg Ala Ser Ala Gln Phe His Gly Ile Leu Leu Leu Trp
1               5                   10                  15

Phe Pro Ala Arg Cys
            20
```

<210> SEQ ID NO 220
<211> LENGTH: 19
<212> TYPE: PRT
<213> ORGANISM: Mus musculus

<400> SEQUENCE: 220

```
Met Lys Leu Pro Val Leu Leu Val Val Leu Leu Leu Phe Thr Ser Pro
1               5                   10                  15

Ser Ser Ser
```

<210> SEQ ID NO 221
<211> LENGTH: 18
<212> TYPE: PRT
<213> ORGANISM: Mus musculus

<400> SEQUENCE: 221

```
Met Lys Leu Pro Val Arg Leu Leu Val Leu Met Phe Trp Ile Pro Ser
1               5                   10                  15

Ser Ser
```

<210> SEQ ID NO 222
<211> LENGTH: 19
<212> TYPE: PRT
<213> ORGANISM: Mus musculus

<400> SEQUENCE: 222

```
Met Met Ser Pro Ala Gln Phe Leu Phe Leu Leu Val Leu Trp Ile Gln
1               5                   10                  15

Thr Asn Gly
```

<210> SEQ ID NO 223
<211> LENGTH: 19
<212> TYPE: PRT
<213> ORGANISM: Mus musculus

<400> SEQUENCE: 223

```
Met Met Ser Pro Ala Gln Phe Leu Phe Leu Leu Val Leu Trp Ile Arg
1               5                   10                  15

Thr Asn Gly
```

<210> SEQ ID NO 224
<211> LENGTH: 19
<212> TYPE: PRT
<213> ORGANISM: Mus musculus

<400> SEQUENCE: 224

```
Met Met Ser Pro Val His Ser Ile Phe Ile Leu Leu Leu Trp Ile Val
1               5                   10                  15

Ile Ser Gly
```

<210> SEQ ID NO 225
<211> LENGTH: 19
<212> TYPE: PRT
<213> ORGANISM: Mus musculus

<400> SEQUENCE: 225

```
Met Met Ser Pro Val Gln Phe Leu Phe Leu Leu Met Leu Trp Ile Gln
1               5                   10                  15

Thr Asn Gly
```

<210> SEQ ID NO 226
<211> LENGTH: 18
<212> TYPE: PRT
<213> ORGANISM: Mus musculus

<400> SEQUENCE: 226

```
Met Asn Phe Gly Leu Arg Leu Ile Phe Leu Val Leu Thr Leu Lys Val
1               5                   10                  15

Gln Cys
```

<210> SEQ ID NO 227
<211> LENGTH: 19
<212> TYPE: PRT
<213> ORGANISM: Mus musculus

<400> SEQUENCE: 227

```
Met Asn Leu Pro Val His Leu Leu Val Leu Leu Leu Phe Trp Ile Pro
1               5                   10                  15

Ser Arg Gly
```

<210> SEQ ID NO 228
<211> LENGTH: 21
<212> TYPE: PRT
<213> ORGANISM: Mus musculus

<400> SEQUENCE: 228

```
Met Asn Thr Arg Ala Pro Ala Glu Phe Leu Gly Phe Leu Leu Leu Trp
1               5                   10                  15

Phe Leu Ala Arg Cys
            20
```

<210> SEQ ID NO 229
<211> LENGTH: 19
<212> TYPE: PRT
<213> ORGANISM: Mus musculus

<400> SEQUENCE: 229

```
Met Arg Phe Gln Val Gln Val Leu Gly Leu Leu Leu Leu Trp Ile Ser
1               5                   10                  15

Ala Gln Cys
```

<210> SEQ ID NO 230
<211> LENGTH: 18
<212> TYPE: PRT
<213> ORGANISM: Mus musculus

<400> SEQUENCE: 230

Met Arg Val Leu Ser Leu Leu Tyr Leu Leu Thr Ala Ile Pro Gly Ile
1 5 10 15

Leu Ser

<210> SEQ ID NO 231
<211> LENGTH: 21
<212> TYPE: PRT
<213> ORGANISM: Mus musculus

<400> SEQUENCE: 231

Met Asp Phe His Val Gln Ile Phe Ser Phe Met Leu Ile Ser Val Thr
1 5 10 15

Ile Leu Ser Ser Gly
20

<210> SEQ ID NO 232
<211> LENGTH: 21
<212> TYPE: PRT
<213> ORGANISM: Mus musculus

<400> SEQUENCE: 232

Met Asp Phe Gln Met Gln Ile Ile Ser Leu Leu Leu Ile Ser Val Thr
1 5 10 15

Ile Val Ser Asn Gly
20

<210> SEQ ID NO 233
<211> LENGTH: 21
<212> TYPE: PRT
<213> ORGANISM: Mus musculus

<400> SEQUENCE: 233

Met Asp Phe Gln Val Gln Ile Phe Ser Phe Leu Leu Ile Ser Val Thr
1 5 10 15

Ile Leu Thr Asn Gly
20

<210> SEQ ID NO 234
<211> LENGTH: 21
<212> TYPE: PRT
<213> ORGANISM: Mus musculus

<400> SEQUENCE: 234

Met Asp Met Arg Ala Pro Ala Gln Phe Leu Gly Ile Leu Leu Leu Trp
1 5 10 15

Phe Pro Ala Arg Cys
20

<210> SEQ ID NO 235
<211> LENGTH: 21
<212> TYPE: PRT
<213> ORGANISM: Mus musculus

<400> SEQUENCE: 235

Met Asn Phe His Val Gln Ile Phe Ser Phe Met Leu Ile Ser Val Thr
1 5 10 15

-continued

```
Ile Gly Ser Ser Gly
            20


<210> SEQ ID NO 236
<211> LENGTH: 19
<212> TYPE: PRT
<213> ORGANISM: Mus musculus

<400> SEQUENCE: 236

Met Thr Met Leu Ser Leu Val Leu Leu Leu Ser Phe Leu Leu Leu Cys
1               5                   10                  15

Ser Arg Ala


<210> SEQ ID NO 237
<211> LENGTH: 19
<212> TYPE: PRT
<213> ORGANISM: Mus musculus

<400> SEQUENCE: 237

Met Val Ser Thr Pro Gln Phe Leu Val Phe Leu Leu Phe Trp Ile Pro
1               5                   10                  15

Ala Cys Gly


<210> SEQ ID NO 238
<211> LENGTH: 20
<212> TYPE: PRT
<213> ORGANISM: Mus musculus

<400> SEQUENCE: 238

Thr Glu Leu Ile Cys Val Phe Leu Phe Leu Leu Ser Val Thr Ala Ile
1               5                   10                  15

Leu Ser Ser Gly
            20


<210> SEQ ID NO 239
<211> LENGTH: 17
<212> TYPE: PRT
<213> ORGANISM: Mus musculus

<400> SEQUENCE: 239

Met Asp Cys Gly Ile Ser Leu Val Phe Leu Val Leu Ile Leu Lys Val
1               5                   10                  15

Cys


<210> SEQ ID NO 240
<211> LENGTH: 19
<212> TYPE: PRT
<213> ORGANISM: Mus musculus

<400> SEQUENCE: 240

Met Asp Met Trp Val Gln Ile Phe Ser Leu Leu Leu Ile Cys Val Thr
1               5                   10                  15

Ser Lys Gly


<210> SEQ ID NO 241
<211> LENGTH: 11
<212> TYPE: PRT
<213> ORGANISM: Mus musculus

<400> SEQUENCE: 241

Leu Leu Ile Ser Val Thr Ile Met Ser Arg Gly
1               5                   10
```

<210> SEQ ID NO 242
<211> LENGTH: 21
<212> TYPE: PRT
<213> ORGANISM: Mus musculus

<400> SEQUENCE: 242

```
Met Asp Phe Gln Val Gln Ile Phe Ser Phe Leu Leu Ile Ser Ala Ser
1               5                   10                  15

Ile Met Ser Arg Gly
            20
```

<210> SEQ ID NO 243
<211> LENGTH: 21
<212> TYPE: PRT
<213> ORGANISM: Mus musculus

<400> SEQUENCE: 243

```
Met Asp Phe Gln Val Gln Ile Phe Ser Phe Leu Leu Ile Ser Ile Ser
1               5                   10                  15

Val Met Ser Arg Gly
            20
```

<210> SEQ ID NO 244
<211> LENGTH: 21
<212> TYPE: PRT
<213> ORGANISM: Mus musculus

<400> SEQUENCE: 244

```
Met Asp Phe Gln Val Gln Ile Phe Ser Phe Leu Leu Ile Ser Val Ser
1               5                   10                  15

Ile Met Ser Arg Gly
            20
```

<210> SEQ ID NO 245
<211> LENGTH: 21
<212> TYPE: PRT
<213> ORGANISM: Mus musculus

<400> SEQUENCE: 245

```
Met Asp Leu Gln Val Gln Ile Ile Ser Phe Leu Leu Ile Ile Val Thr
1               5                   10                  15

Ile Met Ser Arg Gly
            20
```

<210> SEQ ID NO 246
<211> LENGTH: 19
<212> TYPE: PRT
<213> ORGANISM: Mus musculus

<400> SEQUENCE: 246

```
Met Gly Glu Gln Arg Ile Arg Ser Cys His Ala Thr Ser Gly Ala Glu
1               5                   10                  15

Ser Ala Arg
```

<210> SEQ ID NO 247
<211> LENGTH: 20
<212> TYPE: PRT
<213> ORGANISM: Mus musculus

<400> SEQUENCE: 247

```
Met Gly Ser Gln Val His Leu Leu Ser Phe Leu Leu Leu Trp Ile Ser
```

```
1               5                   10                  15

Asp Thr Arg Ala
            20


<210> SEQ ID NO 248
<211> LENGTH: 21
<212> TYPE: PRT
<213> ORGANISM: Mus musculus

<400> SEQUENCE: 248

Met Thr Met Phe Ser Leu Ala Leu Leu Leu Ser Leu Leu Leu Leu Cys
1               5                   10                  15

Val Ser Ser Arg Ala
            20


<210> SEQ ID NO 249
<211> LENGTH: 18
<212> TYPE: PRT
<213> ORGANISM: Mus musculus

<400> SEQUENCE: 249

Met Thr Met Leu Ser Leu Ala Pro Leu Leu Ser Leu Leu Leu Leu Ser
1               5                   10                  15

Arg Ala


<210> SEQ ID NO 250
<211> LENGTH: 22
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 250

Met Xaa Thr Met Asp Glu His Glu Ser Gly Ala Val Thr Pro His Gln
1               5                   10                  15

Val Leu Lys Ser Arg Ala
            20


<210> SEQ ID NO 251
<211> LENGTH: 18
<212> TYPE: PRT
<213> ORGANISM: Mus musculus

<400> SEQUENCE: 251

Ile Lys Trp Ser Trp Ile Phe Leu Phe Leu Leu Ser Gly Thr Ala Val
1               5                   10                  15

His Ser


<210> SEQ ID NO 252
<211> LENGTH: 18
<212> TYPE: PRT
<213> ORGANISM: Mus musculus

<400> SEQUENCE: 252

Ile Lys Trp Ser Trp Ile Ser Leu Phe Leu Leu Ser Gly Thr Ala Val
1               5                   10                  15

His Ser


<210> SEQ ID NO 253
<211> LENGTH: 7
```

<212> TYPE: PRT
<213> ORGANISM: Mus musculus

<400> SEQUENCE: 253

Leu Ile Leu Lys Val Gln Cys
1               5

<210> SEQ ID NO 254
<211> LENGTH: 7
<212> TYPE: PRT
<213> ORGANISM: Mus musculus

<400> SEQUENCE: 254

Leu Val Leu Lys Val Gln Cys
1               5

<210> SEQ ID NO 255
<211> LENGTH: 18
<212> TYPE: PRT
<213> ORGANISM: Mus musculus

<400> SEQUENCE: 255

Met Ala Val Val Thr Gly Lys Gly Leu Pro Ser Pro Lys Leu Glu Val
1               5                   10                  15

Asn Ser

<210> SEQ ID NO 256
<211> LENGTH: 17
<212> TYPE: PRT
<213> ORGANISM: Mus musculus

<400> SEQUENCE: 256

Met Asp Phe Gly Leu Ile Phe Phe Ile Val Ala Leu Leu Lys Val Gln
1               5                   10                  15

Cys

<210> SEQ ID NO 257
<211> LENGTH: 18
<212> TYPE: PRT
<213> ORGANISM: Mus musculus

<400> SEQUENCE: 257

Met Asp Phe Gly Leu Ser Leu Val Phe Leu Val Leu Ile Leu Lys Val
1               5                   10                  15

Gln Cys

<210> SEQ ID NO 258
<211> LENGTH: 21
<212> TYPE: PRT
<213> ORGANISM: Mus musculus

<400> SEQUENCE: 258

Met Asp Met Arg Ala Ser Ala Gln Phe His Gly Ile Leu Leu Leu Trp
1               5                   10                  15

Phe Pro Ala Arg Cys
            20

<210> SEQ ID NO 259
<211> LENGTH: 19
<212> TYPE: PRT
<213> ORGANISM: Mus musculus

<400> SEQUENCE: 259

```
Met Glu Trp Glu Leu Ser Leu Ile Phe Ile Phe Ala Leu Leu Lys Asp
1               5                   10                  15

Val Gln Cys


<210> SEQ ID NO 260
<211> LENGTH: 18
<212> TYPE: PRT
<213> ORGANISM: Mus musculus

<400> SEQUENCE: 260

Met Glu Trp Ser Cys Ile Phe Leu Phe Leu Leu Ser Val Thr Ala Val
1               5                   10                  15

His Ser


<210> SEQ ID NO 261
<211> LENGTH: 18
<212> TYPE: PRT
<213> ORGANISM: Mus musculus

<400> SEQUENCE: 261

Met Glu Trp Ser Cys Ile Phe Leu Phe Leu Leu Ser Val Thr Ala Ile
1               5                   10                  15

His Ser


<210> SEQ ID NO 262
<211> LENGTH: 18
<212> TYPE: PRT
<213> ORGANISM: Mus musculus

<400> SEQUENCE: 262

Met Glu Trp Ser Trp Ile Phe Leu Phe Leu Leu Ser Gly Thr Ala Val
1               5                   10                  15

Leu Ser


<210> SEQ ID NO 263
<211> LENGTH: 18
<212> TYPE: PRT
<213> ORGANISM: Mus musculus

<400> SEQUENCE: 263

Met Gly Trp Asn Trp Ile Phe Ile Leu Ile Leu Ser Val Thr Thr Ala
1               5                   10                  15

Leu Ser


<210> SEQ ID NO 264
<211> LENGTH: 18
<212> TYPE: PRT
<213> ORGANISM: Mus musculus

<400> SEQUENCE: 264

Met Gly Trp Ser Cys Ile Ile Leu Phe Leu Val Ala Thr Ala Thr Val
1               5                   10                  15

His Ser


<210> SEQ ID NO 265
<211> LENGTH: 18
<212> TYPE: PRT
<213> ORGANISM: Mus musculus

<400> SEQUENCE: 265
```

-continued

```
Met Gly Trp Asn Trp Ile Phe Ile Leu Ile Leu Ser Val Thr Thr Val
1               5                   10                  15

His Ser


<210> SEQ ID NO 266
<211> LENGTH: 18
<212> TYPE: PRT
<213> ORGANISM: Mus musculus

<400> SEQUENCE: 266

Met Gly Trp Ser Cys Ile Met Leu Phe Leu Ala Ala Thr Ala Thr Val
1               5                   10                  15

His Ser


<210> SEQ ID NO 267
<211> LENGTH: 18
<212> TYPE: PRT
<213> ORGANISM: Mus musculus

<400> SEQUENCE: 267

Met Gly Trp Ser Trp Ile Phe Phe Phe Leu Leu Ser Gly Thr Ala Val
1               5                   10                  15

Leu Ser


<210> SEQ ID NO 268
<211> LENGTH: 18
<212> TYPE: PRT
<213> ORGANISM: Mus musculus

<400> SEQUENCE: 268

Met Gly Trp Ser Trp Ile Phe Leu Phe Phe Leu Ser Gly Thr Ala Val
1               5                   10                  15

Leu Ser


<210> SEQ ID NO 269
<211> LENGTH: 18
<212> TYPE: PRT
<213> ORGANISM: Mus musculus

<400> SEQUENCE: 269

Met Gly Trp Ser Trp Ile Phe Leu Phe Leu Leu Ser Gly Ser Ala Val
1               5                   10                  15

Leu Ser


<210> SEQ ID NO 270
<211> LENGTH: 18
<212> TYPE: PRT
<213> ORGANISM: Mus musculus

<400> SEQUENCE: 270

Met Gly Trp Ser Trp Ile Phe Leu Phe Leu Leu Ser Gly Ser Ala Val
1               5                   10                  15

His Ser


<210> SEQ ID NO 271
<211> LENGTH: 18
<212> TYPE: PRT
<213> ORGANISM: Mus musculus

<400> SEQUENCE: 271

Met Gly Trp Ser Trp Ile Phe Leu Phe Leu Leu Ser Gly Thr Ala Val
```

-continued

```
1               5                   10                  15

His Ser


<210> SEQ ID NO 272
<211> LENGTH: 15
<212> TYPE: PRT
<213> ORGANISM: Mus musculus

<400> SEQUENCE: 272

Met Gly Trp Ser Tyr Ile Ile Leu Phe Leu Val Ala Thr Ala Thr
1               5                   10                  15


<210> SEQ ID NO 273
<211> LENGTH: 19
<212> TYPE: PRT
<213> ORGANISM: Mus musculus

<400> SEQUENCE: 273

Ile Asp Ile Asn Val Gln Ile Phe Arg Phe Leu Leu Ile Ser Val Thr
1               5                   10                  15

Ser Ser Gly


<210> SEQ ID NO 274
<211> LENGTH: 16
<212> TYPE: PRT
<213> ORGANISM: Mus musculus

<400> SEQUENCE: 274

Met Asn Met Leu Thr Gln Leu Leu Gly Leu Leu Leu Leu Trp Phe Ala
1               5                   10                  15


<210> SEQ ID NO 275
<211> LENGTH: 16
<212> TYPE: PRT
<213> ORGANISM: Mus musculus

<400> SEQUENCE: 275

Met Arg Thr Pro Ala His Phe Leu Gly Leu Leu Leu Leu Cys Phe Leu
1               5                   10                  15


<210> SEQ ID NO 276
<211> LENGTH: 18
<212> TYPE: PRT
<213> ORGANISM: Mus musculus

<400> SEQUENCE: 276

Met Arg Trp Ser Cys Ile Ile Leu Phe Leu Val Ala Thr Ala Thr Val
1               5                   10                  15

His Ser


<210> SEQ ID NO 277
<211> LENGTH: 16
<212> TYPE: PRT
<213> ORGANISM: Mus musculus

<400> SEQUENCE: 277

Met Asn Phe His Val Gln Ile Phe Ser Phe Met Leu Ile Ser Val Thr
1               5                   10                  15


<210> SEQ ID NO 278
<211> LENGTH: 15
<212> TYPE: PRT
<213> ORGANISM: Mus musculus
```

<400> SEQUENCE: 278

Met Glu Trp Ser Cys Ile Phe Leu Phe Leu Leu Ser Val Thr Ala
1               5                   10                  15

<210> SEQ ID NO 279
<211> LENGTH: 16
<212> TYPE: PRT
<213> ORGANISM: Mus musculus

<400> SEQUENCE: 279

Met Asp Phe Gln Val Gln Ile Phe Gln Ile Pro Val Lys Gln Cys Leu
1               5                   10                  15

<210> SEQ ID NO 280
<211> LENGTH: 16
<212> TYPE: PRT
<213> ORGANISM: Mus musculus

<400> SEQUENCE: 280

Met Asp Phe Gln Val Gln Ile Phe Ser Phe Leu Leu Ile Ser Ala Ser
1               5                   10                  15

<210> SEQ ID NO 281
<211> LENGTH: 16
<212> TYPE: PRT
<213> ORGANISM: Mus musculus

<400> SEQUENCE: 281

Met Lys Phe Pro Ser Gln Leu Leu Leu Phe Leu Leu Phe Arg Ile Thr
1               5                   10                  15

<210> SEQ ID NO 282
<211> LENGTH: 18
<212> TYPE: PRT
<213> ORGANISM: Mus musculus

<400> SEQUENCE: 282

Met Asp Met Arg Thr Pro Ala Gln Phe Leu Gly Ile Leu Leu Leu Trp
1               5                   10                  15

Phe Pro

<210> SEQ ID NO 283
<211> LENGTH: 15
<212> TYPE: PRT
<213> ORGANISM: Mus musculus

<400> SEQUENCE: 283

Met Ala Val Leu Ala Leu Leu Phe Cys Leu Val Thr Phe Pro Ser
1               5                   10                  15

<210> SEQ ID NO 284
<211> LENGTH: 16
<212> TYPE: PRT
<213> ORGANISM: Mus musculus

<400> SEQUENCE: 284

Met Asp Phe His Val Gln Ile Phe Ser Phe Met Leu Ile Ser Val Thr
1               5                   10                  15

<210> SEQ ID NO 285
<211> LENGTH: 16
<212> TYPE: PRT
<213> ORGANISM: Mus musculus

<400> SEQUENCE: 285

```
Met Asp Phe Gln Val Gln Ile Phe Ser Phe Leu Leu Ile Ser Ala Ser
1               5                   10                  15
```

<210> SEQ ID NO 286
<211> LENGTH: 15
<212> TYPE: PRT
<213> ORGANISM: Mus musculus

<400> SEQUENCE: 286

```
Met Asp Phe Gln Val Gln Ile Phe Ser Phe Leu Leu Ile Ser Arg
1               5                   10                  15
```

<210> SEQ ID NO 287
<211> LENGTH: 16
<212> TYPE: PRT
<213> ORGANISM: Mus musculus

<400> SEQUENCE: 287

```
Met Asp Phe Gln Val Gln Ile Phe Ser Phe Leu Leu Ile Ser Val Thr
1               5                   10                  15
```

<210> SEQ ID NO 288
<211> LENGTH: 15
<212> TYPE: PRT
<213> ORGANISM: Mus musculus

<400> SEQUENCE: 288

```
Thr Glu Leu Ile Cys Val Phe Leu Phe Leu Leu Ser Val Thr Ala
1               5                   10                  15
```

<210> SEQ ID NO 289
<211> LENGTH: 6
<212> TYPE: PRT
<213> ORGANISM: Mus musculus

<400> SEQUENCE: 289

```
Leu Leu Ile Ser Val Thr
1               5
```

<210> SEQ ID NO 290
<211> LENGTH: 16
<212> TYPE: PRT
<213> ORGANISM: Mus musculus

<400> SEQUENCE: 290

```
Met Asp Phe Gln Val Gln Ile Phe Ser Phe Leu Leu Ile Ser Ala Ser
1               5                   10                  15
```

<210> SEQ ID NO 291
<211> LENGTH: 16
<212> TYPE: PRT
<213> ORGANISM: Mus musculus

<400> SEQUENCE: 291

```
Met Asp Phe Gln Val Gln Ile Phe Ser Phe Leu Leu Ile Ser Val Ser
1               5                   10                  15
```

<210> SEQ ID NO 292
<211> LENGTH: 16
<212> TYPE: PRT
<213> ORGANISM: Mus musculus

<400> SEQUENCE: 292

Met Asp Phe Gln Val Gln Ile Phe Ser Phe Leu Leu Ile Ser Val Ser
1 5 10 15

<210> SEQ ID NO 293
<211> LENGTH: 16
<212> TYPE: PRT
<213> ORGANISM: Mus musculus

<400> SEQUENCE: 293

Met Asp Phe Gln Val Gln Ile Phe Ser Phe Leu Leu Met Ser Ala Ser
1 5 10 15

<210> SEQ ID NO 294
<211> LENGTH: 16
<212> TYPE: PRT
<213> ORGANISM: Mus musculus

<400> SEQUENCE: 294

Met Asp Leu Gln Val Gln Ile Ile Ser Phe Leu Leu Ile Ile Val Thr
1 5 10 15

<210> SEQ ID NO 295
<211> LENGTH: 16
<212> TYPE: PRT
<213> ORGANISM: Mus musculus

<400> SEQUENCE: 295

Met His Phe Gln Val Gln Ile Phe Ser Phe Leu Leu Ile Ser Ala Ser
1 5 10 15

<210> SEQ ID NO 296
<211> LENGTH: 15
<212> TYPE: PRT
<213> ORGANISM: Mus musculus

<400> SEQUENCE: 296

Met Lys Cys Ser Trp Val Ile Phe Phe Leu Met Ala Val Val Ile
1 5 10 15

<210> SEQ ID NO 297
<211> LENGTH: 15
<212> TYPE: PRT
<213> ORGANISM: Mus musculus

<400> SEQUENCE: 297

Met Lys Leu Trp Leu Asn Trp Ile Leu Leu Val Ala Leu Leu Asn
1 5 10 15

<210> SEQ ID NO 298
<211> LENGTH: 18
<212> TYPE: PRT
<213> ORGANISM: Mus musculus

<400> SEQUENCE: 298

Met Asp Met Arg Ala Pro Ala Gln Phe Phe Gly Ile Leu Leu Leu Trp
1 5 10 15

Phe Pro

<210> SEQ ID NO 299
<211> LENGTH: 16
<212> TYPE: PRT
<213> ORGANISM: Mus musculus

<400> SEQUENCE: 299

Met Ile Tyr Ser Leu Gln Leu Leu Arg Met Leu Val Leu Trp Ile Pro
1 5 10 15

<210> SEQ ID NO 300
<211> LENGTH: 16
<212> TYPE: PRT
<213> ORGANISM: Mus musculus

<400> SEQUENCE: 300

Met Met Ser Pro Val His Ser Ile Phe Ile Leu Leu Leu Trp Ile Val
1 5 10 15

<210> SEQ ID NO 301
<211> LENGTH: 16
<212> TYPE: PRT
<213> ORGANISM: Mus musculus

<400> SEQUENCE: 301

Met Ser Tyr Ser Leu Gln Leu Leu Arg Met Leu Val Leu Trp Ile Pro
1 5 10 15

<210> SEQ ID NO 302
<211> LENGTH: 16
<212> TYPE: PRT
<213> ORGANISM: Mus musculus

<400> SEQUENCE: 302

Met Ser Tyr Ser Leu Gln Leu Leu Arg Met Leu Val Leu Trp Ile Pro
1 5 10 15

<210> SEQ ID NO 303
<211> LENGTH: 16
<212> TYPE: PRT
<213> ORGANISM: Mus musculus

<400> SEQUENCE: 303

Met Asp Phe Gln Met Gln Ile Ile Ser Leu Leu Leu Ile Ser Val Thr
1 5 10 15

<210> SEQ ID NO 304
<211> LENGTH: 21
<212> TYPE: PRT
<213> ORGANISM: Mus musculus

<400> SEQUENCE: 304

Met Asp Phe Gln Val Gln Ile Phe Gln Ile Pro Val Lys Gln Cys Leu
1 5 10 15

Ile Ile Ser Arg Gly
20

<210> SEQ ID NO 305
<211> LENGTH: 16
<212> TYPE: PRT
<213> ORGANISM: Mus musculus

<400> SEQUENCE: 305

Met Asp Phe Gln Val Gln Ile Phe Ser Phe Leu Leu Ile Ser Ala Ser
1 5 10 15

<210> SEQ ID NO 306
<211> LENGTH: 16
<212> TYPE: PRT
<213> ORGANISM: Mus musculus

<400> SEQUENCE: 306

Met Arg Pro Thr Leu Ser Phe Leu Gly Ser Cys Cys Ser Ser Leu Ile
1 5 10 15

<210> SEQ ID NO 307
<211> LENGTH: 16
<212> TYPE: PRT
<213> ORGANISM: Mus musculus

<400> SEQUENCE: 307

Met Lys Phe Pro Ser Gln Leu Leu Leu Leu Leu Leu Phe Gly Ile Pro
1 5 10 15

<210> SEQ ID NO 308
<211> LENGTH: 19
<212> TYPE: PRT
<213> ORGANISM: Mus musculus

<400> SEQUENCE: 308

Met Glu Ser Asp Thr Leu Leu Leu Trp Val Leu Leu Leu Trp Val Pro
1 5 10 15

Ser Thr Ser

<210> SEQ ID NO 309
<211> LENGTH: 19
<212> TYPE: PRT
<213> ORGANISM: Mus musculus

<400> SEQUENCE: 309

Met Glu Ser Gln Thr Leu Val Phe Ile Ser Ile Leu Leu Trp Leu Tyr
1 5 10 15

Ala Asp Gly

<210> SEQ ID NO 310
<211> LENGTH: 19
<212> TYPE: PRT
<213> ORGANISM: Mus musculus

<400> SEQUENCE: 310

Met Glu Ser Gln Thr Gln Val Phe Leu Ser Leu Leu Leu Trp Val Ser
1 5 10 15

Thr Cys Gly

<210> SEQ ID NO 311
<211> LENGTH: 19
<212> TYPE: PRT
<213> ORGANISM: Mus musculus

<400> SEQUENCE: 311

Met Glu Thr Asp Thr Leu Leu Leu Trp Val Leu Leu Leu Trp Val Pro
1 5 10 15

Ser Thr Gly

<210> SEQ ID NO 312
<211> LENGTH: 18
<212> TYPE: PRT
<213> ORGANISM: Mus musculus

<400> SEQUENCE: 312

Met Gly Trp Ser Cys Ile Met Leu Phe Leu Ala Ala Thr Ala Thr Val
1 5 10 15

His Ser

<210> SEQ ID NO 313
<211> LENGTH: 19
<212> TYPE: PRT
<213> ORGANISM: Mus musculus

<400> SEQUENCE: 313

```
Met Gly Trp Ser Cys Ile Met Leu Phe Leu Ala Ala Thr Ala Thr Gly
1               5                   10                  15

Val His Ser
```

<210> SEQ ID NO 314
<211> LENGTH: 18
<212> TYPE: PRT
<213> ORGANISM: Mus musculus

<400> SEQUENCE: 314

```
Met Ala Trp Ile Ser Leu Ile Leu Ser Leu Leu Ala Leu Ser Ser Ala
1               5                   10                  15

Ile Ser
```

<210> SEQ ID NO 315
<211> LENGTH: 18
<212> TYPE: PRT
<213> ORGANISM: Mus musculus

<400> SEQUENCE: 315

```
Ile Gly Trp Ser Tyr Ile Ile Leu Leu Leu Val Ala Thr Ala Thr Val
1               5                   10                  15

His Ser
```

<210> SEQ ID NO 316
<211> LENGTH: 18
<212> TYPE: PRT
<213> ORGANISM: Mus musculus

<400> SEQUENCE: 316

```
Met Ala Trp Thr Ser Leu Ile Leu Ser Leu Leu Ala Leu Cys Ser Ala
1               5                   10                  15

Ser Ser
```

<210> SEQ ID NO 317
<211> LENGTH: 18
<212> TYPE: PRT
<213> ORGANISM: Mus musculus

<400> SEQUENCE: 317

```
Met Ala Trp Thr Ser Leu Ile Leu Ser Leu Leu Ala Leu Cys Ser Ala
1               5                   10                  15

Ile Ser
```

<210> SEQ ID NO 318
<211> LENGTH: 18
<212> TYPE: PRT
<213> ORGANISM: Mus musculus

<400> SEQUENCE: 318

```
Met Gly Trp Ser Cys Val Leu Leu Phe Leu Val Ser Gly Thr Ala Val
1               5                   10                  15

Leu Cys
```

<210> SEQ ID NO 319
<211> LENGTH: 21
<212> TYPE: PRT
<213> ORGANISM: Mus musculus

<400> SEQUENCE: 319

```
Met Asp Phe Gln Val Gln Ile Phe Ser Phe Leu Leu Ile Ser Ala Ser
1               5                   10                  15

Ile Ile Ser Arg Gly
            20
```

<210> SEQ ID NO 320
<211> LENGTH: 21
<212> TYPE: PRT
<213> ORGANISM: Mus musculus

<400> SEQUENCE: 320

```
Met Asp Phe Gln Val Gln Ile Phe Ser Phe Leu Leu Ile Ser Ala Ser
1               5                   10                  15

Ile Leu Phe Arg Gly
            20
```

<210> SEQ ID NO 321
<211> LENGTH: 21
<212> TYPE: PRT
<213> ORGANISM: Mus musculus

<400> SEQUENCE: 321

```
Met Asp Phe Gln Val Gln Ile Phe Ser Phe Leu Leu Ile Ser Ala Ser
1               5                   10                  15

Ile Leu Ser Arg Gly
            20
```

<210> SEQ ID NO 322
<211> LENGTH: 21
<212> TYPE: PRT
<213> ORGANISM: Mus musculus

<400> SEQUENCE: 322

```
Met Asp Phe Gln Val Gln Ile Phe Ser Phe Leu Leu Ile Ser Ala Ser
1               5                   10                  15

Ile Met Ser Arg Gly
            20
```

<210> SEQ ID NO 323
<211> LENGTH: 21
<212> TYPE: PRT
<213> ORGANISM: Mus musculus

<400> SEQUENCE: 323

```
Met Asp Phe Gln Val Gln Ile Phe Ser Phe Leu Leu Ile Ser Ala Ser
1               5                   10                  15

Leu Met Ser Arg Gly
            20
```

<210> SEQ ID NO 324
<211> LENGTH: 20
<212> TYPE: PRT
<213> ORGANISM: Mus musculus

<400> SEQUENCE: 324

```
Met Asp Phe Gln Val Gln Ile Phe Ser Phe Leu Leu Ile Ser Arg Ile
1               5                   10                  15

Leu Ser Arg Gly
            20


<210> SEQ ID NO 325
<211> LENGTH: 21
<212> TYPE: PRT
<213> ORGANISM: Mus musculus

<400> SEQUENCE: 325

Met Asp Phe Gln Val Gln Ile Phe Ser Phe Leu Leu Ile Ser Val Ser
1               5                   10                  15

Ile Met Ser Arg Gly
            20


<210> SEQ ID NO 326
<211> LENGTH: 21
<212> TYPE: PRT
<213> ORGANISM: Mus musculus

<400> SEQUENCE: 326

Met Asp Phe Gln Val Gln Ile Phe Ser Phe Leu Leu Met Ser Ala Ser
1               5                   10                  15

Ile Met Ser Arg Gly
            20


<210> SEQ ID NO 327
<211> LENGTH: 19
<212> TYPE: PRT
<213> ORGANISM: Mus musculus

<400> SEQUENCE: 327

Met Asp Thr Leu Cys Ser Thr Leu Leu Leu Leu Thr Ile Pro Ser Trp
1               5                   10                  15

Val Leu Ser


<210> SEQ ID NO 328
<211> LENGTH: 18
<212> TYPE: PRT
<213> ORGANISM: Mus musculus

<400> SEQUENCE: 328

Met Gly Trp Ser Trp Ile Phe Leu Phe Leu Leu Ser Gly Thr Ala Val
1               5                   10                  15

His Cys


<210> SEQ ID NO 329
<211> LENGTH: 21
<212> TYPE: PRT
<213> ORGANISM: Mus musculus

<400> SEQUENCE: 329

Met His Phe Gln Val Gln Ile Phe Ser Phe Leu Leu Ile Ser Ala Ser
1               5                   10                  15

Ile Met Ser Arg Gly
            20


<210> SEQ ID NO 330
<211> LENGTH: 18
<212> TYPE: PRT
<213> ORGANISM: Mus musculus
```

<400> SEQUENCE: 330

Met Ala Trp Thr Pro Leu Phe Phe Phe Phe Val Leu His Cys Ser Ser
1 5 10 15

Phe Ser

<210> SEQ ID NO 331
<211> LENGTH: 18
<212> TYPE: PRT
<213> ORGANISM: Mus musculus

<400> SEQUENCE: 331

Met Arg Val Leu Gly Phe Leu Cys Leu Val Thr Val Leu Pro Gly Ser
1 5 10 15

Leu Ser

<210> SEQ ID NO 332
<211> LENGTH: 18
<212> TYPE: PRT
<213> ORGANISM: Mus musculus

<400> SEQUENCE: 332

Met Ala Trp Thr Pro Leu Phe Phe Phe Phe Leu Leu His Cys Ser Ser
1 5 10 15

Phe Ser

<210> SEQ ID NO 333
<211> LENGTH: 13
<212> TYPE: PRT
<213> ORGANISM: Mus musculus

<400> SEQUENCE: 333

Ile Phe Leu Phe Leu Leu Ser Ile Thr Ala Val His Cys
1 5 10

<210> SEQ ID NO 334
<211> LENGTH: 18
<212> TYPE: PRT
<213> ORGANISM: Mus musculus

<400> SEQUENCE: 334

Lys Gly Gly Ser Cys Val Ser Leu Phe Leu Val Ala Thr Ala Asn Val
1 5 10 15

His Phe

<210> SEQ ID NO 335
<211> LENGTH: 18
<212> TYPE: PRT
<213> ORGANISM: Mus musculus

<400> SEQUENCE: 335

Met Ala Val Leu Ala Leu Leu Phe Cys Leu Val Thr Phe Pro Ser Ile
1 5 10 15

Leu Ser

<210> SEQ ID NO 336
<211> LENGTH: 18
<212> TYPE: PRT
<213> ORGANISM: Mus musculus

<400> SEQUENCE: 336

```
Met Ala Val Leu Gly Leu Leu Phe Cys Leu Val Thr Phe Pro Ser Val
1               5                   10                  15

Leu Ser


<210> SEQ ID NO 337
<211> LENGTH: 18
<212> TYPE: PRT
<213> ORGANISM: Mus musculus

<400> SEQUENCE: 337

Met Ala Val Leu Gly Leu Leu Leu Cys Leu Val Thr Phe Pro Ser Val
1               5                   10                  15

Leu Ser


<210> SEQ ID NO 338
<211> LENGTH: 18
<212> TYPE: PRT
<213> ORGANISM: Mus musculus

<400> SEQUENCE: 338

Met Ala Trp Ser Trp Val Phe Leu Phe Phe Leu Ser Val Thr Thr Val
1               5                   10                  15

His Ser


<210> SEQ ID NO 339
<211> LENGTH: 18
<212> TYPE: PRT
<213> ORGANISM: Mus musculus

<400> SEQUENCE: 339

Met Asp Trp Ile Trp Ile Met Leu His Leu Leu Ala Ala Thr Gly Ile
1               5                   10                  15

Gln Ser


<210> SEQ ID NO 340
<211> LENGTH: 18
<212> TYPE: PRT
<213> ORGANISM: Mus musculus

<400> SEQUENCE: 340

Met Glu Cys Ser Trp Val Phe Leu Phe Leu Leu Ser Leu Thr Ala Val
1               5                   10                  15

His Cys


<210> SEQ ID NO 341
<211> LENGTH: 19
<212> TYPE: PRT
<213> ORGANISM: Mus musculus

<400> SEQUENCE: 341

Met Glu Phe Gly Leu Ser Trp Val Phe Leu Val Ala Leu Leu Arg Gly
1               5                   10                  15

Val Gln Cys


<210> SEQ ID NO 342
<211> LENGTH: 18
<212> TYPE: PRT
<213> ORGANISM: Mus musculus
<220> FEATURE:
<221> NAME/KEY: misc_feature
<222> LOCATION: (5)..(6)
<223> OTHER INFORMATION: Xaa can be any naturally occurring amino acid
```

<400> SEQUENCE: 342

Met Glu Trp Leu Xaa Xaa Phe Leu Leu Phe Leu Ser Leu Thr Ala Val
1 5 10 15

His Cys

<210> SEQ ID NO 343
<211> LENGTH: 18
<212> TYPE: PRT
<213> ORGANISM: Mus musculus

<400> SEQUENCE: 343

Met Glu Trp Ser Gly Val Phe Ile Phe Leu Leu Ser Val Thr Ala Val
1 5 10 15

His Ser

<210> SEQ ID NO 344
<211> LENGTH: 16
<212> TYPE: PRT
<213> ORGANISM: Mus musculus

<400> SEQUENCE: 344

Met Glu Thr Pro Ala Ser Phe Leu Cys Leu Leu Leu Leu Trp Thr Thr
1 5 10 15

<210> SEQ ID NO 345
<211> LENGTH: 15
<212> TYPE: PRT
<213> ORGANISM: Mus musculus

<400> SEQUENCE: 345

Met Ala Trp Thr Pro Leu Phe Phe Phe Phe Leu Leu His Cys Ser
1 5 10 15

<210> SEQ ID NO 346
<211> LENGTH: 15
<212> TYPE: PRT
<213> ORGANISM: Mus musculus

<400> SEQUENCE: 346

Met Ala Trp Thr Pro Leu Phe Phe Phe Phe Val Leu His Cys Ser
1 5 10 15

<210> SEQ ID NO 347
<211> LENGTH: 19
<212> TYPE: PRT
<213> ORGANISM: Mus musculus

<400> SEQUENCE: 347

Met Lys Ser Gln Thr Gln Val Phe Ile Phe Leu Leu Leu Cys Val Ser
1 5 10 15

Ala His Gly

<210> SEQ ID NO 348
<211> LENGTH: 19
<212> TYPE: PRT
<213> ORGANISM: Mus musculus

<400> SEQUENCE: 348

Met Lys Ser Gln Thr Gln Val Phe Val Phe Leu Leu Leu Cys Val Ser
1 5 10 15

Ala His Gly

<210> SEQ ID NO 349
<211> LENGTH: 16
<212> TYPE: PRT
<213> ORGANISM: Mus musculus

<400> SEQUENCE: 349

Met Asp Met Trp Val Gln Ile Phe Ser Leu Leu Leu Ile Cys Val Thr
1 5 10 15

<210> SEQ ID NO 350
<211> LENGTH: 19
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 350

Met Xaa Thr Met Asp Glu His Glu Ser Gly Ala Val Thr Pro His Gln
1 5 10 15

Val Leu Lys

<210> SEQ ID NO 351
<211> LENGTH: 16
<212> TYPE: PRT
<213> ORGANISM: Mus musculus

<400> SEQUENCE: 351

Met Gly Glu Gln Arg Ile Arg Ser Cys His Ala Thr Ser Gly Ala Glu
1 5 10 15

<210> SEQ ID NO 352
<211> LENGTH: 16
<212> TYPE: PRT
<213> ORGANISM: Mus musculus

<400> SEQUENCE: 352

Met Asn Leu Pro Val His Leu Leu Val Leu Leu Leu Phe Trp Ile Pro
1 5 10 15

<210> SEQ ID NO 353
<211> LENGTH: 18
<212> TYPE: PRT
<213> ORGANISM: Mus musculus

<400> SEQUENCE: 353

Met Thr Met Phe Ser Leu Ala Leu Leu Leu Ser Leu Leu Leu Leu Cys
1 5 10 15

Val Ser

<210> SEQ ID NO 354
<211> LENGTH: 15
<212> TYPE: PRT
<213> ORGANISM: Mus musculus

<400> SEQUENCE: 354

Met Thr Met Leu Ser Leu Ala Pro Leu Leu Ser Leu Leu Leu Leu
1 5 10 15

<210> SEQ ID NO 355
<211> LENGTH: 16
<212> TYPE: PRT

<213> ORGANISM: Mus musculus

<400> SEQUENCE: 355

Met Thr Met Leu Ser Leu Val Leu Leu Leu Ser Phe Leu Leu Leu Cys
1 5 10 15

<210> SEQ ID NO 356
<211> LENGTH: 16
<212> TYPE: PRT
<213> ORGANISM: Mus musculus

<400> SEQUENCE: 356

Met Val Phe Thr Pro Gln Ile Leu Gly Leu Met Leu Phe Trp Ile Ser
1 5 10 15

<210> SEQ ID NO 357
<211> LENGTH: 15
<212> TYPE: PRT
<213> ORGANISM: Mus musculus

<400> SEQUENCE: 357

Met Val Leu Gly Leu Lys Trp Val Phe Phe Val Val Phe Tyr Gln
1 5 10 15

<210> SEQ ID NO 358
<211> LENGTH: 16
<212> TYPE: PRT
<213> ORGANISM: Mus musculus

<400> SEQUENCE: 358

Met Val Ser Thr Ser Gln Leu Leu Gly Leu Leu Leu Phe Trp Thr Ser
1 5 10 15

<210> SEQ ID NO 359
<211> LENGTH: 13
<212> TYPE: PRT
<213> ORGANISM: Mus musculus

<400> SEQUENCE: 359

Pro Ala Gln Phe Leu Phe Leu Leu Val Leu Trp Ile Gln
1 5 10

<210> SEQ ID NO 360
<211> LENGTH: 16
<212> TYPE: PRT
<213> ORGANISM: Mus musculus

<400> SEQUENCE: 360

Ile Asp Ile Asn Val Gln Ile Phe Arg Phe Leu Leu Ile Ser Val Thr
1 5 10 15

<210> SEQ ID NO 361
<211> LENGTH: 16
<212> TYPE: PRT
<213> ORGANISM: Mus musculus

<400> SEQUENCE: 361

Met Lys Leu Pro Val Leu Leu Val Val Leu Leu Leu Phe Thr Ser Pro
1 5 10 15

<210> SEQ ID NO 362
<211> LENGTH: 15
<212> TYPE: PRT
<213> ORGANISM: Mus musculus

<400> SEQUENCE: 362

Met Lys Leu Pro Val Arg Leu Leu Val Leu Met Phe Trp Ile Pro
1 5 10 15

<210> SEQ ID NO 363
<211> LENGTH: 15
<212> TYPE: PRT
<213> ORGANISM: Mus musculus

<400> SEQUENCE: 363

Met Lys Leu Pro Val Arg Leu Leu Val Leu Met Phe Trp Ile Pro
1 5 10 15

<210> SEQ ID NO 364
<211> LENGTH: 16
<212> TYPE: PRT
<213> ORGANISM: Mus musculus

<400> SEQUENCE: 364

Met Glu Lys Asp Thr Leu Leu Leu Trp Val Leu Leu Leu Trp Val Pro
1 5 10 15

<210> SEQ ID NO 365
<211> LENGTH: 16
<212> TYPE: PRT
<213> ORGANISM: Mus musculus

<400> SEQUENCE: 365

Met Glu Ser Asp Thr Leu Leu Leu Trp Val Leu Leu Leu Trp Val Pro
1 5 10 15

<210> SEQ ID NO 366
<211> LENGTH: 16
<212> TYPE: PRT
<213> ORGANISM: Mus musculus

<400> SEQUENCE: 366

Met Glu Ser Asp Thr Leu Leu Leu Trp Val Leu Leu Leu Trp Val Pro
1 5 10 15

<210> SEQ ID NO 367
<211> LENGTH: 16
<212> TYPE: PRT
<213> ORGANISM: Mus musculus

<400> SEQUENCE: 367

Met Glu Thr Asp Pro Leu Leu Leu Trp Val Leu Leu Leu Trp Val Pro
1 5 10 15

<210> SEQ ID NO 368
<211> LENGTH: 16
<212> TYPE: PRT
<213> ORGANISM: Mus musculus

<400> SEQUENCE: 368

Met Glu Thr Asp Thr Ile Leu Leu Trp Val Leu Leu Leu Trp Val Pro
1 5 10 15

<210> SEQ ID NO 369
<211> LENGTH: 16
<212> TYPE: PRT
<213> ORGANISM: Mus musculus

<400> SEQUENCE: 369

-continued

Met Glu Thr Asp Thr Leu Leu Leu Trp Val Leu Leu Leu Trp Val Pro
1 5 10 15

<210> SEQ ID NO 370
<211> LENGTH: 16
<212> TYPE: PRT
<213> ORGANISM: Mus musculus

<400> SEQUENCE: 370

Met Glu Thr Asp Thr Leu Leu Leu Trp Val Leu Leu Leu Trp Val Pro
1 5 10 15

<210> SEQ ID NO 371
<211> LENGTH: 16
<212> TYPE: PRT
<213> ORGANISM: Mus musculus

<400> SEQUENCE: 371

Met Glu Thr Asp Thr Leu Leu Leu Trp Val Leu Leu Leu Trp Val Pro
1 5 10 15

<210> SEQ ID NO 372
<211> LENGTH: 16
<212> TYPE: PRT
<213> ORGANISM: Mus musculus

<400> SEQUENCE: 372

Met Arg Phe Ser Ala Gln Leu Leu Gly Leu Leu Val Leu Trp Ile Pro
1 5 10 15

<210> SEQ ID NO 373
<211> LENGTH: 16
<212> TYPE: PRT
<213> ORGANISM: Mus musculus

<400> SEQUENCE: 373

Met Val Phe Thr Pro Gln Ile Leu Gly Leu Met Leu Phe Trp Ile Ser
1 5 10 15

<210> SEQ ID NO 374
<211> LENGTH: 16
<212> TYPE: PRT
<213> ORGANISM: Mus musculus

<400> SEQUENCE: 374

Met Asp Ser Gln Ala Gln Val Leu Ile Leu Leu Leu Leu Trp Val Ser
1 5 10 15

<210> SEQ ID NO 375
<211> LENGTH: 16
<212> TYPE: PRT
<213> ORGANISM: Mus musculus

<400> SEQUENCE: 375

Met Asp Ser Gln Ala Gln Val Leu Met Leu Leu Leu Leu Ser Val Ser
1 5 10 15

<210> SEQ ID NO 376
<211> LENGTH: 16
<212> TYPE: PRT
<213> ORGANISM: Mus musculus

<400> SEQUENCE: 376

Met Asp Ser Gln Ala Gln Val Leu Met Leu Leu Leu Leu Trp Val Ser
1 5 10 15

<210> SEQ ID NO 377
<211> LENGTH: 16
<212> TYPE: PRT
<213> ORGANISM: Mus musculus

<400> SEQUENCE: 377

Met Asp Ser Gln Ala Arg Val Leu Met Leu Leu Leu Leu Trp Val Ser
1 5 10 15

<210> SEQ ID NO 378
<211> LENGTH: 16
<212> TYPE: PRT
<213> ORGANISM: Mus musculus

<400> SEQUENCE: 378

Met Glu Ser Gln Asn His Val Leu Met Phe Leu Leu Leu Trp Val Ser
1 5 10 15

<210> SEQ ID NO 379
<211> LENGTH: 16
<212> TYPE: PRT
<213> ORGANISM: Mus musculus

<400> SEQUENCE: 379

Met Glu Ser Gln Thr His Val Leu Met Phe Leu Leu Leu Trp Val Ser
1 5 10 15

<210> SEQ ID NO 380
<211> LENGTH: 16
<212> TYPE: PRT
<213> ORGANISM: Mus musculus

<400> SEQUENCE: 380

Met Glu Ser Gln Thr Gln Val Phe Leu Ser Leu Leu Leu Trp Val Ser
1 5 10 15

<210> SEQ ID NO 381
<211> LENGTH: 16
<212> TYPE: PRT
<213> ORGANISM: Mus musculus

<400> SEQUENCE: 381

Met Glu Ser Gln Thr Gln Val Leu Ile Ser Leu Leu Phe Trp Val Ser
1 5 10 15

<210> SEQ ID NO 382
<211> LENGTH: 16
<212> TYPE: PRT
<213> ORGANISM: Mus musculus

<400> SEQUENCE: 382

Met Glu Ser Gln Thr Gln Val Leu Met Ser Leu Leu Phe Trp Val Ser
1 5 10 15

<210> SEQ ID NO 383
<211> LENGTH: 19
<212> TYPE: PRT
<213> ORGANISM: Mus musculus

<400> SEQUENCE: 383

Met Glu Thr Pro Ala Ser Phe Leu Cys Leu Leu Leu Leu Trp Thr Thr
1 5 10 15

Ser Ala Val

<210> SEQ ID NO 384
<211> LENGTH: 16
<212> TYPE: PRT
<213> ORGANISM: Mus musculus

<400> SEQUENCE: 384

Gln His Gly His Glu Gly Leu Cys Ser Val Ser Trp Val Pro Val Ala
1 5 10 15

<210> SEQ ID NO 385
<211> LENGTH: 16
<212> TYPE: PRT
<213> ORGANISM: Mus musculus

<400> SEQUENCE: 385

Met Met Ser Pro Ala Gln Phe Leu Phe Leu Leu Val Leu Trp Ile Gln
1 5 10 15

<210> SEQ ID NO 386
<211> LENGTH: 16
<212> TYPE: PRT
<213> ORGANISM: Mus musculus

<400> SEQUENCE: 386

Met Met Ser Pro Ala Gln Phe Leu Phe Leu Leu Val Leu Trp Ile Arg
1 5 10 15

<210> SEQ ID NO 387
<211> LENGTH: 16
<212> TYPE: PRT
<213> ORGANISM: Mus musculus

<400> SEQUENCE: 387

Met Met Ser Pro Val Gln Phe Leu Phe Leu Leu Met Leu Trp Ile Gln
1 5 10 15

<210> SEQ ID NO 388
<211> LENGTH: 16
<212> TYPE: PRT
<213> ORGANISM: Mus musculus

<400> SEQUENCE: 388

Met Ile Ala Ser Ala Gln Phe Leu Gly Leu Leu Leu Leu Cys Phe Gln
1 5 10 15

<210> SEQ ID NO 389
<211> LENGTH: 16
<212> TYPE: PRT
<213> ORGANISM: Mus musculus

<400> SEQUENCE: 389

Met Met Ser Ser Ala Gln Phe Leu Gly Leu Leu Leu Leu Cys Phe Gln
1 5 10 15

<210> SEQ ID NO 390
<211> LENGTH: 16
<212> TYPE: PRT
<213> ORGANISM: Mus musculus

<400> SEQUENCE: 390

Met Met Ser Ser Ala Gln Phe Leu Gly Leu Leu Leu Leu Cys Phe Gln
1 5 10 15

-continued

<210> SEQ ID NO 391
<211> LENGTH: 18
<212> TYPE: PRT
<213> ORGANISM: Mus musculus

<400> SEQUENCE: 391

Met Asp Met Arg Ala Pro Ala Gln Ile Phe Gly Phe Leu Leu Leu Leu
1 5 10 15

Phe Gln

<210> SEQ ID NO 392
<211> LENGTH: 18
<212> TYPE: PRT
<213> ORGANISM: Mus musculus

<400> SEQUENCE: 392

Met Asp Met Arg Val Pro Ala His Val Phe Gly Phe Leu Leu Leu Trp
1 5 10 15

Phe Pro

<210> SEQ ID NO 393
<211> LENGTH: 15
<212> TYPE: PRT
<213> ORGANISM: Mus musculus

<400> SEQUENCE: 393

Met Asp Cys Gly Ile Ser Leu Val Phe Leu Val Leu Ile Leu Lys
1 5 10 15

<210> SEQ ID NO 394
<211> LENGTH: 16
<212> TYPE: PRT
<213> ORGANISM: Mus musculus

<400> SEQUENCE: 394

Met Glu Phe Gln Thr Gln Val Phe Val Phe Val Leu Leu Trp Leu Ser
1 5 10 15

<210> SEQ ID NO 395
<211> LENGTH: 16
<212> TYPE: PRT
<213> ORGANISM: Mus musculus

<400> SEQUENCE: 395

Met Glu Ser Gln Ile Gln Ala Phe Val Phe Val Phe Leu Trp Leu Ser
1 5 10 15

<210> SEQ ID NO 396
<211> LENGTH: 16
<212> TYPE: PRT
<213> ORGANISM: Mus musculus

<400> SEQUENCE: 396

Met Glu Ser Gln Ile Gln Val Phe Val Phe Val Phe Leu Trp Leu Ser
1 5 10 15

<210> SEQ ID NO 397
<211> LENGTH: 16
<212> TYPE: PRT
<213> ORGANISM: Mus musculus

<400> SEQUENCE: 397

Met Glu Ser Gln Thr Gln Val Phe Val Tyr Met Leu Leu Trp Leu Ser
1 5 10 15

<210> SEQ ID NO 398
<211> LENGTH: 20
<212> TYPE: PRT
<213> ORGANISM: Mus musculus

<400> SEQUENCE: 398

Met Gly Phe Lys Met Glu Ser His Thr Gln Ala Phe Val Phe Ala Phe
1 5 10 15

Leu Trp Leu Ser
20

<210> SEQ ID NO 399
<211> LENGTH: 16
<212> TYPE: PRT
<213> ORGANISM: Mus musculus

<400> SEQUENCE: 399

Met Glu Thr His Ser Gln Val Phe Val Tyr Met Leu Leu Trp Leu Ser
1 5 10 15

<210> SEQ ID NO 400
<211> LENGTH: 15
<212> TYPE: PRT
<213> ORGANISM: Mus musculus
<220> FEATURE:
<221> NAME/KEY: misc_feature
<222> LOCATION: (5)..(6)
<223> OTHER INFORMATION: Xaa can be any naturally occurring amino acid

<400> SEQUENCE: 400

Met Glu Trp Leu Xaa Xaa Phe Leu Leu Phe Leu Ser Leu Thr Ala
1 5 10 15

<210> SEQ ID NO 401
<211> LENGTH: 15
<212> TYPE: PRT
<213> ORGANISM: Mus musculus

<400> SEQUENCE: 401

Met Glu Trp Ser Cys Ile Phe Leu Phe Leu Leu Ser Val Thr Ala
1 5 10 15

<210> SEQ ID NO 402
<211> LENGTH: 15
<212> TYPE: PRT
<213> ORGANISM: Mus musculus

<400> SEQUENCE: 402

Met Glu Trp Ser Gly Val Phe Ile Phe Leu Leu Ser Val Thr Ala
1 5 10 15

<210> SEQ ID NO 403
<211> LENGTH: 15
<212> TYPE: PRT
<213> ORGANISM: Mus musculus

<400> SEQUENCE: 403

Met Glu Trp Ser Arg Val Phe Ile Phe Leu Leu Ser Val Thr Ala
1 5 10 15

<210> SEQ ID NO 404
<211> LENGTH: 15
<212> TYPE: PRT
<213> ORGANISM: Mus musculus

<400> SEQUENCE: 404

Met Glu Trp Ser Trp Val Phe Leu Phe Phe Leu Ser Val Thr Thr
1 5 10 15

<210> SEQ ID NO 405
<211> LENGTH: 15
<212> TYPE: PRT
<213> ORGANISM: Mus musculus

<400> SEQUENCE: 405

Met Glu Trp Ser Trp Val Phe Leu Phe Leu Leu Ser Leu Thr Ser
1 5 10 15

<210> SEQ ID NO 406
<211> LENGTH: 15
<212> TYPE: PRT
<213> ORGANISM: Mus musculus

<400> SEQUENCE: 406

Met Gly Trp Asn Trp Ile Phe Ile Leu Ile Leu Ser Val Thr Thr
1 5 10 15

<210> SEQ ID NO 407
<211> LENGTH: 15
<212> TYPE: PRT
<213> ORGANISM: Mus musculus

<400> SEQUENCE: 407

Met Gly Trp Ser Cys Ile Ile Phe Phe Leu Val Ala Thr Ala Thr
1 5 10 15

<210> SEQ ID NO 408
<211> LENGTH: 15
<212> TYPE: PRT
<213> ORGANISM: Mus musculus

<400> SEQUENCE: 408

Met Gly Trp Ser Cys Ile Ile Leu Phe Leu Val Ala Ala Ala Asn
1 5 10 15

<210> SEQ ID NO 409
<211> LENGTH: 15
<212> TYPE: PRT
<213> ORGANISM: Mus musculus

<400> SEQUENCE: 409

Met Gly Trp Ser Cys Ile Ile Leu Phe Leu Val Ala Ala Ala Thr
1 5 10 15

<210> SEQ ID NO 410
<211> LENGTH: 15
<212> TYPE: PRT
<213> ORGANISM: Mus musculus

<400> SEQUENCE: 410

Met Gly Trp Ser Cys Ile Ile Leu Phe Leu Val Ala Thr Ala Thr
1 5 10 15

<210> SEQ ID NO 411
<211> LENGTH: 15
<212> TYPE: PRT
<213> ORGANISM: Mus musculus

<400> SEQUENCE: 411

Met Gly Trp Ser Cys Ile Ile Leu Phe Leu Val Ala Thr Ala Thr
1 5 10 15

<210> SEQ ID NO 412
<211> LENGTH: 15
<212> TYPE: PRT
<213> ORGANISM: Mus musculus

<400> SEQUENCE: 412

Met Gly Trp Ser Cys Ile Ile Leu Phe Leu Val Ala Thr Ala Thr
1 5 10 15

<210> SEQ ID NO 413
<211> LENGTH: 15
<212> TYPE: PRT
<213> ORGANISM: Mus musculus

<400> SEQUENCE: 413

Met Gly Trp Ser Cys Ile Ile Leu Phe Leu Val Ser Thr Ala Thr
1 5 10 15

<210> SEQ ID NO 414
<211> LENGTH: 15
<212> TYPE: PRT
<213> ORGANISM: Mus musculus

<400> SEQUENCE: 414

Met Gly Trp Ser Cys Ile Ile Leu Ile Leu Val Ala Ala Ala Thr
1 5 10 15

<210> SEQ ID NO 415
<211> LENGTH: 15
<212> TYPE: PRT
<213> ORGANISM: Mus musculus

<400> SEQUENCE: 415

Met Gly Trp Ser Cys Ile Ile Leu Ile Leu Val Ala Ala Ala Thr
1 5 10 15

<210> SEQ ID NO 416
<211> LENGTH: 15
<212> TYPE: PRT
<213> ORGANISM: Mus musculus

<400> SEQUENCE: 416

Met Gly Trp Ser Cys Ile Met Leu Phe Leu Ala Ala Arg Ala Thr
1 5 10 15

<210> SEQ ID NO 417
<211> LENGTH: 15
<212> TYPE: PRT
<213> ORGANISM: Mus musculus

<400> SEQUENCE: 417

Met Gly Trp Ser Cys Ile Met Leu Phe Leu Ala Ala Thr Ala Thr
1 5 10 15

<210> SEQ ID NO 418
<211> LENGTH: 15
<212> TYPE: PRT
<213> ORGANISM: Mus musculus

<400> SEQUENCE: 418

Met Gly Trp Ser Cys Ile Met Leu Phe Leu Ala Ala Thr Ala Thr 1 5 10 15

<210> SEQ ID NO 419
<211> LENGTH: 15
<212> TYPE: PRT
<213> ORGANISM: Mus musculus

<400> SEQUENCE: 419

Met Gly Trp Ser Cys Ile Met Leu Phe Leu Ala Ala Thr Ala Thr
1 5 10 15

<210> SEQ ID NO 420
<211> LENGTH: 15
<212> TYPE: PRT
<213> ORGANISM: Mus musculus

<400> SEQUENCE: 420

Met Gly Trp Ser Cys Ile Met Leu Phe Leu Ala Ala Thr Ala Thr
1 5 10 15

<210> SEQ ID NO 421
<211> LENGTH: 15
<212> TYPE: PRT
<213> ORGANISM: Mus musculus

<400> SEQUENCE: 421

Met Gly Trp Ser Cys Ile Met Leu Phe Leu Ala Ala Thr Ala Thr
1 5 10 15

<210> SEQ ID NO 422
<211> LENGTH: 15
<212> TYPE: PRT
<213> ORGANISM: Mus musculus

<400> SEQUENCE: 422

Met Gly Trp Ser Cys Ile Met Leu Phe Leu Ala Ala Thr Ala Thr
1 5 10 15

<210> SEQ ID NO 423
<211> LENGTH: 15
<212> TYPE: PRT
<213> ORGANISM: Mus musculus

<400> SEQUENCE: 423

Met Gly Trp Ser Cys Ile Met Leu Phe Leu Ala Ala Thr Ala Thr
1 5 10 15

<210> SEQ ID NO 424
<211> LENGTH: 15
<212> TYPE: PRT
<213> ORGANISM: Mus musculus

<400> SEQUENCE: 424

Met Gly Trp Ser Arg Ile Phe Leu Phe Leu Leu Ser Ile Thr Ala
1 5 10 15

<210> SEQ ID NO 425
<211> LENGTH: 15
<212> TYPE: PRT
<213> ORGANISM: Mus musculus

<400> SEQUENCE: 425

Met Gly Trp Ser Ser Ile Ile Leu Phe Leu Val Ala Thr Ala Thr
1 5 10 15

<210> SEQ ID NO 426
<211> LENGTH: 15
<212> TYPE: PRT
<213> ORGANISM: Mus musculus

<400> SEQUENCE: 426

Met Gly Trp Ser Trp Ile Phe Leu Phe Leu Leu Ser Gly Ser Ala
1 5 10 15

<210> SEQ ID NO 427
<211> LENGTH: 15
<212> TYPE: PRT
<213> ORGANISM: Mus musculus

<400> SEQUENCE: 427

Met Gly Trp Ser Trp Ile Phe Leu Phe Leu Leu Ser Gly Thr Ala
1 5 10 15

<210> SEQ ID NO 428
<211> LENGTH: 15
<212> TYPE: PRT
<213> ORGANISM: Mus musculus

<400> SEQUENCE: 428

Met Gly Trp Ser Trp Ile Phe Leu Phe Leu Leu Ser Gly Thr Ala
1 5 10 15

<210> SEQ ID NO 429
<211> LENGTH: 15
<212> TYPE: PRT
<213> ORGANISM: Mus musculus

<400> SEQUENCE: 429

Met Gly Trp Ser Trp Ile Phe Leu Leu Phe Leu Ser Gly Thr Ala
1 5 10 15

<210> SEQ ID NO 430
<211> LENGTH: 15
<212> TYPE: PRT
<213> ORGANISM: Mus musculus

<400> SEQUENCE: 430

Met Gly Trp Ser Trp Ile Phe Pro Phe Leu Leu Ser Gly Thr Ala
1 5 10 15

<210> SEQ ID NO 431
<211> LENGTH: 15
<212> TYPE: PRT
<213> ORGANISM: Mus musculus

<400> SEQUENCE: 431

Met Gly Trp Ser Trp Ile Phe Pro Phe Leu Leu Ser Gly Thr Ala
1 5 10 15

<210> SEQ ID NO 432
<211> LENGTH: 15
<212> TYPE: PRT
<213> ORGANISM: Mus musculus

<400> SEQUENCE: 432

Met Gly Trp Ser Tyr Ile Ile Phe Phe Leu Val Ala Thr Ala Thr
1 5 10 15

<210> SEQ ID NO 433

<211> LENGTH: 15
<212> TYPE: PRT
<213> ORGANISM: Mus musculus

<400> SEQUENCE: 433

Met Gly Trp Ser Tyr Ile Ile Leu Phe Leu Val Ala Thr Ala Thr
1 5 10 15

<210> SEQ ID NO 434
<211> LENGTH: 15
<212> TYPE: PRT
<213> ORGANISM: Mus musculus

<400> SEQUENCE: 434

Met Gly Trp Ser Tyr Ile Ile Leu Phe Leu Val Ala Thr Ala Thr
1 5 10 15

<210> SEQ ID NO 435
<211> LENGTH: 15
<212> TYPE: PRT
<213> ORGANISM: Mus musculus

<400> SEQUENCE: 435

Met Gly Trp Ser Tyr Ile Ile Leu Phe Leu Val Ala Thr Ala Thr
1 5 10 15

<210> SEQ ID NO 436
<211> LENGTH: 15
<212> TYPE: PRT
<213> ORGANISM: Mus musculus

<400> SEQUENCE: 436

Met Leu Leu Gly Leu Lys Trp Val Phe Phe Val Val Phe Tyr Gln
1 5 10 15

<210> SEQ ID NO 437
<211> LENGTH: 15
<212> TYPE: PRT
<213> ORGANISM: Mus musculus

<400> SEQUENCE: 437

Met Arg Trp Ser Cys Ile Ile Leu Phe Leu Val Ala Thr Ala Thr
1 5 10 15

<210> SEQ ID NO 438
<211> LENGTH: 15
<212> TYPE: PRT
<213> ORGANISM: Mus musculus

<400> SEQUENCE: 438

Met Arg Trp Ser Cys Ile Ile Leu Phe Leu Val Ala Thr Ala Thr
1 5 10 15

<210> SEQ ID NO 439
<211> LENGTH: 16
<212> TYPE: PRT
<213> ORGANISM: Mus musculus

<400> SEQUENCE: 439

Met Val Ser Glu Thr His Val Leu Ile Phe Leu Leu Leu Trp Val Ser
1 5 10 15

<210> SEQ ID NO 440
<211> LENGTH: 10
<212> TYPE: PRT

<213> ORGANISM: Mus musculus

<400> SEQUENCE: 440

Ile Phe Leu Phe Leu Leu Ser Ile Thr Ala
1 5 10

<210> SEQ ID NO 441
<211> LENGTH: 15
<212> TYPE: PRT
<213> ORGANISM: Mus musculus

<400> SEQUENCE: 441

Ile Gly Trp Ser Tyr Ile Ile Leu Leu Leu Val Ala Thr Ala Thr
1 5 10 15

<210> SEQ ID NO 442
<211> LENGTH: 15
<212> TYPE: PRT
<213> ORGANISM: Mus musculus

<400> SEQUENCE: 442

Ile Lys Trp Ser Trp Ile Phe Leu Phe Leu Leu Ser Gly Thr Ala
1 5 10 15

<210> SEQ ID NO 443
<211> LENGTH: 15
<212> TYPE: PRT
<213> ORGANISM: Mus musculus

<400> SEQUENCE: 443

Ile Lys Trp Ser Trp Ile Ser Leu Phe Leu Leu Ser Gly Thr Ala
1 5 10 15

<210> SEQ ID NO 444
<211> LENGTH: 15
<212> TYPE: PRT
<213> ORGANISM: Mus musculus

<400> SEQUENCE: 444

Lys Gly Gly Ser Cys Val Ser Leu Phe Leu Val Ala Thr Ala Asn
1 5 10 15

<210> SEQ ID NO 445
<211> LENGTH: 15
<212> TYPE: PRT
<213> ORGANISM: Mus musculus

<400> SEQUENCE: 445

Met Ala Trp Ser Trp Val Phe Leu Phe Phe Leu Ser Val Thr Thr
1 5 10 15

<210> SEQ ID NO 446
<211> LENGTH: 15
<212> TYPE: PRT
<213> ORGANISM: Mus musculus

<400> SEQUENCE: 446

Met Glu Cys Ser Trp Val Phe Leu Phe Leu Leu Ser Leu Thr Ala
1 5 10 15

<210> SEQ ID NO 447
<211> LENGTH: 19
<212> TYPE: PRT
<213> ORGANISM: Mus musculus

<400> SEQUENCE: 447

Met Ile Tyr Ser Leu Gln Leu Leu Arg Met Leu Val Leu Trp Ile Pro
1 5 10 15

Ile Ser Lys

<210> SEQ ID NO 448
<211> LENGTH: 19
<212> TYPE: PRT
<213> ORGANISM: Mus musculus

<400> SEQUENCE: 448

Met Ser Tyr Ser Leu Gln Leu Leu Arg Met Leu Val Leu Trp Ile Pro
1 5 10 15

Ile Ser Lys

<210> SEQ ID NO 449
<211> LENGTH: 19
<212> TYPE: PRT
<213> ORGANISM: Mus musculus

<400> SEQUENCE: 449

Met Ser Tyr Ser Leu Gln Leu Leu Arg Met Leu Val Leu Trp Ile Pro
1 5 10 15

Ile Thr Lys

<210> SEQ ID NO 450
<211> LENGTH: 4
<212> TYPE: PRT
<213> ORGANISM: Mus musculus

<400> SEQUENCE: 450

Leu Val Leu Lys
1

<210> SEQ ID NO 451
<211> LENGTH: 15
<212> TYPE: PRT
<213> ORGANISM: Mus musculus

<400> SEQUENCE: 451

Met Ala Val Leu Gly Leu Leu Phe Cys Leu Val Thr Phe Pro Ser
1 5 10 15

<210> SEQ ID NO 452
<211> LENGTH: 15
<212> TYPE: PRT
<213> ORGANISM: Mus musculus

<400> SEQUENCE: 452

Met Ala Val Leu Gly Leu Leu Leu Cys Leu Val Thr Phe Pro Ser
1 5 10 15

<210> SEQ ID NO 453
<211> LENGTH: 15
<212> TYPE: PRT
<213> ORGANISM: Mus musculus

<400> SEQUENCE: 453

Met Asp Arg Leu Thr Ser Ser Phe Leu Leu Leu Ile Val Pro Ala
1 5 10 15

<210> SEQ ID NO 454

<211> LENGTH: 15
<212> TYPE: PRT
<213> ORGANISM: Mus musculus

<400> SEQUENCE: 454

Met Glu Trp Ser Trp Ile Phe Leu Phe Leu Leu Ser Gly Thr Ala
1 5 10 15

<210> SEQ ID NO 455
<211> LENGTH: 16
<212> TYPE: PRT
<213> ORGANISM: Mus musculus

<400> SEQUENCE: 455

Met Gly Arg Leu Thr Phe Ser Phe Leu Leu Leu Leu Pro Val Pro Ala
1 5 10 15

<210> SEQ ID NO 456
<211> LENGTH: 15
<212> TYPE: PRT
<213> ORGANISM: Mus musculus

<400> SEQUENCE: 456

Met Gly Trp Ser Cys Val Leu Leu Phe Leu Val Ser Gly Thr Ala
1 5 10 15

<210> SEQ ID NO 457
<211> LENGTH: 15
<212> TYPE: PRT
<213> ORGANISM: Mus musculus

<400> SEQUENCE: 457

Met Gly Trp Ser Trp Ile Phe Phe Phe Leu Leu Ser Gly Thr Ala
1 5 10 15

<210> SEQ ID NO 458
<211> LENGTH: 15
<212> TYPE: PRT
<213> ORGANISM: Mus musculus

<400> SEQUENCE: 458

Met Gly Trp Ser Trp Ile Phe Leu Phe Phe Leu Ser Gly Thr Ala
1 5 10 15

<210> SEQ ID NO 459
<211> LENGTH: 15
<212> TYPE: PRT
<213> ORGANISM: Mus musculus

<400> SEQUENCE: 459

Met Gly Trp Ser Trp Ile Phe Leu Phe Leu Leu Ser Gly Ser Ala
1 5 10 15

<210> SEQ ID NO 460
<211> LENGTH: 15
<212> TYPE: PRT
<213> ORGANISM: Mus musculus

<400> SEQUENCE: 460

Met Gly Trp Ser Trp Ile Phe Leu Phe Leu Leu Ser Gly Thr Ala
1 5 10 15

<210> SEQ ID NO 461
<211> LENGTH: 15
<212> TYPE: PRT

<213> ORGANISM: Mus musculus

<400> SEQUENCE: 461

Met Gly Trp Ser Trp Ile Phe Leu Phe Leu Leu Ser Gly Thr Ala
1 5 10 15

<210> SEQ ID NO 462
<211> LENGTH: 15
<212> TYPE: PRT
<213> ORGANISM: Mus musculus

<400> SEQUENCE: 462

Met Gly Trp Ser Trp Ile Phe Leu Leu Phe Leu Ser Gly Thr Ala
1 5 10 15

<210> SEQ ID NO 463
<211> LENGTH: 15
<212> TYPE: PRT
<213> ORGANISM: Mus musculus

<400> SEQUENCE: 463

Met Gly Trp Ser Trp Ile Phe Leu Leu Phe Leu Ser Gly Thr Ala
1 5 10 15

<210> SEQ ID NO 464
<211> LENGTH: 15
<212> TYPE: PRT
<213> ORGANISM: Mus musculus

<400> SEQUENCE: 464

Met Gly Trp Ser Trp Val Phe Leu Ser Phe Leu Ser Gly Thr Ala
1 5 10 15

<210> SEQ ID NO 465
<211> LENGTH: 16
<212> TYPE: PRT
<213> ORGANISM: Mus musculus

<400> SEQUENCE: 465

Met Asp Phe Gln Val Gln Ile Phe Ser Phe Leu Leu Ile Ser Ile Ser
1 5 10 15

<210> SEQ ID NO 466
<211> LENGTH: 15
<212> TYPE: PRT
<213> ORGANISM: Mus musculus

<400> SEQUENCE: 466

Met Ala Val Val Thr Gly Lys Gly Leu Pro Ser Pro Lys Leu Glu
1 5 10 15

<210> SEQ ID NO 467
<211> LENGTH: 15
<212> TYPE: PRT
<213> ORGANISM: Mus musculus

<400> SEQUENCE: 467

Met Gly Trp Ser Tyr Ile Ile Leu Phe Leu Val Ala Thr Ala Thr
1 5 10 15

<210> SEQ ID NO 468
<211> LENGTH: 11
<212> TYPE: PRT
<213> ORGANISM: Mus musculus

<400> SEQUENCE: 468

Met Gln Leu Gly His Leu Leu Pro Asp Gly Ser
1 5 10

<210> SEQ ID NO 469
<211> LENGTH: 16
<212> TYPE: PRT
<213> ORGANISM: Mus musculus

<400> SEQUENCE: 469

Arg Ser Val Pro Thr Gln Leu Leu Gly Leu Leu Leu Leu Trp Leu Thr
1 5 10 15

<210> SEQ ID NO 470
<211> LENGTH: 4
<212> TYPE: PRT
<213> ORGANISM: Mus musculus

<400> SEQUENCE: 470

Leu Ile Leu Lys
1

<210> SEQ ID NO 471
<211> LENGTH: 4
<212> TYPE: PRT
<213> ORGANISM: Mus musculus

<400> SEQUENCE: 471

Leu Val Leu Lys
1

<210> SEQ ID NO 472
<211> LENGTH: 5
<212> TYPE: PRT
<213> ORGANISM: Artificial
<220> FEATURE:
<223> OTHER INFORMATION: junction peptide

<400> SEQUENCE: 472

Gln Ile Trp Asn Asn
1 5

<210> SEQ ID NO 473
<211> LENGTH: 19
<212> TYPE: PRT
<213> ORGANISM: Mus musculus

<400> SEQUENCE: 473

Met Glu Ser Gln Asn His Val Leu Met Phe Leu Leu Leu Trp Val Ser
1 5 10 15

Thr Cys Gly

<210> SEQ ID NO 474
<211> LENGTH: 19
<212> TYPE: PRT
<213> ORGANISM: Mus musculus

<400> SEQUENCE: 474

Met Glu Ser Gln Thr His Val Leu Met Phe Leu Leu Leu Trp Val Ser
1 5 10 15

Thr Cys Gly

<210> SEQ ID NO 475

<211> LENGTH: 19
<212> TYPE: PRT
<213> ORGANISM: Mus musculus

<400> SEQUENCE: 475

Met Glu Ser Gln Thr Gln Val Phe Val Tyr Met Leu Leu Trp Leu Ser
1 5 10 15

Val Asp Gly

<210> SEQ ID NO 476
<211> LENGTH: 19
<212> TYPE: PRT
<213> ORGANISM: Mus musculus

<400> SEQUENCE: 476

Met Glu Ser Gln Thr Gln Val Leu Ile Ser Leu Leu Phe Trp Val Ser
1 5 10 15

Thr Cys Gly

<210> SEQ ID NO 477
<211> LENGTH: 19
<212> TYPE: PRT
<213> ORGANISM: Mus musculus

<400> SEQUENCE: 477

Met Glu Ser Gln Thr Gln Val Leu Met Phe Leu Leu Leu Trp Val Ser
1 5 10 15

Ala Cys Ala

<210> SEQ ID NO 478
<211> LENGTH: 19
<212> TYPE: PRT
<213> ORGANISM: Mus musculus

<400> SEQUENCE: 478

Met Glu Ser Gln Thr Gln Val Leu Met Ser Leu Leu Phe Trp Val Ser
1 5 10 15

Thr Cys Gly

<210> SEQ ID NO 479
<211> LENGTH: 19
<212> TYPE: PRT
<213> ORGANISM: Mus musculus

<400> SEQUENCE: 479

Met Glu Thr Asp Pro Leu Leu Leu Trp Val Leu Leu Leu Trp Val Pro
1 5 10 15

Ser Thr Gly

<210> SEQ ID NO 480
<211> LENGTH: 19
<212> TYPE: PRT
<213> ORGANISM: Mus musculus

<400> SEQUENCE: 480

Met Glu Thr Asp Thr Ile Leu Leu Trp Val Leu Leu Leu Trp Val Pro
1 5 10 15

Ser Thr Gly

<210> SEQ ID NO 481
<211> LENGTH: 19

<212> TYPE: PRT
<213> ORGANISM: Mus musculus

<400> SEQUENCE: 481

Met Glu Thr Asp Thr Leu Leu Leu Trp Val Leu Leu Leu Trp Val Pro
1 5 10 15

Ser Thr Gly

<210> SEQ ID NO 482
<211> LENGTH: 19
<212> TYPE: PRT
<213> ORGANISM: Mus musculus

<400> SEQUENCE: 482

Met Glu Thr Asp Thr Leu Leu Leu Trp Val Leu Leu Leu Trp Val Pro
1 5 10 15

Ser Thr Gly

<210> SEQ ID NO 483
<211> LENGTH: 19
<212> TYPE: PRT
<213> ORGANISM: Mus musculus

<400> SEQUENCE: 483

Met Glu Thr His Ser Gln Val Phe Val Tyr Met Leu Leu Trp Leu Ser
1 5 10 15

Val Glu Gly

<210> SEQ ID NO 484
<211> LENGTH: 23
<212> TYPE: PRT
<213> ORGANISM: Mus musculus

<400> SEQUENCE: 484

Met Gly Phe Lys Met Glu Ser His Thr Gln Ala Phe Val Phe Ala Phe
1 5 10 15

Leu Trp Leu Ser Val Asp Gly
20

<210> SEQ ID NO 485
<211> LENGTH: 16
<212> TYPE: PRT
<213> ORGANISM: Mus musculus

<400> SEQUENCE: 485

Met Gly Val Pro Thr Gln Leu Leu Leu Leu Trp Leu Thr Val Arg Cys
1 5 10 15

<210> SEQ ID NO 486
<211> LENGTH: 19
<212> TYPE: PRT
<213> ORGANISM: Mus musculus

<400> SEQUENCE: 486

Met Ile Ala Ser Ala Gln Phe Leu Gly Leu Leu Leu Leu Cys Phe Gln
1 5 10 15

Thr Arg Cys

<210> SEQ ID NO 487
<211> LENGTH: 19
<212> TYPE: PRT
<213> ORGANISM: Mus musculus

<400> SEQUENCE: 487

Met Lys Phe Pro Ser Gln Leu Leu Leu Phe Leu Leu Phe Arg Ile Thr
1 5 10 15

Ile Ile Cys

<210> SEQ ID NO 488
<211> LENGTH: 19
<212> TYPE: PRT
<213> ORGANISM: Mus musculus

<400> SEQUENCE: 488

Met Lys Phe Pro Ser Gln Leu Leu Leu Leu Leu Leu Phe Gly Ile Pro
1 5 10 15

Met Ile Cys

<210> SEQ ID NO 489
<211> LENGTH: 19
<212> TYPE: PRT
<213> ORGANISM: Mus musculus

<400> SEQUENCE: 489

Met Met Ser Ser Ala Gln Phe Leu Gly Leu Leu Leu Leu Cys Phe Gln
1 5 10 15

Thr Arg Cys

<210> SEQ ID NO 490
<211> LENGTH: 19
<212> TYPE: PRT
<213> ORGANISM: Mus musculus

<400> SEQUENCE: 490

Met Met Ser Ser Ala Gln Phe Leu Gly Leu Leu Leu Leu Cys Phe Gln
1 5 10 15

Thr Arg Tyr

<210> SEQ ID NO 491
<211> LENGTH: 19
<212> TYPE: PRT
<213> ORGANISM: Mus musculus

<400> SEQUENCE: 491

Met Asn Met Leu Thr Gln Leu Leu Gly Leu Leu Leu Leu Trp Phe Ala
1 5 10 15

Gly Lys Cys

<210> SEQ ID NO 492
<211> LENGTH: 19
<212> TYPE: PRT
<213> ORGANISM: Mus musculus

<400> SEQUENCE: 492

Met Arg Cys Leu Ala Glu Phe Leu Gly Leu Leu Val Leu Trp Ile Pro
1 5 10 15

Ala Ile Gly

<210> SEQ ID NO 493
<211> LENGTH: 19
<212> TYPE: PRT
<213> ORGANISM: Mus musculus

<400> SEQUENCE: 493

Met Arg Cys Leu Ala Glu Phe Leu Arg Leu Leu Val Leu Trp Ile Pro
1 5 10 15

Ala Thr Gly

<210> SEQ ID NO 494
<211> LENGTH: 19
<212> TYPE: PRT
<213> ORGANISM: Mus musculus

<400> SEQUENCE: 494

Met Arg Cys Ser Leu Gln Phe Leu Gly Val Leu Met Phe Trp Ile Ser
1 5 10 15

Val Ser Gly

<210> SEQ ID NO 495
<211> LENGTH: 19
<212> TYPE: PRT
<213> ORGANISM: Mus musculus

<400> SEQUENCE: 495

Met Arg Phe Ser Ala Gln Leu Leu Gly Leu Leu Val Leu Trp Ile Pro
1 5 10 15

Ser Thr Ala

<210> SEQ ID NO 496
<211> LENGTH: 19
<212> TYPE: PRT
<213> ORGANISM: Mus musculus

<400> SEQUENCE: 496

Met Arg Pro Ser Ile Gln Phe Leu Gly Leu Leu Leu Phe Trp Leu His
1 5 10 15

Ala Gln Cys

<210> SEQ ID NO 497
<211> LENGTH: 19
<212> TYPE: PRT
<213> ORGANISM: Mus musculus

<400> SEQUENCE: 497

Met Arg Val Leu Ala Glu Leu Leu Gly Leu Leu Leu Phe Cys Phe Leu
1 5 10 15

Val Arg Cys

<210> SEQ ID NO 498
<211> LENGTH: 19
<212> TYPE: PRT
<213> ORGANISM: Mus musculus

<400> SEQUENCE: 498

Met Arg Val Leu Pro Glu Phe Leu Gly Leu Leu Leu Leu Trp Ile Ser
1 5 10 15

Val Arg Cys

<210> SEQ ID NO 499
<211> LENGTH: 19
<212> TYPE: PRT
<213> ORGANISM: Mus musculus

<400> SEQUENCE: 499

Met Ser Ile Ser Thr Gln Leu Leu Gly Leu Leu Leu Leu Trp Leu Thr
1 5 10 15

Ala Arg Cys

<210> SEQ ID NO 500
<211> LENGTH: 19
<212> TYPE: PRT
<213> ORGANISM: Mus musculus

<400> SEQUENCE: 500

Met Ser Val Leu Thr Gln Val Leu Ala Leu Leu Leu Leu Trp Leu Thr
1 5 10 15

Ala Arg Cys

<210> SEQ ID NO 501
<211> LENGTH: 19
<212> TYPE: PRT
<213> ORGANISM: Mus musculus

<400> SEQUENCE: 501

Met Ser Val Pro Thr Gln Leu Leu Ala Leu Leu Leu Leu Trp Leu Thr
1 5 10 15

Ala Arg Cys

<210> SEQ ID NO 502
<211> LENGTH: 19
<212> TYPE: PRT
<213> ORGANISM: Mus musculus

<400> SEQUENCE: 502

Met Ser Val Pro Thr Gln Leu Leu Gly Leu Leu Leu Leu Trp Leu Thr
1 5 10 15

Ala Gly Cys

<210> SEQ ID NO 503
<211> LENGTH: 19
<212> TYPE: PRT
<213> ORGANISM: Mus musculus

<400> SEQUENCE: 503

Met Ser Val Pro Thr Gln Val Leu Gly Leu Leu Leu Leu Trp Leu Thr
1 5 10 15

Ala Arg Cys

<210> SEQ ID NO 504
<211> LENGTH: 19
<212> TYPE: PRT
<213> ORGANISM: Mus musculus

<400> SEQUENCE: 504

Met Val Phe Thr Pro Gln Ile Leu Gly Leu Met Leu Phe Trp Ile Ser
1 5 10 15

Ser Thr Gly

<210> SEQ ID NO 505
<211> LENGTH: 19
<212> TYPE: PRT
<213> ORGANISM: Mus musculus

<400> SEQUENCE: 505

-continued

```
Met Val Phe Thr Pro Gln Ile Leu Gly Leu Met Leu Phe Trp Ile Ser
1               5                   10                  15

Ser Arg Gly


<210> SEQ ID NO 506
<211> LENGTH: 18
<212> TYPE: PRT
<213> ORGANISM: Mus musculus

<400> SEQUENCE: 506

Met Val Leu Gly Leu Lys Trp Val Phe Phe Val Val Phe Tyr Gln Ser
1               5                   10                  15

Arg Gly


<210> SEQ ID NO 507
<211> LENGTH: 19
<212> TYPE: PRT
<213> ORGANISM: Mus musculus

<400> SEQUENCE: 507

Met Val Ser Thr Ser Gln Leu Leu Gly Leu Leu Leu Phe Trp Thr Ser
1               5                   10                  15

Ser Arg Gly


<210> SEQ ID NO 508
<211> LENGTH: 16
<212> TYPE: PRT
<213> ORGANISM: Mus musculus

<400> SEQUENCE: 508

Pro Ala Gln Phe Leu Phe Leu Leu Val Leu Trp Ile Gln Ser Arg Cys
1               5                   10                  15


<210> SEQ ID NO 509
<211> LENGTH: 18
<212> TYPE: PRT
<213> ORGANISM: Mus musculus

<400> SEQUENCE: 509

Met Gly Trp Ser Trp Ile Phe Leu Phe Leu Leu Ser Gly Thr Ala Val
1               5                   10                  15

Leu Ser


<210> SEQ ID NO 510
<211> LENGTH: 18
<212> TYPE: PRT
<213> ORGANISM: Mus musculus

<400> SEQUENCE: 510

Met Gly Trp Ser Trp Ile Phe Leu Phe Leu Leu Ser Gly Thr Ala Val
1               5                   10                  15

Leu Ser


<210> SEQ ID NO 511
<211> LENGTH: 18
<212> TYPE: PRT
<213> ORGANISM: Mus musculus

<400> SEQUENCE: 511

Met Gly Trp Ser Trp Ile Phe Leu Leu Phe Leu Ser Gly Thr Ala Val
1               5                   10                  15
```

-continued

Leu Ser

<210> SEQ ID NO 512
<211> LENGTH: 18
<212> TYPE: PRT
<213> ORGANISM: Mus musculus

<400> SEQUENCE: 512

Met Gly Trp Ser Trp Ile Phe Leu Leu Phe Leu Ser Gly Thr Ala Val
1 5 10 15

His Ser

<210> SEQ ID NO 513
<211> LENGTH: 18
<212> TYPE: PRT
<213> ORGANISM: Mus musculus

<400> SEQUENCE: 513

Met Gly Trp Ser Trp Ile Phe Leu Leu Phe Leu Ser Gly Thr Ala Val
1 5 10 15

Leu Ser

<210> SEQ ID NO 514
<211> LENGTH: 18
<212> TYPE: PRT
<213> ORGANISM: Mus musculus

<400> SEQUENCE: 514

Met Gly Trp Ser Trp Val Phe Leu Ser Phe Leu Ser Gly Thr Ala Val
1 5 10 15

Leu Ser

<210> SEQ ID NO 515
<211> LENGTH: 18
<212> TYPE: PRT
<213> ORGANISM: Mus musculus

<400> SEQUENCE: 515

Met Lys Cys Ser Trp Val Ile Phe Phe Leu Met Ala Val Val Ile Ile
1 5 10 15

Asn Ser

<210> SEQ ID NO 516
<211> LENGTH: 18
<212> TYPE: PRT
<213> ORGANISM: Mus musculus

<400> SEQUENCE: 516

Met Lys Leu Trp Leu Asn Trp Ile Leu Leu Val Ala Leu Leu Asn Ile
1 5 10 15

Gln Cys

<210> SEQ ID NO 517
<211> LENGTH: 18
<212> TYPE: PRT
<213> ORGANISM: Mus musculus

<400> SEQUENCE: 517

Met Leu Leu Gly Leu Lys Trp Val Phe Phe Val Val Phe Tyr Gln Val
1 5 10 15

His Cys

<210> SEQ ID NO 518
<211> LENGTH: 19
<212> TYPE: PRT
<213> ORGANISM: Mus musculus

<400> SEQUENCE: 518

Met Leu Leu Gly Leu Lys Trp Val Phe Phe Val Val Phe Tyr Gln Gly
1 5 10 15

Val His Cys

<210> SEQ ID NO 519
<211> LENGTH: 18
<212> TYPE: PRT
<213> ORGANISM: Mus musculus

<400> SEQUENCE: 519

Met Met Val Leu Ser Leu Leu Tyr Leu Leu Thr Ala Leu Pro Gly Ile
1 5 10 15

Leu Ser

<210> SEQ ID NO 520
<211> LENGTH: 18
<212> TYPE: PRT
<213> ORGANISM: Mus musculus

<400> SEQUENCE: 520

Met Asn Phe Gly Leu Ser Leu Ile Phe Leu Val Leu Ile Leu Lys Val
1 5 10 15

Gln Cys

<210> SEQ ID NO 521
<211> LENGTH: 14
<212> TYPE: PRT
<213> ORGANISM: Mus musculus

<400> SEQUENCE: 521

Met Gln Leu Gly His Leu Leu Pro Asp Gly Ser Val Asn Ser
1 5 10

<210> SEQ ID NO 522
<211> LENGTH: 19
<212> TYPE: PRT
<213> ORGANISM: Mus musculus

<400> SEQUENCE: 522

Met Val Ser Glu Thr His Val Leu Ile Phe Leu Leu Leu Trp Val Ser
1 5 10 15

Val His Cys

<210> SEQ ID NO 523
<211> LENGTH: 19
<212> TYPE: PRT
<213> ORGANISM: Mus musculus

<400> SEQUENCE: 523

Arg Ser Val Pro Thr Gln Leu Leu Gly Leu Leu Leu Leu Trp Leu Thr
1 5 10 15

Val Asn Ser

<210> SEQ ID NO 524

<211> LENGTH: 18
<212> TYPE: PRT
<213> ORGANISM: Mus musculus

<400> SEQUENCE: 524

Met Glu Trp Ser Gly Val Phe Ile Phe Leu Leu Ser Val Thr Ala Val
1 5 10 15

Tyr Ser

<210> SEQ ID NO 525
<211> LENGTH: 18
<212> TYPE: PRT
<213> ORGANISM: Mus musculus

<400> SEQUENCE: 525

Met Glu Trp Ser Arg Val Phe Ile Phe Leu Leu Ser Val Thr Ala Val
1 5 10 15

His Ser

<210> SEQ ID NO 526
<211> LENGTH: 18
<212> TYPE: PRT
<213> ORGANISM: Mus musculus

<400> SEQUENCE: 526

Met Glu Trp Ser Trp Val Phe Leu Phe Phe Leu Ser Val Thr Thr Val
1 5 10 15

His Ser

<210> SEQ ID NO 527
<211> LENGTH: 18
<212> TYPE: PRT
<213> ORGANISM: Mus musculus

<400> SEQUENCE: 527

Met Glu Trp Ser Trp Val Phe Leu Phe Leu Leu Ser Leu Thr Ser Val
1 5 10 15

His Ser

<210> SEQ ID NO 528
<211> LENGTH: 19
<212> TYPE: PRT
<213> ORGANISM: Mus musculus

<400> SEQUENCE: 528

Met Gly Arg Leu Thr Phe Ser Phe Leu Leu Leu Leu Pro Val Pro Ala
1 5 10 15

Val Leu Ser

<210> SEQ ID NO 529
<211> LENGTH: 18
<212> TYPE: PRT
<213> ORGANISM: Mus musculus

<400> SEQUENCE: 529

Met Gly Trp Ser Cys Ile Ile Phe Phe Leu Val Ala Thr Ala Thr Val
1 5 10 15

His Phe

<210> SEQ ID NO 530
<211> LENGTH: 18

<212> TYPE: PRT
<213> ORGANISM: Mus musculus

<400> SEQUENCE: 530

Met Gly Trp Ser Cys Ile Ile Leu Phe Leu Val Ala Ala Ala Asn Val
1 5 10 15

His Ser

<210> SEQ ID NO 531
<211> LENGTH: 18
<212> TYPE: PRT
<213> ORGANISM: Mus musculus

<400> SEQUENCE: 531

Met Gly Trp Ser Cys Ile Ile Leu Phe Leu Val Ala Ala Ala Thr Val
1 5 10 15

His Ser

<210> SEQ ID NO 532
<211> LENGTH: 18
<212> TYPE: PRT
<213> ORGANISM: Mus musculus

<400> SEQUENCE: 532

Met Gly Trp Ser Cys Ile Ile Leu Phe Leu Val Ala Thr Ala Thr Val
1 5 10 15

His Ser

<210> SEQ ID NO 533
<211> LENGTH: 18
<212> TYPE: PRT
<213> ORGANISM: Mus musculus

<400> SEQUENCE: 533

Met Gly Trp Ser Cys Ile Ile Leu Phe Leu Val Ala Thr Ala Thr Val
1 5 10 15

His Ser

<210> SEQ ID NO 534
<211> LENGTH: 18
<212> TYPE: PRT
<213> ORGANISM: Mus musculus

<400> SEQUENCE: 534

Met Gly Trp Ser Cys Ile Ile Leu Phe Leu Val Ser Thr Ala Thr Val
1 5 10 15

His Ser

<210> SEQ ID NO 535
<211> LENGTH: 18
<212> TYPE: PRT
<213> ORGANISM: Mus musculus

<400> SEQUENCE: 535

Met Gly Trp Ser Cys Ile Ile Leu Ile Leu Val Ala Ala Ala Thr Val
1 5 10 15

His Ser

<210> SEQ ID NO 536
<211> LENGTH: 18
<212> TYPE: PRT

<213> ORGANISM: Mus musculus

<400> SEQUENCE: 536

Met Gly Trp Ser Cys Ile Ile Leu Ile Leu Val Ala Ala Ala Thr Val
1 5 10 15

His Ser

<210> SEQ ID NO 537
<211> LENGTH: 18
<212> TYPE: PRT
<213> ORGANISM: Mus musculus

<400> SEQUENCE: 537

Met Gly Trp Ser Cys Ile Ile Leu Ile Leu Val Ala Ala Ala Thr Val
1 5 10 15

Gln Phe

<210> SEQ ID NO 538
<211> LENGTH: 18
<212> TYPE: PRT
<213> ORGANISM: Mus musculus

<400> SEQUENCE: 538

Met Gly Trp Ser Cys Ile Met Leu Phe Leu Ala Ala Arg Ala Thr Val
1 5 10 15

His Ser

<210> SEQ ID NO 539
<211> LENGTH: 18
<212> TYPE: PRT
<213> ORGANISM: Mus musculus

<400> SEQUENCE: 539

Met Gly Trp Ser Cys Ile Met Leu Phe Leu Ala Ala Thr Ala Thr Val
1 5 10 15

His Phe

<210> SEQ ID NO 540
<211> LENGTH: 18
<212> TYPE: PRT
<213> ORGANISM: Mus musculus

<400> SEQUENCE: 540

Met Gly Trp Ser Cys Ile Met Leu Phe Leu Ala Ala Thr Ala Thr Val
1 5 10 15

His Phe

<210> SEQ ID NO 541
<211> LENGTH: 18
<212> TYPE: PRT
<213> ORGANISM: Mus musculus

<400> SEQUENCE: 541

Met Gly Trp Ser Cys Ile Met Leu Phe Leu Ala Ala Thr Ala Thr Val
1 5 10 15

His Ser

<210> SEQ ID NO 542
<211> LENGTH: 18
<212> TYPE: PRT
<213> ORGANISM: Mus musculus

<400> SEQUENCE: 542

```
Met Gly Trp Ser Cys Ile Met Leu Phe Leu Ala Ala Thr Ala Thr Val
1               5                   10                  15

His Ser
```

<210> SEQ ID NO 543
<211> LENGTH: 18
<212> TYPE: PRT
<213> ORGANISM: Mus musculus

<400> SEQUENCE: 543

```
Met Gly Trp Ser Cys Ile Met Leu Phe Leu Ala Ala Thr Ala Thr Val
1               5                   10                  15

His Ser
```

<210> SEQ ID NO 544
<211> LENGTH: 19
<212> TYPE: PRT
<213> ORGANISM: Mus musculus

<400> SEQUENCE: 544

```
Met Gly Trp Ser Phe Leu Pro Leu Phe Leu Ala Ala Thr Ala Thr Gly
1               5                   10                  15

Val His Ser
```

<210> SEQ ID NO 545
<211> LENGTH: 18
<212> TYPE: PRT
<213> ORGANISM: Mus musculus

<400> SEQUENCE: 545

```
Met Gly Trp Ser Arg Ile Phe Leu Phe Leu Leu Ser Ile Thr Ala Val
1               5                   10                  15

His Cys
```

<210> SEQ ID NO 546
<211> LENGTH: 18
<212> TYPE: PRT
<213> ORGANISM: Mus musculus

<400> SEQUENCE: 546

```
Met Gly Trp Ser Ser Ile Ile Leu Phe Leu Val Ala Thr Ala Thr Val
1               5                   10                  15

His Ser
```

<210> SEQ ID NO 547
<211> LENGTH: 18
<212> TYPE: PRT
<213> ORGANISM: Mus musculus

<400> SEQUENCE: 547

```
Met Gly Trp Ser Trp Ile Phe Pro Phe Leu Leu Ser Gly Thr Ala Val
1               5                   10                  15

His Cys
```

<210> SEQ ID NO 548
<211> LENGTH: 18
<212> TYPE: PRT
<213> ORGANISM: Mus musculus

<400> SEQUENCE: 548

Met Gly Trp Ser Tyr Ile Ile Phe Phe Leu Val Ala Thr Ala Thr Val
1 5 10 15

His Phe

<210> SEQ ID NO 549
<211> LENGTH: 18
<212> TYPE: PRT
<213> ORGANISM: Mus musculus

<400> SEQUENCE: 549

Met Gly Trp Ser Tyr Ile Ile Phe Phe Leu Val Ala Thr Ala Thr Val
1 5 10 15

His Ser

<210> SEQ ID NO 550
<211> LENGTH: 18
<212> TYPE: PRT
<213> ORGANISM: Mus musculus

<400> SEQUENCE: 550

Met Gly Trp Ser Tyr Ile Ile Leu Phe Leu Val Ala Thr Ala Thr Gly
1 5 10 15

His Ser

<210> SEQ ID NO 551
<211> LENGTH: 18
<212> TYPE: PRT
<213> ORGANISM: Mus musculus

<400> SEQUENCE: 551

Met Gly Trp Ser Tyr Ile Ile Leu Phe Leu Val Ala Thr Ala Thr Val
1 5 10 15

His Ser

<210> SEQ ID NO 552
<211> LENGTH: 18
<212> TYPE: PRT
<213> ORGANISM: Mus musculus

<400> SEQUENCE: 552

Met Gly Trp Ser Tyr Ile Ile Leu Phe Leu Val Ala Thr Ala Thr Val
1 5 10 15

Asn Ser

<210> SEQ ID NO 553
<211> LENGTH: 18
<212> TYPE: PRT
<213> ORGANISM: Mus musculus

<400> SEQUENCE: 553

Met Arg Trp Ser Cys Ile Ile Leu Phe Leu Val Ala Thr Ala Thr Val
1 5 10 15

His Ser

<210> SEQ ID NO 554
<211> LENGTH: 16
<212> TYPE: PRT
<213> ORGANISM: Artificial
<220> FEATURE:
<223> OTHER INFORMATION: linker 8

-continued

```
<400> SEQUENCE: 554

Gly Gly Gly Gly Ser Gly Gly Gly Gly Ser Gly Gly Gly Gly Ser Gly
1               5                   10                  15


<210> SEQ ID NO 555
<211> LENGTH: 26
<212> TYPE: PRT
<213> ORGANISM: Artificial
<220> FEATURE:
<223> OTHER INFORMATION: linker 9

<400> SEQUENCE: 555

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly
            20                  25


<210> SEQ ID NO 556
<211> LENGTH: 17
<212> TYPE: PRT
<213> ORGANISM: Artificial
<220> FEATURE:
<223> OTHER INFORMATION: linker 10


<400> SEQUENCE: 556

Gly Gly Gly Gly Ser Gly Gly Gly Gly Ser Gly Gly Gly Gly Ser Gly
1               5                   10                  15

Gly


<210> SEQ ID NO 557
<211> LENGTH: 27
<212> TYPE: PRT
<213> ORGANISM: Artificial
<220> FEATURE:
<223> OTHER INFORMATION: linker 11

<400> SEQUENCE: 557

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly
            20                  25


<210> SEQ ID NO 558
<211> LENGTH: 38
<212> TYPE: DNA
<213> ORGANISM: Artificial
<220> FEATURE:
<223> OTHER INFORMATION: insertion of a unique HindIII and KasI
      restrictino site

<400> SEQUENCE: 558

aagcttcaac aggggagagt gttgaaggga gaggcgcc                              38
```